US008792983B2

(12) United States Patent
Von Arx et al.

(10) Patent No.: US 8,792,983 B2
(45) Date of Patent: *Jul. 29, 2014

(54) METHODS AND APPARATUSES FOR IMPLANTABLE MEDICAL DEVICE TELEMETRY POWER MANAGEMENT

(71) Applicant: Cardiac Pacemakers, Inc., St. Paul, MN (US)

(72) Inventors: Jeffrey A. Von Arx, Minneapolis, MN (US); David J. Yonce, Minneapolis, MN (US); Scott T. Mazar, Woodbury, MN (US); Karen M. Kramer, Marine on St. Croix, MN (US); Thomas J. Harris, Bloomington, MN (US)

(73) Assignee: Cardiac Pacemakers, Inc., St. Paul ( * ) Notice: Subject to any disclaimer, the term of this patent is extended or adjusted under 35 U.S.C. 154(b) by 0 days.

This patent is subject to a terminal disclaimer.

(21) Appl. No.: 14/019,830

(22) Filed: Sep. 6, 2013

(65) Prior Publication Data
US 2014/0012341 A1    Jan. 9, 2014

Related U.S. Application Data

(62) Division of application No. 12/684,303, filed on Jan. 8, 2010, now Pat. No. 8,538,528, which is a division of application No. 11/244,273, filed on Oct. 5, 2005, now Pat. No. 7,668,596, which is a division of application No. 10/071,255, filed on Feb. 7, 2002, now Pat. No. 6,985,773.

(51) Int. Cl.
*A61N 1/00* (2006.01)
(52) U.S. Cl.
USPC .......................................... 607/32

(58) Field of Classification Search
USPC ............. 607/60, 32; 128/903; 57/60, 32
See application file for complete search history.

(56) References Cited

U.S. PATENT DOCUMENTS 3,914,586 A    10/1975  McIntosh
4,341,982 A    7/1982   Lahti et al.
(Continued)

FOREIGN PATENT DOCUMENTS

DE    10119393 A1    1/2002
EP    0168640        1/1986
(Continued)

OTHER PUBLICATIONS

"U.S. Appl. No. 10/025,183, Appeal Brief filed Dec. 29, 2005", 27 pgs.
"U.S. Appl. No. 10/025,183, Final Office Action mailed Jan. 13, 2005", 7 pgs.
"U.S. Appl. No. 10/025,183, Final Office Action mailed May 25, 2005", 9 pgs.
(Continued)

*Primary Examiner* — Christopher D Koharski
*Assistant Examiner* — Roland Dinga
(74) *Attorney, Agent, or Firm* — Schwegman, Lundberg & Woessner, P.A.

(57) ABSTRACT

A method comprises connecting at least one portion of a far-field radio-frequency (RF) first telemetry circuit in an implantable medical device to an energy source through a power connection module, detecting information included in a first predetermined wireless signal, changing a conductivity state of the power connection module when the information in the first predetermined wireless signal is detected to couple power to the at least one portion of the first telemetry circuit, detecting a second predetermined wireless signal, and changing a conductivity state of the power connection module to decouple power to the at least one portion of the first telemetry circuit when the second predetermined wireless signal is detected and the first telemetry circuit enters an idle state.

20 Claims, 28 Drawing Sheets

(56) References Cited

U.S. PATENT DOCUMENTS

| | | |
|---|---|---|
| 4,404,972 A | 9/1983 | Gordon et al. |
| 4,441,498 A | 4/1984 | Nordling |
| 4,486,739 A | 12/1984 | Franaszek et al. |
| 4,519,401 A | 5/1985 | Ko et al. |
| 4,539,992 A | 9/1985 | Calfee et al. |
| 4,542,532 A | 9/1985 | McQuilkin |
| 4,542,535 A | 9/1985 | Bates et al. |
| 4,543,954 A | 10/1985 | Cook et al. |
| 4,561,443 A | 12/1985 | Hogrefe et al. |
| 4,562,841 A | 1/1986 | Brockway et al. |
| 4,592,360 A | 6/1986 | Lesnick |
| 4,613,937 A | 9/1986 | Batty, Jr. |
| 4,634,294 A | 1/1987 | Christol et al. |
| 4,731,814 A | 3/1988 | Becker et al. |
| 4,799,059 A | 1/1989 | Grindahl et al. |
| 4,803,987 A | 2/1989 | Calfee et al. |
| 4,944,299 A | 7/1990 | Silvian |
| 4,945,909 A | 8/1990 | Fearnot et al. |
| 4,987,897 A | 1/1991 | Funke |
| 5,025,808 A | 6/1991 | Hafner |
| 5,074,308 A | 12/1991 | Sholder et al. |
| 5,080,096 A | 1/1992 | Hooper et al. |
| 5,089,019 A | 2/1992 | Grandjean |
| 5,107,833 A * | 4/1992 | Barsness ............... 607/32 |
| 5,109,853 A | 5/1992 | Taicher et al. |
| 5,113,869 A | 5/1992 | Nappholz et al. |
| 5,171,977 A | 12/1992 | Morrison |
| 5,230,003 A | 7/1993 | Dent et al. |
| 5,287,384 A | 2/1994 | Avery et al. |
| 5,292,343 A | 3/1994 | Blanchette et al. |
| 5,300,093 A | 4/1994 | Koestner et al. |
| 5,314,453 A | 5/1994 | Jeutter |
| 5,342,408 A | 8/1994 | deCoriolis et al. |
| 5,350,411 A | 9/1994 | Ryan et al. |
| 5,350,412 A | 9/1994 | Hoegnelid et al. |
| 5,370,666 A | 12/1994 | Lindberg et al. |
| 5,394,433 A | 2/1995 | Bantz et al. |
| 5,404,877 A | 4/1995 | Nolan et al. |
| 5,456,692 A | 10/1995 | Smith, Jr. et al. |
| 5,466,246 A | 11/1995 | Silvian |
| 5,476,488 A | 12/1995 | Morgan et al. |
| 5,486,200 A | 1/1996 | Lindemans |
| 5,516,285 A | 5/1996 | Yacker et al. |
| 5,532,708 A | 7/1996 | Krenz et al. |
| 5,535,752 A | 7/1996 | Halperin et al. |
| 5,562,713 A | 10/1996 | Silvian |
| 5,568,510 A | 10/1996 | Tam |
| 5,577,087 A | 11/1996 | Furuyu |
| 5,579,876 A | 12/1996 | Adrian et al. |
| 5,593,430 A | 1/1997 | Renger |
| 5,598,847 A | 2/1997 | Renger |
| 5,603,331 A | 2/1997 | Heemels et al. |
| 5,617,871 A | 4/1997 | Burrows |
| 5,630,835 A | 5/1997 | Brownlee |
| 5,650,759 A | 7/1997 | Hittman et al. |
| 5,683,432 A | 11/1997 | Goedeke et al. |
| 5,694,952 A | 12/1997 | Lidman et al. |
| 5,697,958 A | 12/1997 | Paul et al. |
| 5,725,559 A | 3/1998 | Alt et al. |
| 5,729,680 A | 3/1998 | Belanger et al. |
| 5,733,313 A | 3/1998 | Barreras, Sr. et al. |
| 5,737,419 A | 4/1998 | Ganesan |
| 5,752,976 A | 5/1998 | Duffin et al. |
| 5,752,977 A | 5/1998 | Grevious et al. |
| 5,759,199 A | 6/1998 | Snell et al. |
| 5,764,699 A | 6/1998 | Needham et al. |
| 5,766,232 A | 6/1998 | Grevious et al. |
| 5,807,397 A | 9/1998 | Barreras |
| 5,833,603 A | 11/1998 | Kovacs et al. |
| 5,843,139 A | 12/1998 | Goedeke et al. |
| 5,861,019 A | 1/1999 | Sun et al. |
| 5,870,391 A | 2/1999 | Nago |
| 5,881,101 A | 3/1999 | Furman et al. |
| 5,887,022 A | 3/1999 | Lee |
| 5,895,485 A | 4/1999 | Loechel et al. |
| 5,898,397 A | 4/1999 | Murray |
| 5,904,708 A | 5/1999 | Goedeke |
| 5,919,210 A | 7/1999 | Lurie et al. |
| 5,940,384 A | 8/1999 | Carney et al. |
| 6,009,350 A | 12/1999 | Renken |
| 6,028,527 A | 2/2000 | Soenen et al. |
| 6,031,863 A | 2/2000 | Jusa et al. |
| 6,044,485 A | 3/2000 | Dent et al. |
| 6,083,248 A | 7/2000 | Thompson |
| 6,088,381 A | 7/2000 | Myers, Jr. |
| 6,093,146 A | 7/2000 | Filangeri |
| 6,115,583 A | 9/2000 | Brummer et al. |
| 6,115,634 A | 9/2000 | Donders et al. |
| 6,115,636 A | 9/2000 | Ryan |
| 6,128,528 A | 10/2000 | Erickson et al. |
| 6,130,905 A | 10/2000 | Wakayama |
| 6,155,208 A | 12/2000 | Schell et al. |
| 6,167,310 A | 12/2000 | Grevious |
| 6,167,312 A | 12/2000 | Goedeke |
| 6,169,925 B1 | 1/2001 | Villaseca et al. |
| 6,200,265 B1 | 3/2001 | Walsh et al. |
| 6,219,580 B1 | 4/2001 | Faltys et al. |
| 6,223,083 B1 | 4/2001 | Rosar |
| 6,240,317 B1 | 5/2001 | Villaseca et al. |
| 6,249,700 B1 | 6/2001 | Alt |
| 6,263,246 B1 | 7/2001 | Goedeke et al. |
| 6,275,737 B1 | 8/2001 | Mann |
| 6,309,350 B1 | 10/2001 | VanTassel et al. |
| 6,329,920 B1 | 12/2001 | Morrison et al. |
| 6,336,900 B1 | 1/2002 | Alleckson et al. |
| 6,336,903 B1 | 1/2002 | Bardy |
| 6,381,492 B1 | 4/2002 | Rockwell et al. |
| 6,385,318 B1 | 5/2002 | Oishi |
| 6,388,628 B1 | 5/2002 | Dettloff et al. |
| 6,400,990 B1 * | 6/2002 | Silvian ............... 607/60 |
| 6,416,471 B1 | 7/2002 | Kumar et al. |
| 6,424,867 B1 | 7/2002 | Snell et al. |
| 6,427,088 B1 | 7/2002 | Bowman, IV et al. |
| 6,434,429 B1 | 8/2002 | Kraus et al. |
| 6,443,891 B1 | 9/2002 | Grevious |
| 6,453,198 B1 | 9/2002 | Torgerson et al. |
| 6,456,256 B1 | 9/2002 | Amundson et al. |
| 6,456,875 B1 | 9/2002 | Wilkinson et al. |
| 6,463,329 B1 | 10/2002 | Goedeke |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,482,154 B1 | 11/2002 | Haubrich et al. |
| 6,490,487 B1 | 12/2002 | Kraus et al. |
| 6,505,072 B1 | 1/2003 | Linder et al. |
| 6,527,729 B1 | 3/2003 | Turcott |
| 6,531,982 B1 | 3/2003 | White et al. |
| 6,535,763 B1 | 3/2003 | Hiebert et al. |
| 6,535,766 B1 | 3/2003 | Thompson et al. |
| 6,562,000 B2 | 5/2003 | Thompson et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,567,793 B1 | 5/2003 | Hicks et al. |
| 6,574,503 B2 | 6/2003 | Ferek-Petric |
| 6,574,509 B1 | 6/2003 | Kraus et al. |
| 6,574,510 B2 | 6/2003 | Von Arx et al. |
| 6,577,900 B1 | 6/2003 | Silvian |
| 6,577,901 B2 | 6/2003 | Thompson et al. |
| 6,582,365 B1 | 6/2003 | Hines et al. |
| 6,585,644 B2 | 7/2003 | Lebel et al. |
| 6,600,949 B1 | 7/2003 | Turcott |
| 6,600,952 B1 | 7/2003 | Snell et al. |
| 6,602,191 B2 | 8/2003 | Quy |
| 6,609,029 B1 | 8/2003 | Mann et al. |
| 6,614,406 B2 | 9/2003 | Amundson et al. |
| 6,622,043 B1 | 9/2003 | Kraus et al. |
| 6,622,050 B2 | 9/2003 | Thompson |
| 6,624,786 B2 | 9/2003 | Boyle |
| 6,631,296 B1 | 10/2003 | Parramon et al. |
| 6,648,821 B2 | 11/2003 | Lebel et al. |
| 6,659,948 B2 | 12/2003 | Lebel et al. |
| 6,662,048 B2 | 12/2003 | Balczewski et al. |
| 6,671,328 B1 | 12/2003 | Poon et al. |

(56) References Cited

U.S. PATENT DOCUMENTS

| | | |
|---|---|---|
| 6,675,045 B2 | 1/2004 | Mass et al. |
| 6,687,546 B2 | 2/2004 | Lebel et al. |
| 6,708,065 B2 | 3/2004 | Von Arx et al. |
| 6,716,165 B1 | 4/2004 | Flanders et al. |
| 6,741,886 B2 | 5/2004 | Yonce |
| 6,752,765 B1 | 6/2004 | Jensen et al. |
| 6,763,269 B2 | 7/2004 | Cox |
| 6,768,730 B1 | 7/2004 | Whitehill |
| 6,801,807 B2 | 10/2004 | Abrahamson |
| 6,804,559 B1 | 10/2004 | Kraus et al. |
| 6,809,701 B2 | 10/2004 | Amundson et al. |
| 6,844,854 B2 | 1/2005 | Johnson et al. |
| 6,868,288 B2 | 3/2005 | Thompson |
| 6,873,870 B2 | 3/2005 | Ferek-Petric |
| 6,889,081 B2 | 5/2005 | Hsu |
| 6,897,788 B2 | 5/2005 | Khair et al. |
| 6,907,291 B1 | 6/2005 | Snell et al. |
| 6,951,596 B2 | 10/2005 | Green et al. |
| 6,970,735 B2 | 11/2005 | Uber, III et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,993,393 B2 | 1/2006 | Von Arx et al. |
| 7,013,178 B2 | 3/2006 | Reinke et al. |
| 7,027,872 B2 | 4/2006 | Thompson |
| 7,047,076 B1 | 5/2006 | Li et al. |
| 7,069,086 B2 | 6/2006 | Von Arx |
| 7,107,085 B2 | 9/2006 | Doi |
| 7,110,784 B2 | 9/2006 | Nasu et al. |
| 7,110,823 B2 | 9/2006 | Whitehurst et al. |
| 7,155,290 B2 | 12/2006 | Von et al. |
| 7,177,700 B1 | 2/2007 | Cox |
| 7,218,969 B2 | 5/2007 | Vallapureddy et al. |
| 7,228,182 B2 | 6/2007 | Healy et al. |
| 7,274,642 B2 | 9/2007 | Sako et al. |
| 7,280,872 B1 | 10/2007 | Mosesov et al. |
| 7,289,853 B1 | 10/2007 | Campbell et al. |
| 7,319,903 B2 | 1/2008 | Bange et al. |
| 7,324,012 B2 | 1/2008 | Mann et al. |
| 7,359,753 B2 | 4/2008 | Bange et al. |
| 7,406,349 B2 | 7/2008 | Seeberger et al. |
| 7,457,669 B2 | 11/2008 | Katoozi et al. |
| 7,475,245 B1 | 1/2009 | Healy et al. |
| 7,519,430 B2 | 4/2009 | Arx et al. |
| 7,539,489 B1 | 5/2009 | Alexander |
| 7,539,541 B2 | 5/2009 | Quiles et al. |
| 7,573,422 B2 | 8/2009 | Harvey et al. |
| 7,610,065 B2 | 10/2009 | Vallapureddy et al. |
| 7,623,922 B2 | 11/2009 | Bange et al. |
| 7,664,553 B2 | 2/2010 | Roberts |
| 7,668,596 B2 | 2/2010 | Von Arx et al. |
| 7,729,776 B2 | 6/2010 | Von Arx et al. |
| 7,738,964 B2 | 6/2010 | Von Arx et al. |
| 7,787,953 B2 | 8/2010 | Vallapureddy et al. |
| 7,818,067 B2 | 10/2010 | Healy et al. |
| 7,860,574 B2 | 12/2010 | Von Arx et al. |
| 7,881,802 B2 | 2/2011 | Quiles et al. |
| 7,890,180 B2 | 2/2011 | Quiles |
| 7,903,043 B2 | 3/2011 | Rawat et al. |
| 8,019,434 B2 | 9/2011 | Quiles et al. |
| 8,024,043 B2 | 9/2011 | Bange |
| 8,041,432 B2 | 10/2011 | Von Arx et al. |
| 8,238,975 B2 | 8/2012 | Vallapureddy et al. |
| 8,494,647 B2 | 7/2013 | Quiles |
| 8,538,528 B2 | 9/2013 | Von Arx et al. |
| 2001/0001014 A1 | 5/2001 | Akins et al. |
| 2001/0012955 A1 | 8/2001 | Goedeke et al. |
| 2001/0019614 A1 | 9/2001 | Madoukh |
| 2001/0027331 A1 | 10/2001 | Thompson |
| 2001/0047125 A1 | 11/2001 | Quy |
| 2002/0013614 A1 | 1/2002 | Thompson |
| 2002/0019606 A1 | 2/2002 | Lebel et al. |
| 2002/0032661 A1 | 3/2002 | Schuba et al. |
| 2002/0046276 A1 | 4/2002 | Coffey et al. |
| 2002/0049480 A1 | 4/2002 | Lebel et al. |
| 2002/0062139 A1 | 5/2002 | Ding |
| 2002/0065509 A1 | 5/2002 | Lebel et al. |
| 2002/0065539 A1 | 5/2002 | Von Arx et al. |
| 2002/0065540 A1 | 5/2002 | Lebel et al. |
| 2002/0109621 A1 | 8/2002 | Khair et al. |
| 2002/0115912 A1 | 8/2002 | Muraki et al. |
| 2002/0120838 A1 | 8/2002 | Abdulkader |
| 2002/0123672 A1 | 9/2002 | Christophersom et al. |
| 2002/0143372 A1 | 10/2002 | Snell et al. |
| 2002/0147388 A1 | 10/2002 | Mass et al. |
| 2002/0159545 A1 | 10/2002 | Ramesh et al. |
| 2002/0173830 A1 | 11/2002 | Starkweather et al. |
| 2002/0183806 A1 | 12/2002 | Abrahamson et al. |
| 2003/0018369 A1 | 1/2003 | Thompson et al. |
| 2003/0028902 A1 | 2/2003 | Cubley et al. |
| 2003/0041866 A1 | 3/2003 | Linberg et al. |
| 2003/0050535 A1 | 3/2003 | Bowman, IV et al. |
| 2003/0065919 A1 | 4/2003 | Albert et al. |
| 2003/0074036 A1 | 4/2003 | Prutchi et al. |
| 2003/0083719 A1 | 5/2003 | Shankar et al. |
| 2003/0097157 A1 | 5/2003 | Wohlgemuth et al. |
| 2003/0114891 A1 | 6/2003 | Hiebert et al. |
| 2003/0114897 A1 | 6/2003 | Von Arx et al. |
| 2003/0114898 A1* | 6/2003 | Von Arx et al. ............ 607/60 |
| 2003/0135246 A1 | 7/2003 | Mass et al. |
| 2003/0146835 A1 | 8/2003 | Carter |
| 2003/0149459 A1 | 8/2003 | Von Arx et al. |
| 2003/0159048 A1 | 8/2003 | Matsumoto et al. |
| 2003/0174069 A1 | 9/2003 | Goetz et al. |
| 2003/0187484 A1 | 10/2003 | Davis et al. |
| 2003/0216793 A1 | 11/2003 | Karlsson et al. |
| 2003/0220673 A1 | 11/2003 | Snell |
| 2004/0009815 A1 | 1/2004 | Zotto et al. |
| 2004/0030260 A1 | 2/2004 | Von Arx |
| 2004/0047434 A1 | 3/2004 | Waltho |
| 2004/0102815 A1 | 5/2004 | Balczewski et al. |
| 2004/0106967 A1 | 6/2004 | Von Arx et al. |
| 2004/0122489 A1 | 6/2004 | Mazar et al. |
| 2004/0127959 A1 | 7/2004 | Amundson et al. |
| 2004/0167587 A1 | 8/2004 | Thompson |
| 2004/0168071 A1 | 8/2004 | Silverbrook |
| 2004/0176811 A1 | 9/2004 | Von Arx et al. |
| 2004/0176822 A1 | 9/2004 | Thompson et al. |
| 2004/0215280 A1 | 10/2004 | Dublin et al. |
| 2004/0236382 A1 | 11/2004 | Dinsmoor et al. |
| 2004/0247047 A1 | 12/2004 | Dennis et al. |
| 2004/0260363 A1 | 12/2004 | Arx et al. |
| 2004/0263273 A1 | 12/2004 | Ahmed |
| 2005/0134520 A1 | 6/2005 | Rawat et al. |
| 2005/0203582 A1 | 9/2005 | Healy et al. |
| 2005/0204134 A1 | 9/2005 | Von Arx et al. |
| 2005/0222933 A1 | 10/2005 | Wesby |
| 2005/0240245 A1 | 10/2005 | Bange et al. |
| 2005/0245992 A1 | 11/2005 | Persen et al. |
| 2005/0261934 A1 | 11/2005 | Thompson |
| 2005/0283208 A1 | 12/2005 | Von Arx et al. |
| 2005/0283209 A1 | 12/2005 | Katoozi et al. |
| 2005/0288736 A1 | 12/2005 | Persen et al. |
| 2005/0288738 A1 | 12/2005 | Bange et al. |
| 2006/0025834 A1 | 2/2006 | Von Arx et al. |
| 2006/0029100 A1 | 2/2006 | Dove |
| 2006/0030901 A1 | 2/2006 | Quiles et al. |
| 2006/0030902 A1 | 2/2006 | Quiles et al. |
| 2006/0030903 A1 | 2/2006 | Seeberger et al. |
| 2006/0030904 A1 | 2/2006 | Quiles |
| 2006/0071756 A1 | 4/2006 | Steeves |
| 2006/0111054 A1 | 5/2006 | Pan et al. |
| 2006/0116744 A1 | 6/2006 | Von Arx et al. |
| 2006/0161222 A1 | 7/2006 | Haubrich et al. |
| 2006/0161223 A1 | 7/2006 | Vallapureddy et al. |
| 2006/0194615 A1 | 8/2006 | Vallapureddy et al. |
| 2006/0195161 A1 | 8/2006 | Li |
| 2006/0195162 A1 | 8/2006 | Arx et al. |
| 2006/0247736 A1 | 11/2006 | Roberts |
| 2007/0049983 A1 | 3/2007 | Freeberg |
| 2007/0100396 A1 | 5/2007 | Freeberg |
| 2007/0118188 A1 | 5/2007 | Von Arx et al. |
| 2007/0135216 A1 | 6/2007 | Martinek et al. |
| 2007/0169181 A1 | 7/2007 | Roskind |

(56) References Cited

U.S. PATENT DOCUMENTS

| | | | |
|---|---|---|---|
| 2007/0185550 | A1 | 8/2007 | Vallapureddy et al. |
| 2007/0260293 | A1 | 11/2007 | Carpenter et al. |
| 2007/0282398 | A1 | 12/2007 | Healy et al. |
| 2008/0015655 | A1 | 1/2008 | Bange et al. |
| 2008/0015656 | A1 | 1/2008 | Bange et al. |
| 2008/0046745 | A1 | 2/2008 | Buch et al. |
| 2008/0055070 | A1 | 3/2008 | Bange et al. |
| 2008/0114412 | A1 | 5/2008 | Bange et al. |
| 2008/0215121 | A1 | 9/2008 | Bange et al. |
| 2008/0262573 | A1 | 10/2008 | Seeberger et al. |
| 2008/0288024 | A1 | 11/2008 | Abrahamson |
| 2009/0216298 | A1 | 8/2009 | Quiles et al. |
| 2010/0045480 | A1 | 2/2010 | Vallapureddy et al. |
| 2010/0106224 | A1 | 4/2010 | Von Arx et al. |
| 2010/0114233 | A1 | 5/2010 | Von Arx et al. |
| 2010/0121414 | A1 | 5/2010 | Roberts |
| 2010/0152816 | A1 | 6/2010 | Von Arx et al. |
| 2011/0066211 | A1 | 3/2011 | Von Arx et al. |
| 2011/0098788 | A1 | 4/2011 | Quiles |
| 2011/0134013 | A1 | 6/2011 | Rawat et al. |

FOREIGN PATENT DOCUMENTS

| | | |
|---|---|---|
| EP | 0607638 | 7/1994 |
| EP | 0607638 A2 | 7/1994 |
| EP | 1050265 | 11/2000 |
| EP | 1062985 A2 | 12/2000 |
| EP | 1308184 A2 | 5/2003 |
| EP | 1495783 A1 | 1/2005 |
| JP | 08511702 | 12/1996 |
| JP | 2001251451 A | 9/2001 |
| JP | 2001274901 A | 10/2001 |
| JP | 2001285337 A | 10/2001 |
| JP | 2002112347 A | 4/2002 |
| JP | 2002132962 A | 5/2002 |
| JP | 2003022008 A | 1/2003 |
| JP | 2003299150 A | 10/2003 |
| JP | 2003348228 A | 12/2003 |
| JP | 2004094544 A | 3/2004 |
| JP | 2004104774 A | 4/2004 |
| JP | 2005281027 A | 10/2005 |
| WO | WO-9500202 A1 | 1/1995 |
| WO | WO-9819400 A1 | 5/1998 |
| WO | WO-9912302 A1 | 3/1999 |
| WO | WO-03053515 A1 | 7/2003 |
| WO | WO-2005000397 A1 | 1/2005 |
| WO | WO-2005091546 A2 | 9/2005 |
| WO | WO-2005091546 A3 | 9/2005 |
| WO | WO-2005099816 A1 | 10/2005 |
| WO | WO-2005099817 A1 | 10/2005 |
| WO | WO-2006020546 A1 | 2/2006 |
| WO | WO-2006020549 A1 | 2/2006 |
| WO | WO-2006116004 A1 | 11/2006 |
| WO | WO-2008027655 A1 | 3/2008 |

OTHER PUBLICATIONS

"U.S. Appl. No. 10/025,183, Final Office Action mailed Jul. 31, 2006", 7 pgs.
"U.S. Appl. No. 10/025,183, Final Office Action mailed Aug. 3, 2004", 7 pgs.
"U.S. Appl. No. 10/025,183, Non-Final Office Action mailed Feb. 15, 2006", 5 pgs.
"U.S. Appl. No. 10/025,183, Non-Final Office Action mailed Feb. 19, 2009", 5 pgs.
"U.S. Appl. No. 10/025,183, Non-Final Office Action mailed Mar. 4, 2004", 5 pgs.
"U.S. Appl. No. 10/025,183, Non-Final Office Action mailed Mar. 26, 2007", 4 pgs.
"U.S. Appl. No. 10/025,183, Non-Final Office Action mailed Dec. 10, 2007", 4 pgs.
"U.S. Appl. No. 10/025,183, Notice of Allowance mailed Sep. 14, 2007", 4 pgs.
"U.S. Appl. No. 10/025,183, Notice of Allowance mailed Sep. 18, 2008", 7 pgs.
"U.S. Appl. No. 10/025,183, Notice of Allowance mailed Sep. 28, 2009", 5 pgs.
"U.S. Appl. No. 10/025,183, Response filed Jan. 31, 2007 to Final Office Action mailed Jul. 31, 2006", 11 pgs.
"U.S. Appl. No. 10/025,183, Response filed Apr. 13, 2005 to Final Office Action mailed Jan. 13, 2005", 11 pgs.
"U.S. Appl. No. 10/025,183, Response filed May 12, 2008 to Non-Final Office Action mailed Dec. 10, 2007", 10 pgs.
"U.S. Appl. No. 10/025,183, Response filed May 15, 2006 to Non-Final Office Action mailed Feb. 15, 2006", 11 pgs.
"U.S. Appl. No. 10/025,183, Response filed Jun. 2, 2004 to Non-Final Office Action mailed Mar. 4, 2004", 11 pgs.
"U.S. Appl. No. 10/025,183, Response filed Jun. 12, 2009 to Non Final Office Action mailed Feb. 19, 2009", 10 pgs.
"U.S. Appl. No. 10/025,183, Response filed Jun. 26, 2007 to Non-Final Office Action mailed Mar. 26, 2007", 14 pgs.
"U.S. Appl. No. 10/025,183, Response filed Dec. 3, 2004 to Final Office Action mailed Aug. 3, 2004", 11 pgs.
"U.S. Appl. No. 10/025,223, Communication filed Nov. 16, 2004 to Final Office Action mailed Aug. 16, 2004", 1 pg.
"U.S. Appl. No. 10/025,223, Final Office Action mailed Aug. 16, 2004", 9 pgs.
"U.S. Appl. No. 10/025,223, Final Office Action mailed Sep. 10, 2004", 7 pgs.
"U.S. Appl. No. 10/025,223, Non Final Office Action mailed Mar. 1, 2005", 6 pgs.
"U.S. Appl. No. 10/025,223, Non Final Office Action mailed Mar. 19, 2004", 4 pgs.
"U.S. Appl. No. 10/025,223, Notice of Allowance mailed Aug. 10, 2005", 4 pgs.
"U.S. Appl. No. 10/025,223, Response filed Jan. 10, 2005 to Final Office Action mailed Sep. 10, 2004", 10 pgs.
"U.S. Appl. No. 10/025,223, Response filed Jun. 21, 2004 to Non Final Office Action mailed Mar. 19, 2004", 9 pgs.
"U.S. Appl. No. 10/025,223, Response filed Jun. 30, 2005 to Non Final Office Action mailed Mar. 1, 2005", 10 pgs.
"U.S. Appl. No. 10/071,255, Non Final Office Action mailed Jan. 7, 2005", 6 pgs.
"U.S. Appl. No. 10/071,255, Notice of Allowance mailed Jun. 15, 2005", 4 pgs.
"U.S. Appl. No. 10/071,255, Preliminary Amendment filed Oct. 5, 2005", 12 pgs.
"U.S. Appl. No. 10/071,255, Response filed Apr. 7, 2005 to Non Final Office Action mailed Jan. 7, 2005", 12 pgs.
"U.S. Appl. No. 10/071,255, Response filed Oct. 20, 2004 to Restriction Requirement mailed Sep. 28, 2004", 10 pgs.
"U.S. Appl. No. 10/071,255, Restriction Requirement mailed Sep. 28, 2004", 5 pgs.
"U.S. Appl. No. 10/744,943, Final Office Action mailed Feb. 21, 2008.", 15 pgs.
"U.S. Appl. No. 10/744,943, Response filed Oct. 22, 2007 to Non-Final Office Action mailed Apr. 20, 2007", 9 pgs.
"U.S. Appl. No. 10/914,496, Final Office Action mailed May 23, 2007", 11 pgs.
"U.S. Appl. No. 10/914,496, Final Office Action mailed Sep. 22, 2008", 12 pgs.
"U.S. Appl. No. 10/914,496, Non Final Office Action mailed Dec. 5, 2006", 9 pgs.
"U.S. Appl. No. 10/914,496, Non-Final Office Action mailed Mar. 18, 2008", 9 pgs.
"U.S. Appl. No. 10/914,496, Notice of Allowance mailed Jan. 16, 2009", 4 pgs.
"U.S. Appl. No. 10/914,496, Response filed Mar. 5, 2007 to Non Final office Action mailed Dec. 5, 2006", 13 pgs.
"U.S. Appl. No. 10/914,496, Response filed Jun. 18, 2008 to Non-Final Office Action mailed Mar. 18, 2008", 10 pgs.
"U.S. Appl. No. 10/914,496, Response filed Aug. 22, 2007 to Final Office Action mailed May 23, 2007", 12 pgs.
"U.S. Appl. No. 10/914,496, Response filed Nov. 24, 2008 to Final Office Action mailed Sep. 22, 2008", 9 pgs.
"U.S. Appl. No. 10/914,496, Response filed Dec. 12, 2007 to Restriction Requirement mailed Nov. 13, 2007", 7 pgs.

(56) References Cited

OTHER PUBLICATIONS

"U.S. Appl. No. 10/914,496, Restriction Requirement mailed Nov. 13, 2007", 5 pgs.

"U.S. Appl. No. 10/914,499, Advisory Action mailed Aug. 4, 2009", 5 pgs.

"U.S. Appl. No. 10/914,499, Final Office Action mailed Jan. 24, 2008", 10 pgs.

"U.S. Appl. No. 10/914,499, Final Office Action mailed May 12, 2009", 10 pgs.

"U.S. Appl. No. 10/914,499, Non Final Office Action mailed May 29, 2007", 11 pgs.

"U.S. Appl. No. 10/914,499, Non-Final Office Action mailed Feb. 3, 2010", 11 pgs.

"U.S. Appl. No. 10/914,499, Non-Final Office Action mailed Apr. 24, 2008", 5 pgs.

"U.S. Appl. No. 10/914,499, Non-Final Office Action mailed Nov. 5, 2008", 12 pgs.

"U.S. Appl. No. 10/914,499, Response filed Feb. 5, 2009 to Non-Final Office Action mailed Nov. 5, 2008", 12 pgs.

"U.S. Appl. No. 10/914,499, Response filed Apr. 14, 2008 to Final Office Action mailed Jan. 24, 2008", 11 pgs.

"U.S. Appl. No. 10/914,499, Response filed May 3, 2010 to Non-Final Office Action mailed Feb. 3, 2010", 12 pgs.

"U.S. Appl. No. 10/914,499, Response filed Jun. 30, 2008 to Non-Final Office Action mailed Apr. 24, 2008", 10 pgs.

"U.S. Appl. No. 10/914,499, Response filed Jul. 13, 2009 to Final Office Action mailed May 12, 2009", 10 pgs.

"U.S. Appl. No. 10/914,499, Response filed Aug. 31, 2010 to Final Office Action mailed Jul. 20, 2010", 10 pgs.

"U.S. Appl. No. 10/914,499, Response filed Oct. 23, 2007 to Non-Final Office Action mailed May 29, 2007", 11 pgs.

"U.S. Appl. No. 10/914,499, Response filed Nov. 10, 2009 to Advisory Action mailed Aug. 4, 2009", 12 pgs.

"U.S. Appl. No. 10/914,638, Final Office Action mailed Apr. 17, 2007", 10 pgs.

"U.S. Appl. No. 10/914,638, Non Final Office Action mailed Oct. 18, 2006", 9 pgs.

"U.S. Appl. No. 10/914,638, Notice of Allowance mailed Mar. 21, 2008", 4 pgs.

"U.S. Appl. No. 10/914,638, Notice of Allowance mailed Oct. 22, 2007", 4 pgs.

"U.S. Appl. No. 10/914,638, Response filed Jan. 18, 2007 to Non Final Office Action mailed Oct. 18, 2006", 16 pgs.

"U.S. Appl. No. 10/914,638, Response filed Aug. 17, 2007 to Final Office Action mailed Apr. 17, 2007", 8 pgs.

"U.S. Appl. No. 11/039,200, Non Final Office Action mailed Aug. 3, 2006", 10 pgs.

"U.S. Appl. No. 11/039,200, Notice of Allowance mailed Dec. 15, 2006", 4 pgs.

"U.S. Appl. No. 11/039,200, Response filed Nov. 2, 2006 to Non Final Office Action mailed Aug. 3, 2006", 9 pgs.

"U.S. Appl. No. 11/068,478, Advisory Action mailed Sep. 16, 2008", 3 pgs.

"U.S. Appl. No. 11/068,478, Final Office Action mailed Jun. 2, 2008", 17 pgs.

"U.S. Appl. No. 11/068,478, Non Final Office Action mailed Jan. 2, 2009", 11 pgs.

"U.S. Appl. No. 11/068,478, Non-Final Office Action mailed Dec. 17, 2007", 14 pgs.

"U.S. Appl. No. 11/068,478, Notice of Allowance mailed Jun. 9, 2009", 7 pgs.

"U.S. Appl. No. 11/068,478, Response filed Mar. 17, 2008 to Non Final Office Action mailed Dec. 17, 2007", 19 pgs.

"U.S. Appl. No. 11/068,478, Response filed Mar. 30, 2009 to Non Final Office Action mailed Jan. 2, 2009", 20 pgs.

"U.S. Appl. No. 11/068,478, Response filed Aug. 4, 2008 to Final Office Action mailed Jun. 2, 2008", 19 pgs.

"U.S. Appl. No. 11/068,478, Response filed Nov. 3, 2008 to Advisory Action mailed Sep. 16, 2008", 17 pgs.

"U.S. Appl. No. 11/101,142, Non-Final Office Action mailed Jun. 20, 2007", 8 pgs.

"U.S. Appl. No. 11/101,142, Notice of Allowance mailed Nov. 27, 2007", 6 pgs.

"U.S. Appl. No. 11/101,142, Response filed Jun. 4, 2007 to Restriction Requirement Response mailed May 3, 2007", 7 pgs.

"U.S. Appl. No. 11/101,142, Response filed Sep. 20, 2007 to Non-Final Office Action mailed Jun. 20, 2007", 7 pgs.

"U.S. Appl. No. 11/101,142, Restriction Requirement mailed May 3, 2007", 5 pgs.

"U.S. Appl. No. 11/101,196, Non Final Office Action mailed Mar. 29, 2007", 8 pgs.

"U.S. Appl. No. 11/101,196, Notice of Allowance mailed Aug. 27, 2007", 5 pgs.

"U.S. Appl. No. 11/101,196, Response filed Jun. 29, 2007 to Non Final Office Action mailed Mar. 29, 2007", 8 pgs.

"U.S. Appl. No. 11/244,273, Non-Final Office Action mailed Nov. 28, 2008", 7 pgs.

"U.S. Appl. No. 11/244,273, Notice of Allowance mailed Oct. 5, 2009", 7 pgs.

"U.S. Appl. No. 11/244,273, Response filed Mar. 2, 2009 to Non-Final Office Action mailed Nov. 28, 2008", 13 pgs.

"U.S. Appl. No. 11/244,273, Response filed Aug. 12, 2009 to Ex Parte Quayle mailed Jun. 12, 2009", 4 pgs.

"U.S. Appl. No. 11/244,273, Response filed Oct. 22, 2008 to Restriction Requirement mailed Jul. 22, 2008", 13 pgs.

"U.S. Appl. No. 11/244,273, Restriction Requirement mailed Jul. 22, 2008", 10 pgs.

"U.S. Appl. No. 11/325,564, Examiner Interview Summary mailed Jun. 24, 2009", 2 pgs.

"U.S. Appl. No. 11/325,584, Final Office Action mailed Oct. 24, 2008", 5 pgs.

"U.S. Appl. No. 11/325,584, Non-Final Office Action mailed Mar. 24, 2009", 5 pgs.

"U.S. Appl. No. 11/325,584, Non-Final Office Action mailed Apr. 10, 2008", 6 pgs.

"U.S. Appl. No. 11/325,584, Notice of Allowance mailed Mar. 23, 2010", 4 pgs.

"U.S. Appl. No. 11/325,584, Notice of Allowance mailed Oct. 21, 2009", 5 pgs.

"U.S. Appl. No. 11/325,584, Response filed Jan. 22, 2009 to Final Office Action mailed Oct. 24, 2008", 6 pgs.

"U.S. Appl. No. 11/325,584, Response filed Jun. 24, 2009 to Non-Final Office Action mailed Mar. 24, 2009", 9 pgs.

"U.S. Appl. No. 11/325,584, Response filed Jul. 10, 2008 to Non Final Office Action mailed Apr. 10, 2008", 9 pgs.

"U.S. Appl. No. 11/456,942, Advisory Action mailed May 7, 2009", 6 pgs.

"U.S. Appl. No. 11/456,942, Final Office Action mailed Mar. 10, 2009", 15 pgs.

"U.S. Appl. No. 11/456,942, Non-Final Office Action mailed Aug. 18, 2008", 15 pgs.

"U.S. Appl. No. 11/456,942, Notice of Allowance mailed Jul. 17, 2009", 13 pgs.

"U.S. Appl. No. 11/456,942, Response filed May 4, 2009 to Final Office Action mailed Mar. 10, 2009", 9 pgs.

"U.S. Appl. No. 11/456,942, Response filed Jun. 4, 2009 to Advisory Action mailed May 7, 2009", 10 pgs.

"U.S. Appl. No. 11/456,942, Response filed Nov. 18, 2008 to Non-Final Office Action mailed Aug. 18, 2008", 10 pgs.

"U.S. Appl. No. 11/733,339, Examiner Interview Summary mailed Aug. 13, 2009", 2 pgs.

"U.S. Appl. No. 11/733,339, Non-Final Office Action mailed Apr. 30, 2009", 10 pgs.

"U.S. Appl. No. 11/733,339, Non-Final Office Action mailed Sep. 9, 2009", 9 pgs.

"U.S. Appl. No. 11/733,339, Notice of Allowance mailed Feb. 25, 2010", 6 pgs.

"U.S. Appl. No. 11/733,339, Notice of Allowance mailed Apr. 21, 2010", 6 pgs.

"U.S. Appl. No. 11/733,339, Response filed Dec. 4, 2009 to Non Final Office Action mailed Sep. 9, 2009", 11 pgs.

(56) References Cited

OTHER PUBLICATIONS

"U.S. Appl. No. 12/145,343, Examiner Interview Summary mailed Apr. 12, 2012", 3 pgs.
"U.S. Appl. No. 12/145,343, Final Office Action mailed Feb. 2, 2012", 12 pgs.
"U.S. Appl. No. 12/145,343, Final Office Action mailed Mar. 8, 2011", 9 pgs.
"U.S. Appl. No. 12/145,343, Non Final Office Action mailed Jun. 7, 2012", 13 pgs.
"U.S. Appl. No. 12/145,343, Non Final Office Action mailed Sep. 30, 2011", 10 pgs.
"U.S. Appl. No. 12/145,343, Non-Final Office Action mailed Oct. 26, 2010", 10 pgs.
"U.S. Appl. No. 12/145,343, Response filed Jan. 25, 2011 to Non Final Office Action mailed Oct. 26, 2010", 9 pgs.
"U.S. Appl. No. 12/145,343, Response filed Apr. 27, 2012 to Final Office Action mailed Feb. 2, 2012", 11 pgs.
"U.S. Appl. No. 12/145,343, Response filed May 9, 2011 to Final Office Action mailed Mar. 8, 2011", 9 pgs.
"U.S. Appl. No. 12/145,343, Response filed Sep. 14, 2010 to Restriction Requirement mailed Aug. 26, 2010", 8 Pgs.
"U.S. Appl. No. 12/145,343, Response filed Dec. 28, 2011 to Non Final Office Action mailed Sep. 30, 2011", 12 pgs.
"U.S. Appl. No. 12/145,343, Restriction Requirement mailed Aug. 26, 2010", 7 pgs.
"U.S. Appl. No. 12/648,687, Notice of Allowance mailed Aug. 17, 2010", 7 pgs.
"U.S. Appl. No. 12/684,303, Final Office Action mailed Mar. 4, 2013", 8 pgs.
"U.S. Appl. No. 12/684,303, Non Final Office Action mailed Apr. 5, 2011", 5 pgs.
"U.S. Appl. No. 12/684,303, Non Final Office Action mailed May 2, 2012", 6 pgs.
"U.S. Appl. No. 12/684,303, Notice of Allowance mailed May 24, 2013", 9 pgs.
"U.S. Appl. No. 12/684,303, Response filed Apr. 1, 2013 to Final Office Action mailed Mar. 4, 2013", 9 pgs.
"U.S. Appl. No. 12/684,303, Response filed Jun. 13, 2011 to Non-Final Office Action mailed Apr. 5, 2011", 10 pgs.
"U.S. Appl. No. 12/684,303, Response filed Sep. 6, 2012 to Non Final Office Action mailed May 2, 2012", 8 pgs.
"U.S. Appl. No. 12/713,669, Non-Final Office Action mailed Mar. 2, 2011", 5 pgs.
"U.S. Appl. No. 12/713,669, Notice of Allowance mailed Jun. 24, 2011", 5 pgs.
"U.S. Appl. No. 12/713,669, Response filed May 16, 2011 to Non-Final Office Action mailed Mar. 2, 2011", 8 pgs.
"U.S. Appl. No. 12/950,359, Notice of Allowance mailed Jun. 23, 2011", 7 pgs.
"European Application Serial No. 02799254.4, Communication mailed Oct. 2, 2006", 4 pgs.
"European Application Serial No. 02799254.4, Office Action mailed Sep. 23, 2009", 4 pgs.
"European Application Serial No. 02799254.4, Response filed Feb. 15, 2010 to Office Action mailed Sep. 23, 2009", 12 pgs.
"European Application Serial No. 02799254.4, Response filed Apr. 2, 2007 to Communication mailed Oct. 2, 2006", 18 pgs.
"European Application Serial No. 03709003.2, Office Action mailed Jul. 27, 2010", 6 pgs.
"European Application Serial No. 03709003.2, Response filed Jan. 27, 2011 to office action mailed Jul. 27, 2010", 10.
"European Application Serial No. 05783799.9, Communication pursuant to Article 94(3) EPC mailed Jun. 16, 2009", 3 pgs.
"European Application Serial No. 05783799.9, Response filed Oct. 23, 2009 to Communication mailed Jun. 16, 2009", 9 pgs.
"European Application Serial No. 05783882.3, Communication pursuant to Article 94(3) EPC mailed Jun. 16, 2009", 3 pgs.
"European Application Serial No. 05783882.3, Response filed Oct. 22, 2009 to Communication mailed Jun. 16, 2009", 7 pgs.

"International Application No. PCT/US2002/040488, International Search Report mailed May 9, 2003", 7 pgs.
"International Application No. PCT/US2003/003748, International Search Report mailed Oct. 20, 2003", 5 pgs.
"International Application No. PCT/US2005/011606, International Search Report and Written Opinion mailed Jul. 26, 2005", 12 pgs.
"International Application No. PCT/US2005/028059, International Preliminary Report on Patentability mailed Feb. 13, 2007", 9 pgs.
"International Application No. PCT/US2005/028059, International Search Report and Written Opinion mailed Jan. 12, 2005", 13 pgs.
"International Application No. PCT/US2007/069424, International Search Report mailed Dec. 27, 2007", 4 pgs.
"International Application No. PCT/US2007/069424, Written Opinion mailed Dec. 27, 2007", 9 pgs.
"International Application No. PCT/US2007/069426, International Search Report mailed Dec. 27, 2007", 4 pgs.
"International Application No. PCT/US2007/069426, Written Opinion mailed Dec. 27, 2007", 8 pgs.
"Japanese Application Serial No. 2007-525695, Non Final Office Action mailed Oct. 7, 2011", (w/ English translation), 8 pgs.
"Japanese Application Serial No. 2007-525695, Office Action mailed Feb. 3, 2011", (w/ English Translation), 5 pgs.
"Japanese Application Serial No. 2007-525695, Office Action mailed Jun. 20, 2012", (w/ English Translation), 4 pgs.
"Japanese Application Serial No. 2007-525695, Office Action Response filed Jan. 6, 2012", (w/ English translation), 10 pgs.
"Japanese Application Serial No. 2007-525695, Response filed Apr. 20, 2011 to Non Final Office Action mailed Feb. 3, 2011", (w/ English Translation of Amended Claims), 10 pgs.
"Japanese Application Serial No. 2007-525695, Response filed Aug. 27, 2012 to Office Action mailed Jun. 20, 2012", (w/ English translation of claims), 8 pgs.
"Part III—Department of Health and Human Services, Office of the Secretary—45 CFR Part 142—Security and Electronic Signature Standards; Proposed Rule", Federal Register, 63(155), (Aug. 12, 1998), 43241-43280.
"Public Law 104-191 [H.R. 3103]—Health Insurance Portability and Accountability Act of 1996", United States Public Laws—104th Congress—2nd Session, (Aug. 21, 1996), 78 pgs.
Bange, Joseph E, et al., "U.S. Appl. No. 11/101,196, Application filed Apr. 7, 2005", 19 pgs.
Bange, Joseph E, et al., "Implantable Medical Device Telemetry With Adaptive Frequency Hopping", U.S. Appl. No. 11/456,937, filed Jul. 12, 2006, 35 pgs.
Bange, Joseph E, et al., "Implantable Medical Device Telemetry With Periodic Frequency Hopping", U.S. Appl. No. 11/456,942, filed Jul. 12, 2006, 43 pgs.
Diffie, W., "The First Ten Years of Public-Key Cryptography", Proceedings of the IEEE, 76(5), (May, 1988), 560-577.
Golmie, N., et al., "The Evolution of Wireless LANs and PANs - Bluetooth and WLAN coexistence: challenges and solutions", IEEE Personal Communications, 10(6), (Dec. 2003), 22-29.
Hammond, E., "Perspectives on Implementation of Administrative Simplification Provisions of P.L. 104-191", National Committee on Vital and Health Statistics, Subcommittee on Health Data Needs, Standards and Security, (Feb. 11, 1997), 4 pgs.
Healy, S. J., et al., "System and Method for Providing Secure Exchange of Sensitive Information With an Implantable Medical Device", U.S. Appl. No. 10/801,150, filed Mar. 15, 2004, 30 pgs.
Katoozi, M., et al., "On-Demand Retransmission of Data With an Implantable Medical Device", U.S. Appl. No. 10/870,328, filed Jun. 17, 2004, 30 pgs.
Quiles, S., "U.S. Appl. No. 10/914,499, filed Aug. 9, 2004", 30 pgs.
Quiles, S., "Secure Remote Access for an Implantable Medical Device", U.S. Appl. No. 10/914,641, filed Aug. 9, 2004, 41 pgs.
Quiles, Sylvia, "U.S. Appl. No. 10/914,496, filed Aug. 9, 2004", 23 pgs.
Rawat, Prashant, et al., "U.S. Appl. No. 10/744,943, filed Dec. 22, 2003", 34 pgs.
Seeberger, M., "Dynamic Telemetry Link Selection for an Implantable Device", U.S. Appl. No. 10/914,638, filed Aug. 9, 2004, 35 pgs.

(56) References Cited

OTHER PUBLICATIONS

Von Arx, J. A., et al., "A Telemetry Duty Cycle Management System for an Implantable Medical Device", U.S. Appl. No. 11/325,584, filed Jan. 4, 2006, 37 pgs.
Von Arx, J., et al., "System and Method for Securely Authenticating a Data Exchange Session With an Implantable Medical Device", U.S. Appl. No. 10/800,806, filed Mar. 15, 2004, 47 pgs.
Von Arx, Jeffrey, "U.S. Appl. No. 10/870,324, filed Jun. 14, 2004", 38 pgs.
Wikipedia, SHA hash functions: http://en.wikipedia.org/wiki/SHA, (1993), 8 pgs.
"U.S. Appl. No. 09/921,653, Notice of Allowance mailed May 7, 2002", 6 pgs.
"U.S. Appl. No. 10/252,494, Non Final Office Action mailed Jan. 30, 2003", 4 pgs.
"U.S. Appl. No. 10/252,494, Notice of Allowance mailed Mar. 25, 2003", 5 pgs.
"U.S. Appl. No. 10/252,494, Response filed Mar. 5, 2003 to Non Final Office Action mailed Jan. 30, 2003", 6 pgs.
"U.S. Appl. No. 10/269,905, Non Final Office Action mailed Jul. 27, 2005", 15 pgs.
"U.S. Appl. No. 10/269,905, Notice of Allowance mailed Jan. 20, 2006", 11 pgs.
"U.S. Appl. No. 10/269,905, Response filed Nov. 28, 2005 to Non Final Office Action mailed Jul. 27, 2005", 13 pgs.
"U.S. Appl. No. 10/601,763, Non Final Office Action mailed Feb. 23, 2006", 9 pgs.
"U.S. Appl. No. 10/601,763, Non-Final Office Action mailed Feb. 23, 2006", 9 pgs.
"U.S. Appl. No. 10/601,763, Notice of Allowance mailed Aug. 4, 2006", 8 pgs.
"U.S. Appl. No. 10/601,763, Response filed May 23, 2006 to Non Final Office Action mailed Feb. 23, 2006", 13 pgs.
"U.S. Appl. No. 10/601,763, Supplemental Notice of Allowability mailed Oct. 23, 2006", 4 pgs.
"U.S. Appl. No. 10/634,233, Notice of Allowance mailed Jun. 16, 2004", 6 pgs.
"U.S. Appl. No. 10/744,943, Non-Final Office Action mailed Mar. 19, 2010", 10 pgs.
"U.S. Appl. No. 10/744,943, Non-Final Office Action mailed Apr. 20, 2007", 8 pgs.
"U.S. Appl. No. 10/744,943, Non-Final Office Action mailed Aug. 1, 2006", 7 pgs.
"U.S. Appl. No. 10/744,943, Non-Final Office Action Mailed Aug. 7, 2009", 11 pgs.
"U.S. Appl. No. 10/744,943, Non-Final Office Action Mailed Oct. 28, 2008", 16 pgs.
"U.S. Appl. No. 10/744,943, Non-Final Office Action mailed Dec. 15, 2005", 7 pgs.
"U.S. Appl. No. 10/744,943, Notice of Allowance mailed Nov. 1, 2010", 7 pgs.
"U.S. Appl. No. 10/744,943, Response filed Feb. 1, 2007 to Non-Final Office Action mailed Aug. 1, 2006", 11 pgs.
"U.S. Appl. No. 10/744,943, Response filed Mar. 30, 2009 to Non Final Office Action mailed Oct. 28, 2008", 8 pgs.
"U.S. Appl. No. 10/744,943, Response filed May 15, 2006 to Non-Final Office Action mailed Dec. 5, 2005", 9 pgs.
"U.S. Appl. No. 10/744,943, Response filed Aug. 18, 2010 to Non Final Office Action mailed Mar. 19, 2010", 14 pgs.
"U.S. Appl. No. 10/744,943, Response filed Aug. 19, 2008 to Final Office Action mailed Feb. 21, 2008", 9 pgs.
"U.S. Appl. No. 10/744,943, Response filed Sep. 6, 2005 to Restriction Requirement mailed Aug. 3, 2005", 8 pgs.
"U.S. Appl. No. 10/744,943, Response filed Nov. 9, 2009 to Non Final Office Action mailed Aug. 7, 2009", 12 pgs.
"U.S. Appl. No. 10/744,943, Restriction Requirement mailed Aug. 3, 2005", 5 pgs.
"U.S. Appl. No. 10/801,070, 312 Amendment filed Apr. 11, 2007", 4 pgs.
"U.S. Appl. No. 10/801,070, Non Final Office Action mailed Feb. 6, 2006", 17 pgs.
"U.S. Appl. No. 10/801,070, Non Final Office Action mailed Jun. 16, 2006", 6 pgs.
"U.S. Appl. No. 10/801,070, Non-Final Office Action mailed Jun. 16, 2006", 6 pgs.
"U.S. Appl. No. 10/801,070, Non-Final Office Action mailed Feb. 6, 2006", 20 pgs.
"U.S. Appl. No. 10/801,070, Notice of Allowance mailed Jan. 12, 2007", 7 pgs.
"U.S. Appl. No. 10/801,070, Response filed Mar. 7, 2006 to Non Final Office Action mailed Feb. 6, 2006", 10 pgs.
"U.S. Appl. No. 10/801,070, Response filed Sep. 18, 2006 to Non Final Office Action mailed Jun. 16, 2006", 11 pgs.
"U.S. Appl. No. 10/801,070, Response filed Mar. 7, 2006 to Non-Final Office Action", 14 pgs.
"U.S. Appl. No. 10/801,070, Response filed Sep. 18, 2006 to Non Final Office Action mailed Jun. 16, 2006", 15 pgs.
"U.S. Appl. No. 10/870,324, Advisory Action mailed Mar. 21, 2008", 3 pgs.
"U.S. Appl. No. 10/870,324, Examiner Interview Summary mailed Feb. 13, 2008", 4 pgs.
"U.S. Appl. No. 10/870,324, Examiner Interview Summary mailed Sep. 28, 2007", 3 pgs.
"U.S. Appl. No. 10/870,324, Examiner Interview Summary mailed Oct. 25, 2007", 3 pgs.
"U.S. Appl. No. 10/870,324, Final Office Action mailed Jan. 8, 2008", 8 pgs.
"U.S. Appl. No. 10/870,324, Non Final Office Action mailed Jun. 27, 2007", 6 pgs.
"U.S. Appl. No. 10/870,324, Non-Final Office Action mailed May 14, 2008", 8 pgs.
"U.S. Appl. No. 10/870,324, Notice of Allowance mailed Dec. 1, 2008", 7 pgs.
"U.S. Appl. No. 10/870,324, Response filed Feb. 8, 2008 to Final Office Action mailed Jan. 8, 2008", 20 pgs.
"U.S. Appl. No. 10/870,324, Response filed Aug. 14, 2008 to Non-Final Office Action mailed May 14, 2008", 22 pgs.
"U.S. Appl. No. 10/870,324, Response filed Oct. 29, 2007 to Non Final Office Action mailed Jun. 27, 2007", 21 pgs.
"U.S. Appl. No. 10/870,328, Non Final Office Action mailed Aug. 16, 2007", 12 pgs.
"U.S. Appl. No. 10/870,328, Notice of Allowance mailed Jul. 24, 2008", 10 pgs.
"U.S. Appl. No. 10/870,328, Response filed Nov. 16, 2007 to Non-Final Office Action mailed Aug. 16, 2007", 17 pgs.
"U.S. Appl. No. 10/914,499, Final Office Action mailed Jul. 20, 2010", 5 pgs.
"U.S. Appl. No. 10/914,499, Notice of Allowance mailed Sep. 29, 2010", 4 pgs.
"U.S. Appl. No. 10/914,641, Final Office Action dated Apr. 17, 2007", 10 pgs.
"U.S. Appl. No. 10/914,641, Final Office Action mailed Feb. 20, 2008", 9 pgs.
"U.S. Appl. No. 10/914,641, Final Office Action mailed Mar. 10, 2009", 10 pgs.
"U.S. Appl. No. 10/914,641, Final Office Action mailed Mar. 11, 2010", 11 pgs.
"U.S. Appl. No. 10/914,641, Final office action mailed Mar. 15, 2007", 10 pgs.
"U.S. Appl. No. 10/914,641, Non Final Office Action mailed Aug. 2, 2006", 9 pgs.
"U.S. Appl. No. 10/914,641, Non Final Office Action mailed Aug. 18, 2009", 11 pgs.
"U.S. Appl. No. 10/914,641, Non Final Office Action mailed Aug. 22, 2008", 9 pgs.
"U.S. Appl. No. 10/914,641, Non Final Office Action Mailed Aug. 31, 2007", 9 pgs.
"U.S. Appl. No. 10/914,641, Non-Final Office Action mailed Oct. 18, 2006", 13 pgs.
"U.S. Appl. No. 10/914,641, Notice of Allowance dated Aug. 4, 2006", 8 pgs.

(56) References Cited

OTHER PUBLICATIONS

"U.S. Appl. No. 10/914,641, Notice of Allowance mailed Oct. 6, 2010", 5 pgs.

"U.S. Appl. No. 10/914,641, Response filed Jan. 2, 2007 to Non Final Office Action mailed Aug. 2, 2006", 9 pgs.

"U.S. Appl. No. 10/914,641, Response filed Jan. 18, 2007 to Non-Final Office Action", 21 pgs.

"U.S. Appl. No. 10/914,641, Response filed May 11, 2009 to Final Office Action mailed Mar. 10, 2009", 12 pgs.

"U.S. Appl. No. 10/914,641, Response filed May 18, 2010 to Final Office Action mailed Mar. 11, 2010", 11 pgs.

"U.S. Appl. No. 10/914,641, Response filed May 23, 2006 to Non-Final Office Action mailed Feb. 6, 2006", 18 pgs.

"U.S. Appl. No. 10/914,641, Response filed Jun. 10, 2009 to Advisory Action mailed Mar. 10, 2009", 11 pgs.

"U.S. Appl. No. 10/914,641, Response filed Jun. 16, 2006 to Restriction Requirement mailed May 16, 2006", 5 pgs.

"U.S. Appl. No. 10/914,641, Response filed Jul. 16, 2007 to Final Office Action mailed Mar. 15, 2007", 9 pgs.

"U.S. Appl. No. 10/914,641, Response filed Nov. 18, 2009 to Non Final Office Action mailed Aug. 18, 2009", 11 pgs.

"U.S. Appl. No. 10/914,641, Response filed Nov. 24, 2008 to Non Final Office Action mailed Aug. 22, 2008", 11 pgs.

"U.S. Appl. No. 10/914,641, Response filed Nov. 30, 2007 to Non Final Office Action mailed Aug. 31, 2007", 14 pgs.

"U.S. Appl. No. 10/914,641, Restriction Requirement mailed May 16, 2006", 5 pgs.

"U.S. Appl. No. 11/068,478, Corrected Notice of Allowance mailed Jun. 19, 2009", 4 pgs.

"U.S. Appl. No. 11/116,108, Advisory Action mailed Jan. 29, 2009", 3 pgs.

"U.S. Appl. No. 11/116,108, Final Office Action mailed Oct. 10, 2008", 7 pgs.

"U.S. Appl. No. 11/116,108, Non-Final Office Action mailed Mar. 20, 2008", 11 pgs.

"U.S. Appl. No. 11/116,108, Non-Final Office Action mailed Apr. 23, 2009", 7 pgs.

"U.S. Appl. No. 11/116,108, Notice of Allowance mailed Sep. 29, 2009", 8 pgs.

"U.S. Appl. No. 11/116,108, Response filed Jun. 20, 2008 to Non-Final Office Action mailed Mar. 20, 2008", 9 pgs.

"U.S. Appl. No. 11/116,108, Response filed Jul. 23, 2009 to Non Final Office Action mailed Apr. 23, 2009", 7 pgs.

"U.S. Appl. No. 11/116,108, Response filed Dec. 10, 2008 to Final Office Action mailed Oct. 10, 2008", 6 pgs.

"U.S. Appl. No. 11/381,493, Appeal Brief filed Nov. 16, 2009", 19 pgs.

"U.S. Appl. No. 11/381,493, Decision on Appeal mailed Sep. 25, 2012", 14 pgs.

"U.S. Appl. No. 11/381,493, Examiners Answer mailed Mar. 25, 2010", 20 pgs.

"U.S. Appl. No. 11/381,493, Final Office Action mailed Jan. 8, 2009", 12 pgs.

"U.S. Appl. No. 11/381,493, Final Office Action mailed Apr. 16, 2009", 14 pgs.

"U.S. Appl. No. 11/381,493, Non Final Office Action mailed Dec. 13, 2013", 4 pgs.

"U.S. Appl. No. 11/381,493, Non-Final Office Action mailed Jun. 23, 2008", 13 pgs.

"U.S. Appl. No. 11/381,493, Reply Brief filed Apr. 29, 2010", 6 pgs.

"U.S. Appl. No. 11/381,493, Response filed Mar. 9, 2009 to Final Office Action mailed Jan. 8, 2009", 13 pgs.

"U.S. Appl. No. 11/381,493, Response filed Apr. 28, 2008 to Restriction Requirement mailed Mar. 26, 2008", 9 pgs.

"U.S. Appl. No. 11/381,493, Response filed Jun. 9, 2009 to Final Office Action mailed Apr. 16, 2009", 13 pgs.

"U.S. Appl. No. 11/381,493, Response filed Sep. 22, 2008 to Non-Final Office Action mailed Jun. 23, 2008", 15 pgs.

"U.S. Appl. No. 11/381,493, Restriction Requirement mailed Mar. 26, 2008", 7 pgs.

"U.S. Appl. No. 11/640,552, Examiner Interview Summary mailed May 27, 2010", 4 pgs.

"U.S. Appl. No. 11/640,552, Examiner Interview Summary mailed Aug. 10, 2009", 3 pgs.

"U.S. Appl. No. 11/640,552, Final Office Action mailed Mar. 24, 2010", 8 pgs.

"U.S. Appl. No. 11/640,552, Non Final Office Action mailed May 11, 2009", 8 pgs.

"U.S. Appl. No. 11/640,552, Non Final Office Action mailed Jul. 29, 2013", 6 pgs.

"U.S. Appl. No. 11/640,552, Notice of Allowance mailed Nov. 25, 2013", 7 pgs.

"U.S. Appl. No. 11/640,552, Response filed Jun. 24, 2010 to Final Office Action mailed Mar. 24, 2010", 9 pgs.

"U.S. Appl. No. 11/640,552, Response filed Aug. 11, 2009 to Non Final Office Action mailed May 11, 2009", 10 pgs.

"U.S. Appl. No. 11/640,552, Response filed Oct. 17, 2013 to Non Final Office Action mailed Jul. 29, 2013", 8 pgs.

"U.S. Appl. No. 11/738,942, Non Final Office Action mailed Jan. 20, 2010", 8 pgs.

"U.S. Appl. No. 11/738,942, Non Final Office Action mailed Jul. 9, 2009", 14 pgs.

"U.S. Appl. No. 11/738,942, Notice of Allowance mailed Jun. 17, 2010", 8 pgs.

"U.S. Appl. No. 11/738,942, Preliminary Amendment filed Apr. 23, 2007", 6 pgs.

"U.S. Appl. No. 11/738,942, Response filed Apr. 20, 2010 to Non Final Office Action mailed Jan. 20, 2010", 10 pgs.

"U.S. Appl. No. 11/738,942, Response filed Sep. 16, 2009 to Non Final Office Action mailed Jun. 9, 2009", 9 pgs.

"U.S. Appl. No. 12/004,892, Final Office Action mailed Sep. 14, 2011", 8 pgs.

"U.S. Appl. No. 12/102,480, Final Office Action mailed Jan. 18, 2011", 6 pgs.

"U.S. Appl. No. 12/102,480, Non-Final Office Action mailed Aug. 18, 2010", 9 pgs.

"U.S. Appl. No. 12/102,480, Notice of Allowance mailed May 19, 2011", 8 pgs.

"U.S. Appl. No. 12/102,480, Response filed Apr. 18, 2011 to Final Office Action mailed Jan. 18, 2011", 9 pgs.

"U.S. Appl. No. 12/102,480, Response filed Nov. 18, 2010 to Non Final Office Action mailed Aug. 18, 2010", 13 pgs.

"U.S. Appl. No. 12/145,343, Examiner Interview Summary mailed Aug. 21, 2013", 3 pgs.

"U.S. Appl. No. 12/145,343, Final Office Action mailed Jun. 7, 2013", 16 pgs.

"U.S. Appl. No. 12/145,343, Non Final Office Action mailed Nov. 7, 2013", 12 pgs.

"U.S. Appl. No. 12/145,343, Response filed Jul. 19, 2013 to Final Office Action mailed Jun. 7, 2013", 10 pgs.

"U.S. Appl. No. 12/145,343, Response filed Jul. 25, 2013 to Final Office Action mailed Jun. 7, 2013", 10 pgs.

"U.S. Appl. No. 12/145,343, Response filed Sep. 7, 2012 to Non Final Office Action mailed Jun. 7, 2012", 11 pgs.

"U.S. Appl. No. 12/435,928, Non-Final Office Action mailed Oct. 22, 2010", 14 pgs.

"U.S. Appl. No. 12/435,928, Notice of Allowance mailed May 4, 2011", 9 pgs.

"U.S. Appl. No. 12/435,928, Response filed Jan. 21, 2011 to Non Final Office Action mailed Oct. 22, 2010", 13 pgs.

"U.S. Appl. No. 12/604,254, Non Final Office Action mailed Nov. 2, 2011", 7 pgs.

"U.S. Appl. No. 12/604,254, Notice of Allowance mailed Mar. 30, 2012", 5 pgs.

"U.S. Appl. No. 12/604,254, Response filed Feb. 29, 2012 to Non Final Office Action mailed Nov. 2, 2011", 9 pgs.

"U.S. Appl. No. 12/604,254, Supplemental Notice of Allowability mailed Jul. 12, 2012", 2 pgs.

"U.S. Appl. No. 12/691,364, Advisory Action mailed Mar. 30, 2011", 3 pgs.

"U.S. Appl. No. 12/691,364, Final Office Action mailed Dec. 28, 2010", 8 pgs.

(56) References Cited

OTHER PUBLICATIONS

"U.S. Appl. No. 12/691,364, Non-Final Office Action mailed Jul. 20, 2010", 7 pgs.
"U.S. Appl. No. 12/691,364, Response filed Feb. 17, 2011 to Final Office Action mailed Dec. 28, 2010", 9 pgs.
"U.S. Appl. No. 12/691,364, Response filed Oct. 18, 2010 to Non-Final Office Action mailed Jul. 20, 2010", 11 pgs.
"U.S. Appl. No. 12/986,333, Final Office Action mailed Dec. 11, 2012", 8 pgs.
"U.S. Appl. No. 12/986,333, Non Final Office Action mailed Jun. 22, 2012", 7 pgs.
"U.S. Appl. No. 12/986,333, Notice of Allowance mailed Mar. 27, 2013", 6 pgs.
"U.S. Appl. No. 12/986,333, Response filed Jan. 9, 2013 to Final Office Action mailed Dec. 11, 2012", 8 pgs.
"U.S. Appl. No. 12/986,333, Response filed Sep. 7, 2012 to Non Final Office Action mailed Jun. 22, 2012", 9 pgs.
"European Application Serial No. 05732873.4, Communication dated Feb. 13, 2007", 3 pgs.
"European Application Serial No. 05732873.4, Communication dated Nov. 15, 2006", 2 pgs.
"European Application Serial No. 05732873.4, Office Action mailed Mar. 23, 2010", 2 Pgs.
"European Application Serial No. 05732873.4, Response filed Aug. 10, 2007 to Communication dated Feb. 13, 2007", 13 pgs.
"European Application Serial No. 05732873.4, Response filed Oct. 1, 2010 to Office Action mailed Mar. 23, 2010", 11 pgs.
"European Application Serial No. 05737578.4, Communication dated Feb. 13, 2007", 3 pgs.
"European Application Serial No. 05737578.4, European Office Action mailed Jul. 13, 2010", 4 pgs.
"European Application Serial No. 05737578.4, Office Action Response Filed Nov. 22, 2010", 12 pgs.
"European Application Serial No. 05737578.4, Response filed Aug. 10, 2007 to Communication dated Feb. 13, 2007", 15 pgs.
"European Application Serial No. 05783799.9, Office Action mailed Oct. 25, 2010", 3 pgs.
"European Application Serial No. 05783799.9, Response filed May 3, 2011 to Office Action mailed Oct. 25, 2010", 12 pgs.
"European Application Serial No. 06750873.9, Office Action mailed Apr. 14, 2010", 5 pgs.
"European Application Serial No. 06750873.9, Office Action mailed May 7, 2009", 2 pgs.
"European Application Serial No. 06750873.9, Office Action Response Filed Oct. 22, 2010", 13 pgs.
"European Application Serial No. 06750873.9, Response filed Sep. 16, 2009 to Communication mailed May 7, 2009", 7 pgs.
"International Application No. PCT/US2004/019902, International Search Report dated Dec. 6, 2004", 4 pgs.
"International Application No. PCT/US2004/019902, Written Opinion dated Dec. 6, 2004", 6 pgs.
"International Application No. PCT/US2005/008521, International Preliminary Report on Patentability mailed Sep. 28, 2006", 13 pgs.
"International Application No. PCT/US2005/008521, International Search Report and Written Opinion mailed Oct. 11, 2005", 19 pgs.
"International Application No. PCT/US2005/008521, International Search Report mailed Oct. 11, 2005", 19 pgs.
"International Application No. PCT/US2005/008521, Invitation to Pay Additional Fees and Partial International Search Report mailed Jul. 29, 2005", 7 pgs.
"International Application No. PCT/US2005/011639, International Search Report and Written Opinion mailed Aug. 26, 2005", 12 pgs.
"International Application No. PCT/US2005/028052, International Preliminary Report on Patentability mailed Feb. 22, 2007", 8 pgs.
"International Application No. PCT/US2005/028052, International Search Report and Written Opinion mailed Nov. 29, 2005", 12 pgs.
"International Application No. PCT/US2005/028059, International Search Report and Written Opinion mailed Dec. 1, 2005", 13 pgs.
"International Application No. PCT/US2006/014957, International Search Report and Written Opinion mailed Sep. 29, 2006", 16 pgs.
"International Application No. PCT/US2007/072827, International Search Report mailed Dec. 10, 2007", 4 pgs.
"International Application No. PCT/US2007/072827, Written Opinion mailed Dec. 10, 2007", 6 pgs.
"Japanese Application Serial No. 2006-517513, Office Action mailed Jan. 18, 2010", (w/ English Translation), 5 pgs.
"Japanese Application Serial No. 2006-517513, Office Action mailed Oct. 12, 2010", (W/ English Translation), 11 pgs.
"Japanese Application Serial No. 2006-517513, Response filed Apr. 19, 2010 to Office Action mailed Jan. 18, 2010", (w/ English Translation of Amended Claims), 41 pgs.
"Japanese Application Serial No. 2006-517513, Response filed Dec. 13, 2010 to Office Action Sep. 14, 2010", (w/ English Translation of Amended Claims), 16 pgs.
"Japanese Application Serial No. 2007-507458, Office Action mailed Aug. 31, 2010", (w/ English Translation), 4 pgs.
"Japanese Application Serial No. 2007-507458, Office Action Response Filed: Nov. 26, 2010", (w/ English Translation of amended claims), 6 pgs.
"Japanese Application Serial No. 2007-507465, Office Action mailed Sep. 1, 2010", (W/ English Translation), 4 pgs.
"Japanese Application Serial No. 2007-507465, Office Action Response Filed Nov. 24, 2010", (W/ English Translation of Amended Claims), 10 pgs.
"Japanese Application Serial No. 2007-525697, Office Action mailed Apr. 19, 2011", (w/ English Translation), 7 pgs.
"Japanese Application Serial No. 2007-525697, Office Action mailed Oct. 5, 2011", (w/ English translation), 5 pgs.
"Japanese Application Serial No. 2007-525697, Response filed Jun. 8, 2011 to Office Action mailed Apr. 19, 2011", (w/ English Translation of Amended Claims), 13 pgs.
"Japanese Application Serial No. 2007-525697, Response filed Dec. 9, 2011 to Office Action mailed Oct. 5, 2011", (w/ English translation of claims), 11 pgs.
Adams, J. T, "An introduction to IEEE Std 802.15.4", Aerospace conference, 2006 IEEE big sky, (Mar. 4-11, 2006), 1-8.
Bange, Joseph E, et al., "System and Method for RF Wake-Up of Implantable Medical Device", U.S. Appl. No. 11/101,142, filed Apr. 7, 2005, 19 pgs.
Crow, B P, et al., "Investigation of the IEEE 802.11 medium access control (MAC) sublayer functions", Proceedings IEEE INFOCOM '97. Sixteenth Annual Joint Conference of the IEEE Computer and Communications Societies, vol. 1, (1997), 126-133.
Duflot, M., et al., "A formal analysis of bluetooth device discovery", International journal on software tools for technology transfer, 8 (6), (Jul. 5, 2006), 621-632.
Guidant, "Feature Sheet and Specifications: Zoom Latitude", Doc. No. C3-194-1005, (2005), 2 pgs.
Guidant, "Go Beyond the Wand", Doc. No. C3-107-0505, (2005), 2 pgs.
Guidant, "Think Beyond the Wand", Doc. No. C3-101-0505, (2005), 3 pgs.
Guidant, "What if you could ZIP through implants and follow ups?", Doc. No. C3-117-0505, (2005), 2 pgs.
Guidant, "What if your patient develops diaphragmatic stimulation?", Doc. No. 03-116-0505, (2005), 2 pgs.
Harney, Austin, et al., "Wireless Short-Range Devices: Designing a Global License-Free System for Frequencies <1 GHz", Analog Dialogue 40-03, (Mar. 2006), 1 pg.
Healy, S. J., et al., "Cryptographic Authentication for Telemetry With an Implantable Medical Device", U.S. Appl. No. 10/801,070, filed Mar. 15, 2004, 38 pgs.
Zarlink Semiconductor, "Medical Implantable RF Transceiver", (2005), 40 pgs.
Zhu, H., et al., "A survey of quality of service in IEEE 802.11 Networks", IEEE Wireless Communications, IEEE Service Center, Piscataway, NJ, US, 11(4), (Aug. 2004), 6-14 pgs.
US 7,680,541, 03/2010, Von et al. (withdrawn)

\* cited by examiner

METHODS AND APPARATUSES FOR IMPLANTABLE MEDICAL DEVICE TELEMETRY POWER MANAGEMENT

CROSS-REFERENCE TO RELATED APPLICATIONS

This application is a division of U.S. patent application Ser. No. 12/684,303, now U.S. Pat. No. 8,538,528, filed on Jan. 8, 2010, which is a division of U.S. patent application Ser. No. 11/244,273, now U.S. Pat. No. 7,668,596, filed Oct. 5, 2005, which is a division of U.S. patent application Ser. No. 10/071, 255, now U.S. Pat. No. 6,985,773, filed on Feb. 7, 2002, the specifications of each of which are incorporated herein by reference in their entirety.

This application is related to co-pending, commonly assigned Von Arx et al. U.S. patent application Ser. No. 10/025,223, now U.S. Pat. No. 6,993,393, entitled "A TELEMETRY DUTY CYCLE MANAGEMENT SYSTEM FOR AN IMPLANTABLE MEDICAL DEVICE," filed Dec. 19, 2001 and Von Arx et al. U.S. patent application Ser. No. 10/025,183, entitled "AN IMPLANTABLE MEDICAL DEVICE WITH TWO OR MORE TELEMETRY SYSTEMS," filed Dec. 19, 2001, each of which is hereby incorporated by reference in its entirety.

TECHNICAL FIELD

This document relates generally to implantable medical devices and particularly, but not by way of limitation, to such a device including power management of a telemetry system allowing communication with an external device.

BACKGROUND

Medical devices are implanted in human bodies for monitoring physiological conditions, diagnosing diseases, treating diseases, or restoring functions of organs or tissues. Examples of such implantable medical devices include cardiac rhythm management systems, neurological stimulators, neuromuscular stimulators, and drug delivery systems. Because such a device may be implanted in a patient for a long time, the size and power consumption of the device are inherently constrained. Consequently, an implantable device may depend on an external system to perform certain functions. Communication between the implantable device and the external system is referred to as telemetry. Examples of specific telemetry functions include programming the implantable device to perform certain monitoring or therapeutic tasks, extracting an operational status of the implantable device, transmitting real-time physiological data acquired by the implantable device, and extracting physiological data acquired by and stored in the implantable device.

One particular example of implantable medical devices is a cardiac rhythm management device implanted in a patient to treat irregular or other abnormal cardiac rhythms by delivering electrical pulses to the patient's heart. Such rhythms result in diminished blood circulation. Implantable cardiac rhythm management devices include, among other things, pacemakers, also referred to as pacers. Pacers are often used to treat patients with bradyarrhythmias, that is, hearts that beat too slowly or irregularly. Such pacers may coordinate atrial and ventricular contractions to improve the heart's pumping efficiency. Implantable cardiac rhythm management devices also include devices providing cardiac resynchronization therapy (CRT), such as for patients with congestive heart failure (CHF). CHF patients have deteriorated heart muscles that display less contractility and cause poorly synchronized heart contraction patterns. By pacing multiple heart chambers or multiple sites within a single heart chamber, the CRT device restores a more synchronized contraction of the weakened heart muscle, thus increasing the heart's efficiency as a pump. Implantable cardiac management devices also include defibrillators that are capable of delivering higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias, that is, hearts that beat too quickly. In addition to pacers, CRT devices, and defibrillators, implantable cardiac rhythm management systems also include, among other things, pacer/defibrillators that combine the functions of pacers and defibrillators, drug delivery devices, and any other implantable systems or devices for diagnosing or treating cardiac arrhythmias.

Typically, an implantable cardiac rhythm management device communicates, via telemetry, with an external device referred to as a programmer. One type of such telemetry is based on inductive coupling between two closely-placed coils using the mutual inductance between these coils. This type of telemetry is referred to as inductive telemetry or near-field telemetry because the coils must typically be closely situated for obtaining inductively coupled communication. One example of such an inductive telemetry is discussed in Brockway et al., U.S. Pat. No. 4,562,841, entitled "PROGRAMMABLE MULTI-MODE CARDIAC PACEMAKER," assigned to Cardiac Pacemakers, Inc., the disclosure of which is incorporated herein by reference in its entirety.

In one example, an implantable device includes a first coil and a telemetry circuit, both sealed in a metal housing (referred to as a "can"). The external programmer provides a second coil in a wand that is electrically connected to the programmer. During device implantation, a physician evaluates the patient's condition, such as by using the implanted device to acquire real-time physiological data from the patient and communicating the physiological data in real-time to the external programmer for processing and/or display. The physician may also program the implantable device, including selecting a pacing or defibrillation therapy mode, and parameters required by that mode, based on the patient's condition and needs. The data acquisition and device programming are both performed using the inductive telemetry. If the patient's condition is stable after implantation, he or she needs no attention from the physician or other caregiver until a scheduled routine follow-up. During a typical routine follow-up, the physician reviews the patient's history with the implantable device, re-evaluates the patient's condition, and re-programs the implantable device if necessary.

One problem with inductive telemetry is its requirement that the two coils are closely placed. This typically requires placing the wand on the body surface over the implantable device. Because the wand is electrically connected to the programmer using a cable, the inductive telemetry limits the patient's mobility.

To improve communication range and patient mobility, a far-field radio-frequency (RF) telemetry may be used, in which an RF transceiver in the implantable device is used to communicate with an RF transceiver in the external programmer. With a far-field RF telemetry, the patient is typically free of any body surface attachment that limits mobility. However, RF telemetry may consume several thousand times more energy than inductive telemetry.

For these and other reasons, the present inventors have recognized an unmet need for long-range telemetry at reduced energy consumption from the implantable device.

SUMMARY

An implantable medical device includes a radio-frequency (RF) telemetry circuit that includes a power switch through which the RF telemetry circuit is connected to an energy source such as a battery. The power switch is closed to connect power from the energy source to the RF telemetry circuit when a user initiates an RF telemetry session. After the RF telemetry session is completed, the power switch is opened to shut off at least a portion of the RF telemetry circuit.

In one example, the RF telemetry circuit is powered on by sending a telemetry activation signal from the remote device to the implantable device. A physician or other caregiver operating the remote device initiates an RF telemetry session. The power switch is closed when the telemetry activation signal is detected by the implantable device.

In another example, the RF telemetry circuit is powered on by a physical movement sensed by an accelerometer and detected by the implantable device. A patient with the implantable device initiates an RF telemetry session by tapping on the skin over the implantable device. The power switch is closed when the implantable device detects an acceleration resulted from the tapping.

In another example, the RF telemetry circuit is powered on by activating an inductive telemetry circuit included in the implantable device. A physician or other caregiver operating an external programmer initiates an inductive telemetry operation in order to initiate an RF telemetry session. The power switch is closed when an inductive telemetry circuit in the implantable device is activated.

In another example, the RF telemetry circuit is powered on by a magnetic field detected by the implantable device. A physician or other caregiver waves a magnet or a hand held device generating a magnetic field to initiate an RF telemetry session. The power switch is closed when the magnetic filed exceeds a predetermined level and is detected by the implantable device.

In another example, the RF telemetry circuit is powered on by introducing a telemetry activation signal into the patient through a surface electrocardiography (ECG) recording system. A physician or other caregiver operating the remote device including an ECG module initiates an RF telemetry session. The power switch is closed when the telemetry activation signal is detected by a biopotential sensing circuit in the implantable device.

In another example, the RF telemetry circuit is powered on by introducing a telemetry activation signal into a patient through contacts between the patient and an external device adopted for telemetry activation. A patient initiates an RF telemetry session by contacting the external device. The power switch is closed when the telemetry activation signal is detected by a biopotential sensing circuit in the implantable device.

In one example, the RF telemetry circuit is shut off when a termination signal sent from the remote device through the RF telemetry is received by the implantable device. A physician or other caregiver operating the remote device may issue the termination signal. Alternatively, the termination signal may be sent when the remote device determines that the RF telemetry session is to be concluded. The power switch is opened when the implantable device receives the termination signal.

In another example, the RF telemetry circuit is shut off after a predetermined delay following an end of a data transmission session. A timer is started when the data transmission stops. The power switch is opened at the end of the predetermined delay if the data transmission has not resumed.

In another example, the RF telemetry circuit is shut off by activating an inductive telemetry circuit included in the implantable device. A physician or other caregiver operating an external programmer terminates an RF telemetry session. The power switch is closed immediately after the inductive telemetry circuit in the implantable device is activated.

Depending on a patient's needs for care and type of implantable device, one or more of the power-on methods and one or more of the power-off methods discussed in this document may be included in one implantable device. Using more than one method to connect/disconnect power from the energy source to the RF telemetry circuit increases the reliability of initiating and terminating the RF telemetry session in a timely manner to ensure patient safety and conserve energy and hence device longevity. Other aspects of the present systems, devices, and methods will become apparent upon reading the following Detailed Description and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, power management of telemetry circuit in an implantable medical device. The present methods and apparatuses will be described in applications involving implantable cardiac rhythm management systems such as pacemakers, CRT devices, cardioverter/defibrillators, and pacer/defibrillators. However, it is understood that the present methods and apparatuses may be employed in other types of implantable medical devices, including, but not being limited to, neurological stimulators, neuromuscular stimulators, drug delivery systems, and various types of physiological signal monitoring devices.

Figure 1:
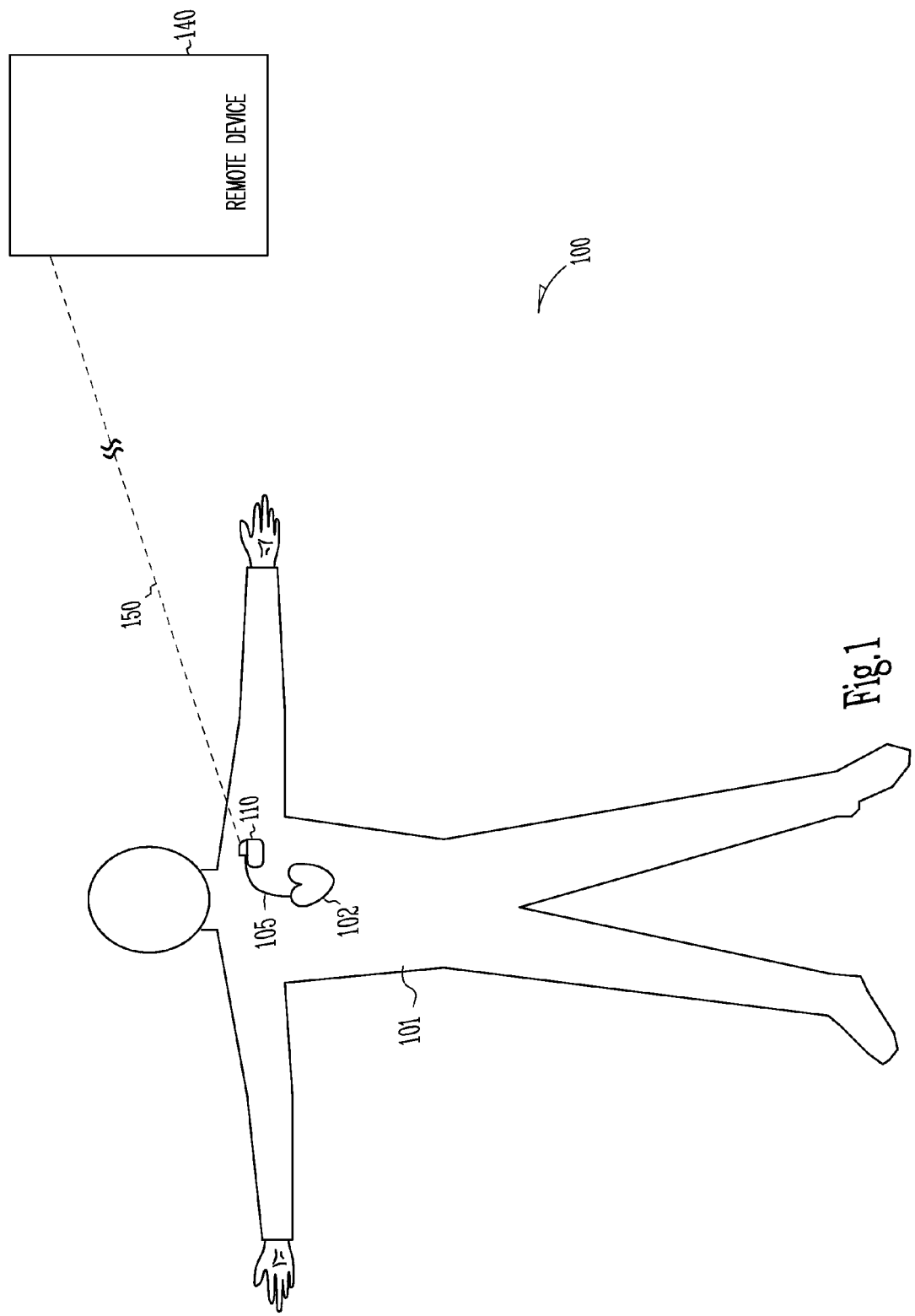
FIG. 1 is a schematic illustration of an example of portions of an implantable system 100 and portions of an environment in which it is used.

FIG. 1 is a schematic illustration of an example of portions of a medical system 100 and portions of an environment in which it is used. In this example, system 100 is a cardiac rhythm management system including, among other things, an implanted device 110 and a remote external device 140. Implanted device 110 is implanted within a patient's body 101 and coupled to the patient's heart 102 by a lead system 105. Examples of implanted device 110 include pacemakers, CRT devices, cardioverter/defibrillators, and pacer/defibrillators. Remote external device 140 provides a user interface for system 100. The user interface allows a physician or other caregiver to interact with implanted device 110 through a wireless telemetry link. In the example of FIG. 1, the wireless telemetry link is a radio-frequency (RF) telemetry link 150 supported by RF transceivers residing in implanted device 110 and external device 140. RF telemetry link 150 provides for bi-directional data communication between implanted device 110 and remote device 140.

In one example, RF telemetry link 150 provides for data transmission from implanted device 110 to remote device 140. This may include, for example, transmitting real-time physiological data acquired by implanted device 110, extracting physiological data acquired by and stored in implanted device 110, extracting therapy history data stored in implanted device 110, and extracting data indicating an operational status of implanted device 110 (e.g., battery status and lead impedance). In a further example, RF telemetry link 150 transmits data from remote device 140 to implanted device 110. This may include, for example, programming implanted device 110 to acquire physiological data, programming implanted device 110 to perform at least one self-diagnostic test (such as for a device operational status), and programming implanted device 110 to deliver at least one therapy.

In one example, RF telemetry link 150 is a far-field telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of RF telemetry link 150 (a distance over which data is capable of being wirelessly communicated) is at least six feet but can be as long as allowed by the particular communication technology. Unlike an inductive telemetry link using a wand placed near implanted device 110, typically attached to the patient, and electrically connected to remote external device 140 with a cable, using RF telemetry link 150 frees the patient from any physical restraints caused by the wand and the cable. On the other hand, the power consumed by implanted device 110 to support a far-field RF telemetry can be as high as ten thousand times that of inductive telemetry. To reduce the energy consumption of implanted device 110, the present inventors have recognized the need for power management to reduce the energy drawn from implanted device 110 to support the RF telemetry link 150.

Figure 2:
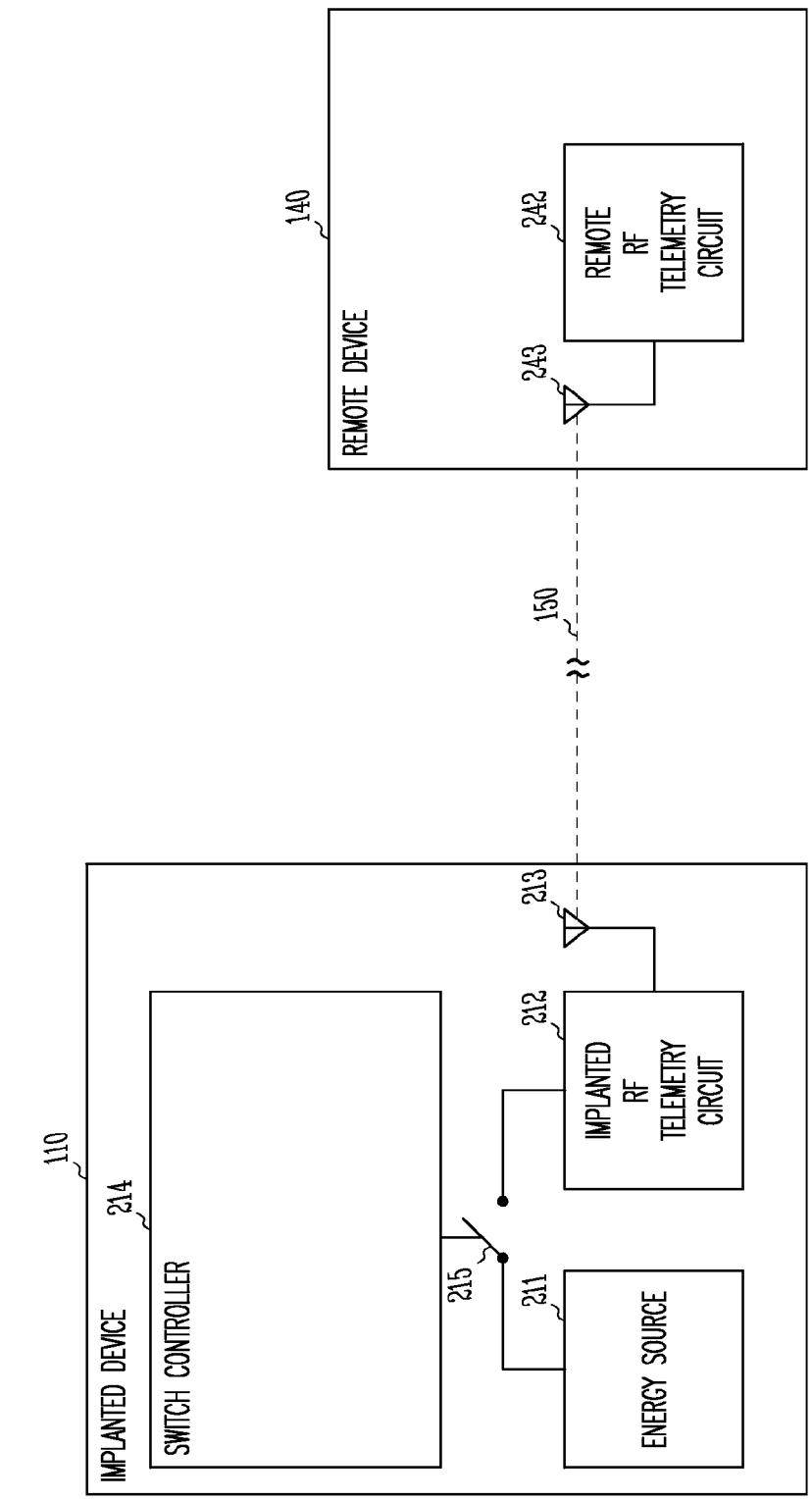
FIG. 2 is a schematic/block diagram illustrating one example of portions of a telemetry power management system for an implantable medical device.

FIG. 2 is a schematic/block diagram illustrating one example of portions of a telemetry power management system for implantable medical device. In this example, implantable medical system 100 includes implanted device 110, external remote device 140, and RF telemetry link 150. Remote device 140 includes a remote RF telemetry circuit 242 and a remote antenna 243. Implanted device 110 includes an energy source 211, an implanted RF telemetry circuit 212, an implanted antenna 213, and a switch controller 214. RF telemetry circuits 212 and 242, through antenna 213 and 243, respectively, communicate using RF telemetry link 150. A power switch 215, when closed, connects implanted RF telemetry circuit 212 to energy source 211 to draw energy therefrom. In many applications of system 100, data is being transmitted for a small fraction of the time when implanted device 110 is in use. Therefore, RF telemetry circuit 212 only needs to be powered during a data transmission (and for a short preceding power-up period). In this example, an output of switch controller 214 drives power switch 215. Switch controller 214 closes power switch 215 when implantable RF telemetry circuit 212 is powered to support the data transmission over RF telemetry link 150 and opens power switch 215 shortly after the data transmission is completed. This document presents several specific illustrative examples of controlling the power-on and power-off status of RF telemetry circuit 212, such as by closing and opening power switch 215, respectively. The examples can be combined in any way.

In this document, "power switch" refers generally to any power connection module, not limited to an on/off switch, that, in one example controls an activation (or power-on) and deactivation (or power-off) of the RF telemetry. In one example, the RF telemetry circuit is powered on, or activated, when it enters an energization state that enables it to perform its intended telemetry function. In another example, the RF telemetry circuit is powered off, or deactivated, when it enters another energizaton state that maintains the circuit off or in a "sleep" or "barely awake" mode to conserve energy. In one example, the power switch connects/disconnects power from the energy source to one or more portions of the RF telemetry circuit.

In one example, power switch 215 connects/disconnects power from energy source 211 to portions of RF telemetry circuit 212. After the telemetry session is terminated, power switch 215 disconnects power from the portions of RF telemetry circuit 212 but maintains power connection to other portions of RF telemetry circuit 212, such that RF telemetry circuit 212 may be activated quickly when a new telemetry session is initiated.

Example of Power-on by Using a Low-Power Radio Receiver

Figure 3A:
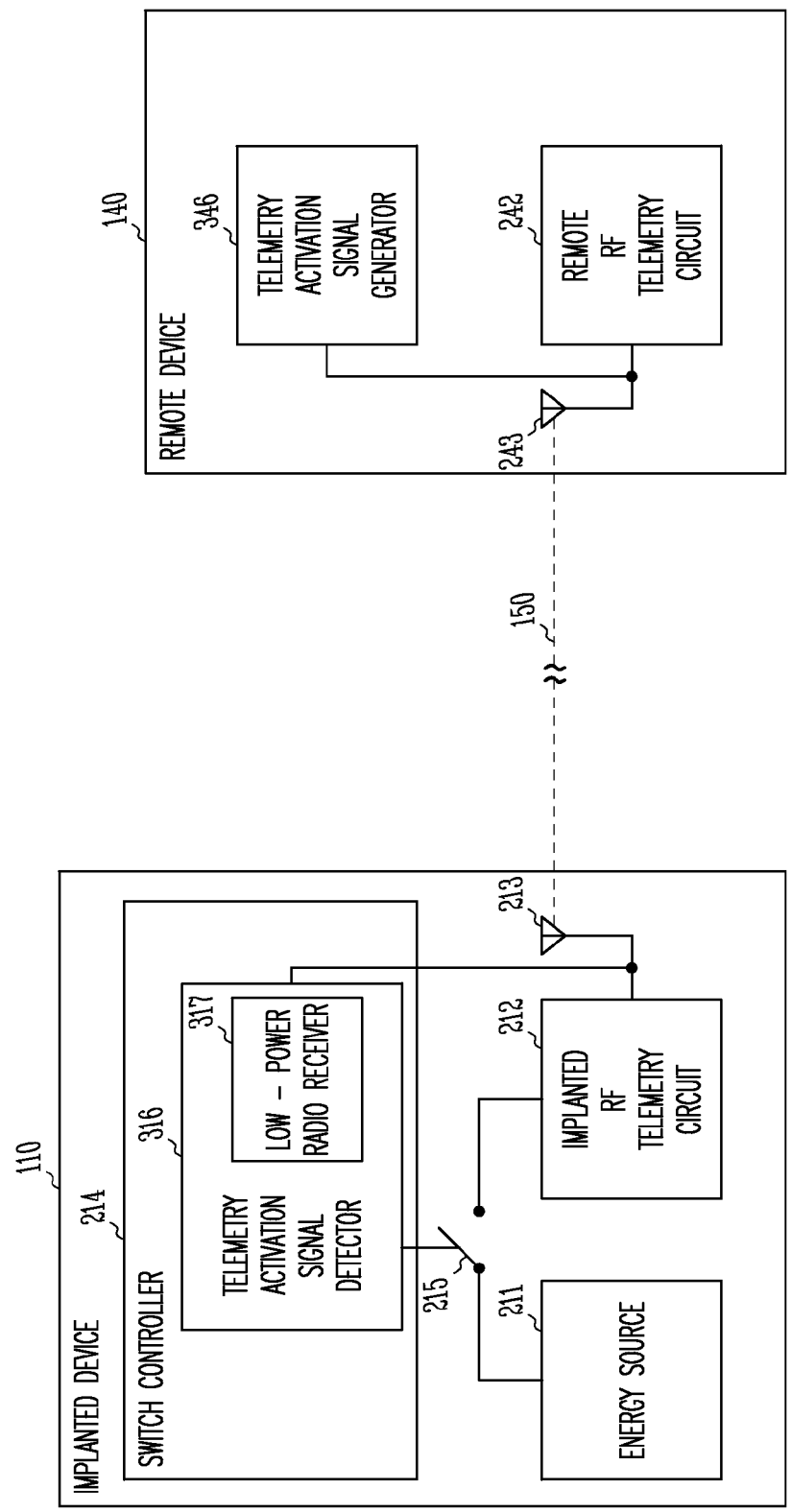
FIG. 3A is a schematic/block diagram illustrating one example of portions of a telemetry power management system controlling power-on by using a telemetry activation signal detector including a low power radio receiver.

FIG. 3A is a schematic/block diagram illustrating one example of portions of a telemetry power management system controlling power-on of at least a portion of the telemetry. In this example, power switch 215 is closed to connect power from energy source 211 to implanted RF telemetry circuit 212 when implanted device 110 receives an radio signal. Remote device 140 includes a telemetry activation signal generator 346 coupled to remote antenna 243. Switch controller 214 includes a telemetry activation signal detector 316 coupled to implanted antenna 213. Telemetry activation signal detector 316 includes a low power radio receiver 317. Low power radio receiver 317 is always awake to respond to telemetry activation signals. To initiate a data transmission over RF telemetry link 150, a telemetry activation signal is generated by telemetry activation signal generator 346 and emitted through remote antenna 243. Upon receiving the telemetry activation signal through implanted antenna 213, telemetry activation signal detector 316 closes power switch 215 to operate implanted RF telemetry circuit 212. The telemetry activation signal is a radio signal having an amplitude and frequency in compliance with applicable government regulations. In one example, the telemetry activation signal is a high-power RF burst signal.

Figure 3B:
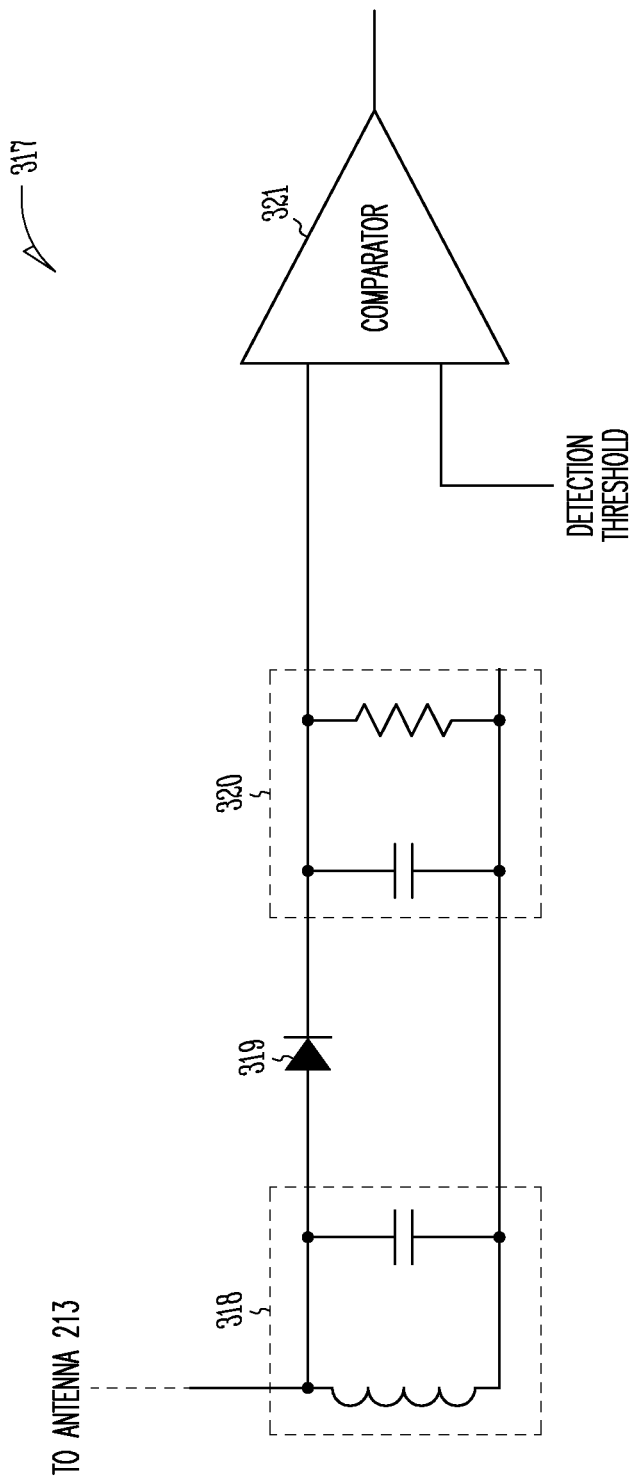
FIG. 3B is a schematic illustrating one example of the low power radio receiver.

FIG. 3B is a schematic illustrating one example of low power radio receiver 317. Low power radio receiver includes a tank circuit 318, a diode 319, a low-pass filter 320, and a low-power comparator 321. Tank circuit, coupled to antenna 213 to receive a signal including the telemetry activation signal, includes an inductor and a capacitor to form a high-Q resonant circuit that obtains a gain passively. Diode 319 is a non-linear element for rectifying the received signal. Low pass filter 320 includes a resistor and a capacitor to detect an envelope of the rectified signal. Low power comparator generates an output indicating a detection of the telemetry activation signal when at least a portion of the envelope exceed a predetermined detection threshold. In one example, low power radio receiver operates with a supply current of approximately 100 nA-500 nA.

Figure 4:
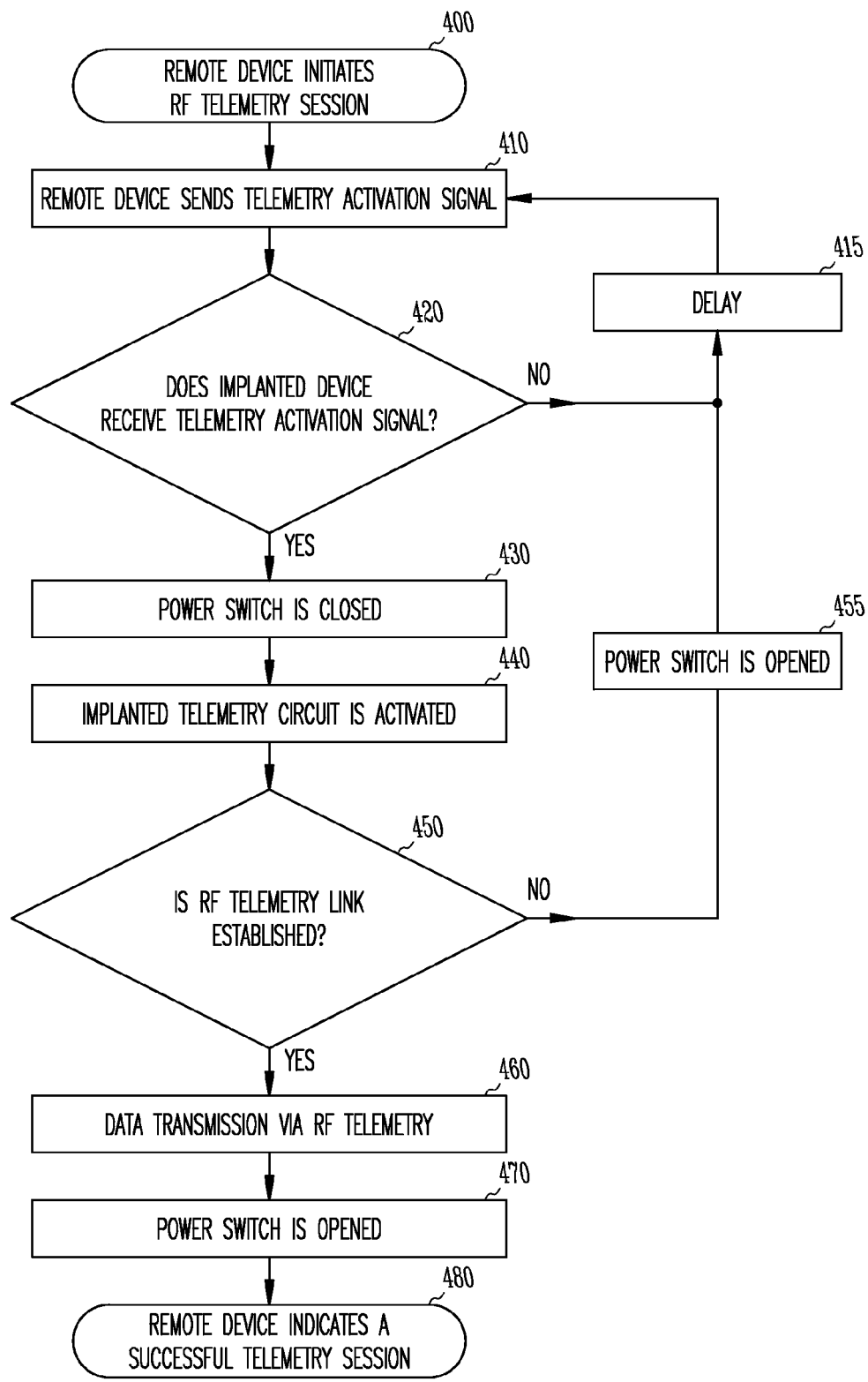
FIG. 4 is a flow chart illustrating one example of a method corresponding to the example of FIG. 3A.

FIG. 4 is a flow chart illustrating one example of a method corresponding to the example of FIG. 3A. At 400, an RF telemetry session is initiated at remote device 140. In one example, the RF telemetry session is initiated by a physician or other caregiver. In another example, the RF telemetry session is initiated automatically by remote device 140, e.g., occasionally or periodically. In one example, the RF telemetry session is initiated for a regular check-up of a status of the device and conditions of the patient in whom the device is implanted. In one example, the RF telemetry session is initiated in response to a phone from a person, such as a caregiver or the patient, regarding a condition of the patient that needs immediate attention. At 410, remote device 140 sends out a telemetry activation signal. The telemetry activation signal is a radio signal having an amplitude and frequency in compliance with applicable government regulations. In one example, the telemetry activation signal is an RF burst. In a further example, the RF burst has a duration of up to five milliseconds and an amplitude sufficient to be received by implanted RF telemetry circuit 212 up to a predetermined distance from remote device 140. Typically, the RF burst received at implanted RF telemetry circuit 212 has an amplitude of at least 1 mV. In one example, the RF burst amplitude used is determined based on an environmental noise and a signal-to-noise ratio that ensures reliable detection by diode detector 317. In one example, remote device sends a digital key that follows the telemetry activation signal. The digital key is a coded signal identifying a particular implantable device 110. If the telemetry activation signal is received by at least one implanted device 110 within the predetermined distance from remote device 140, power switch 215 in that particular implanted device 110 is closed at 430 for connecting RF telemetry circuit 212 and energy source 211 of that implanted device 110. At 440, telemetry device is activated to perform RF telemetry functions. At 450, if the particular implanted device 110 receives the digital key matching its identification code, it sends a responsive signal to remote device 140. In one example, implanted device 110 is prevented from sending out any signal after an end of the RF telemetry session until a matched digital key is received at the beginning of a new RF telemetry session. The reception of this responsive signal by remote device 140 indicates that RF telemetry has been successfully established, i.e., RF telemetry link 150 is ready for bi-directional data transmission. If the identification code fails to match the identification of the particular implanted device 110, its power switch 215 is opened at 455, and remote device 140 repeats the process at 410 after a predetermined delay 415. After the RF telemetry is established at 450, data is transmitted from remote device 140 to implanted device 110 and/or from implanted device 110 to remote device 140 at 460. The RF telemetry enters an idle state following an end of the RF telemetry session, when RF telemetry circuit 212 is powered but no data is being transmitted between implanted device 110 and remote device 140. After the RF telemetry enters an idle state, power switch 215 is opened at 470 to disconnect power to at least a portion of RF telemetry circuit 212. Examples of methods and apparatus controlling the opening of power switch 215 are described later in this document. At 480, remote device 140 indicates whether the telemetry session was successful, such as by logging or displaying a message.

Example of Power-on by Physical Motion

Figure 5:
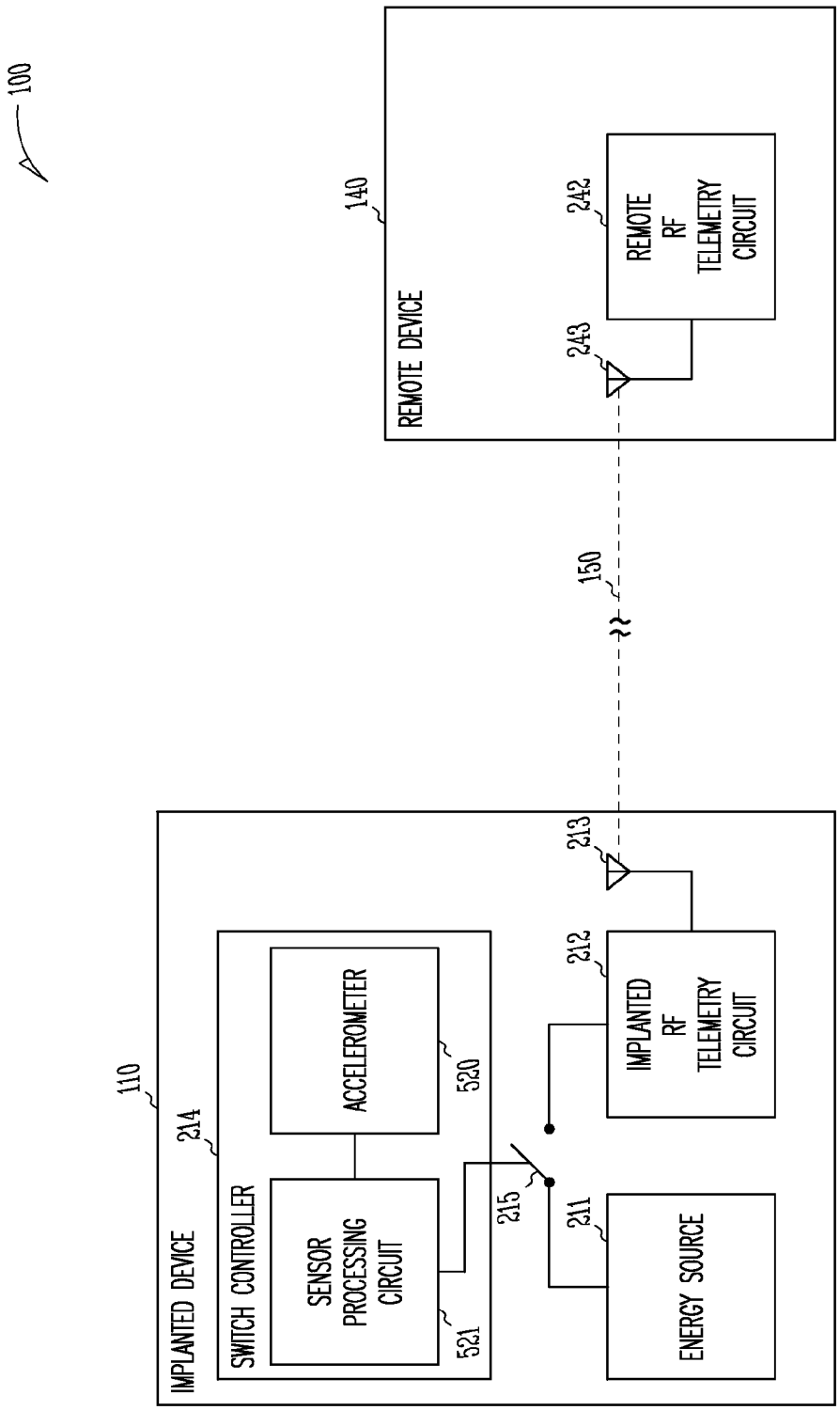
FIG. 5 is a schematic/block diagram illustrating one example of portions of a telemetry power management system controlling power-on by detecting a physical activity.

FIG. 5 is a schematic/block diagram illustrating another example of portions of a telemetry power management system controlling power-on of at least a portion of the telemetry. In this example, power switch 215 is closed to connect power from energy source 211 to RF telemetry circuit 212 when a patient activity (e.g., a body motion) of a predetermined magnitude, duration, and/or pattern is detected. In this example, switch controller 214 includes accelerometer 520 and a sensor signal processing circuit 521. Accelerometer 520 senses acceleration of implanted device 110, resulted from body motion of the patient. In one example, sensor processing circuit 521 includes an amplifier and a filter to condition the activity signal sensed by accelerometer 520 and a comparator to compare the conditioned acceleration signal to a predetermined acceleration threshold. If the conditioned acceleration signal exceeds the predetermined acceleration threshold, sensor processing circuit 521 outputs a signal to close power switch 215. In an additional example, sensor processing circuit 521 further includes a pattern recognition module to detect a predetermined pattern of acceleration. One example of such pattern of acceleration includes three momentary acceleration impulses that are about one second apart from each other and all exceed the predetermined acceleration threshold.

Figure 6:
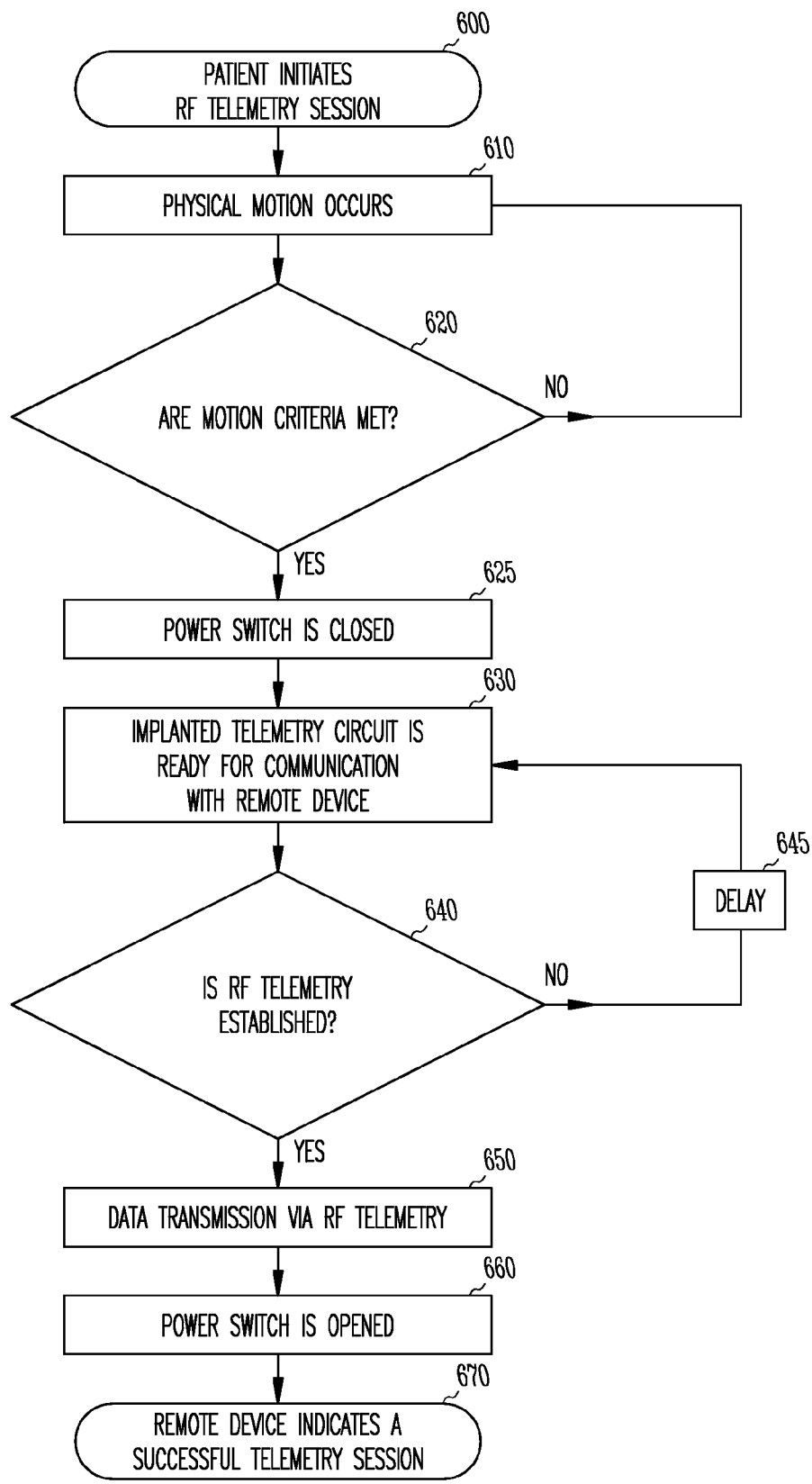
FIG. 6 is a flow chart illustrating one example of a method corresponding to the example of FIG. 5.

FIG. 6 is a flow chart illustrating one example of a method corresponding to the example of FIG. 5. At 600, a physical movement of the patient in whom implanted device 110 is implanted initiates an RF telemetry session. In one example, the patient initiates an RF telemetry session to inform or alert a physician or caregiver of his recent or present condition. To initiate the telemetry operation at 610, the patient taps on his/her skin over implanted device 110. The movement resulted from the tapping is sensed by accelerometer 520. If the tapping results in an acceleration that exceeds a predetermined threshold acceleration level at 620, sensor processing circuit 521 outputs a signal that closes power switch 215 at 625. If the acceleration is below the threshold, the tapping does not initiate an RF telemetry session. In another example, in addition to requiring that acceleration exceeds a predetermined threshold acceleration level, the tapping activity must also exhibit a predetermined pattern, and sensor processing circuit 521 outputs a signal to close power switch 215 at 625. One suitable predetermined pattern of movement results from tapping on the skin over the device three times in approximately one-second intervals. At 630, just after switch 215 is closed, RF telemetry circuit 212 is activated and ready for bi-directional communication with remote device 140 via RF telemetry link 150. In one example, RF telemetry circuit 212 sends out a signal to remote device 140 to establish RF telemetry. If the signal is received by remote device 140, and remote device 140 is available for communication, remote device 140 sends a response signal back to implanted device 110, and the RF telemetry is established at 640. If the RF telemetry cannot be established, because, for example, there is no available remote device 140 within the RF telemetry range, implanted RF telemetry circuit 212 will repeat 630 after a predetermined delay 645. In one example, delay 645 is a programmable constant. A suitable range of this constant is 0.5 to 2 seconds. In another example, delay 645 is a function of the number of unsuccessful attempts to establish the RF telemetry. This function represents a particular sequence of successive attempts to establish the RF telemetry. For example, if the first attempt fails, the next five attempts may be made in about one-minute intervals. If the RF telemetry is still not established, further attempts may be made in about 30-minute intervals. Other examples of successive attempts may include a time interval between consecutive attempts that increases linearly or exponentially. In another example, remote device 140 occasionally or periodically sends a signal including a digital key identifying a particular implantable device 110. In response to receiving this signal, RF telemetry circuit 212 sends out a signal to remote device 140 to establish RF telemetry at 640. In this example, implantable device 110 is prevented from starting RF telemetry communications without an authorization from remote device 140. Thus, implant device 110 need not make repeated attempts to establish RF telemetry, thereby saving energy. This also prevents the situation in which multiple implantable devices compete to establish RF telemetry with one remote device 140 by giving remote device 140 the control over which particular implantable device 110 to communicate with. Furthermore, preventing implantable device 110 from initiating signal transmission ensures that implantable device 110 does not accidentally sent RF signals in violation of applicable government regulations when the patient travels to a different country. After the RF telemetry is established at 640, data is transmitted from remote device 140 to implanted device 110 and/or from implanted device 110 to remote device 140 at 650. After the RF telemetry enters an idle state, power switch 215 is opened at 660 to disconnect power from energy source 211 to at least a portion of RF telemetry circuit 212. Examples of methods and apparatus controlling the opening of power switch 215 are described later in this document. At 670, remote device 140 indicates whether the telemetry session was successful, such as by logging or displaying a message.

Example of Power-on by Activating Inductive Telemetry

Figure 7:
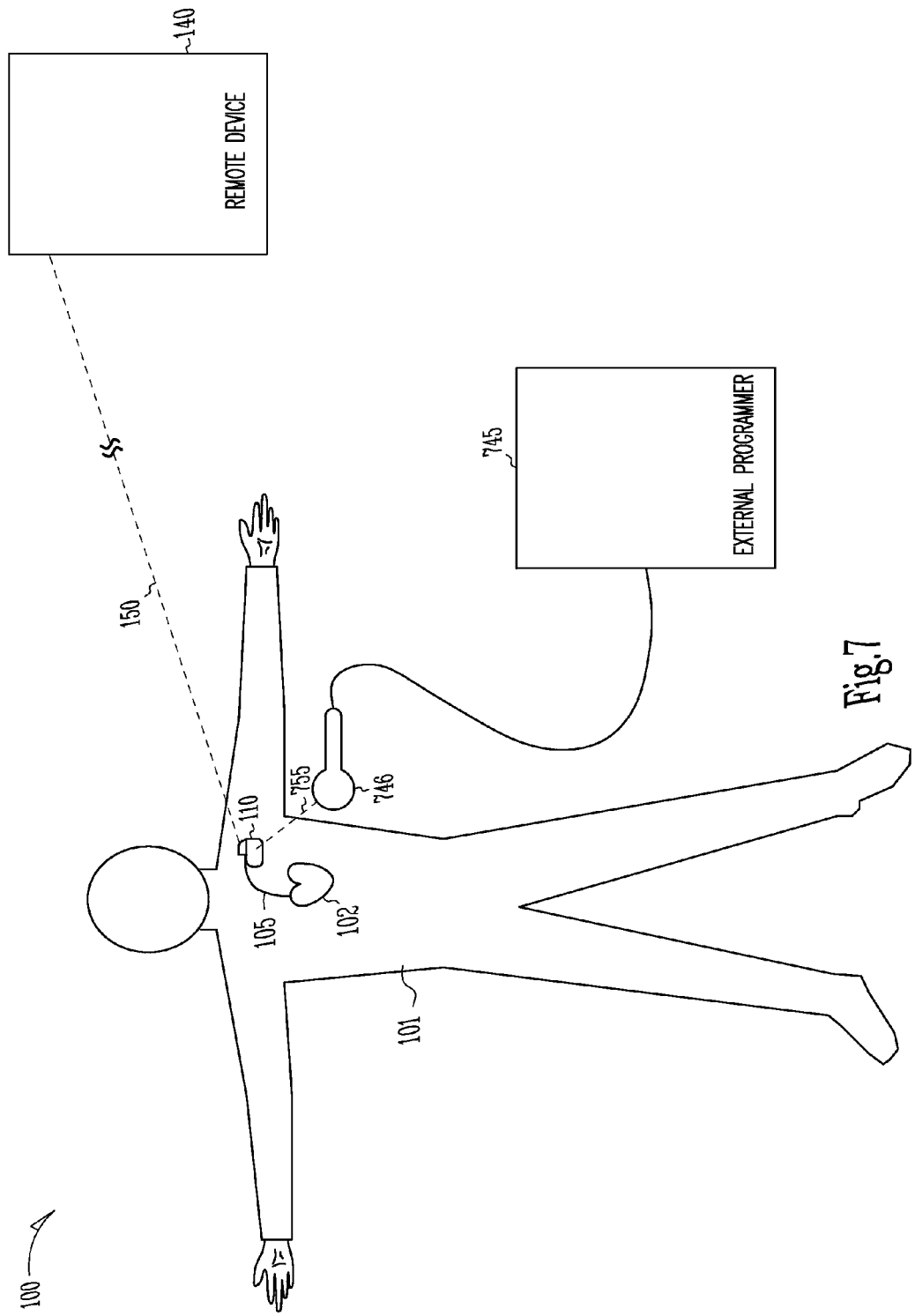
FIG. 7 is a schematic illustration of one example of portions of a telemetry power management system controlling power-on by activating inductive telemetry.

FIG. 7 is a schematic illustration of another example of portions of a telemetry power management system controlling power-on of at least a portion of the telemetry. In this example, system 100 includes an additional remote device, such as an external programmer 745. External programmer 745 and implanted device 110 include respective circuits providing an inductive telemetry link 755. Inductive telemetry link 755 uses mutual inductance between two closely placed coils, one at implanted device 110 and the other carried by a wand 746. Wand 746 is coupled to the external programmer 745 via a cable. When wand 746 is in place to form an adequate mutual inductance between the coils, external programmer 745 sends implanted device 110 a synchronization signal to establish inductive telemetry link 755. The establishment of inductive telemetry link 755 initiates the process of establishing the RF telemetry session. This process includes that the implanted device 110 powers up its RF telemetry circuit and sends a signal to remote device 140. The RF telemetry is established when implanted device 110 receives a response signal from remote device 140. In one example, remote device 140 and programmer 745 are physically integrated into one single device.

Figure 8:
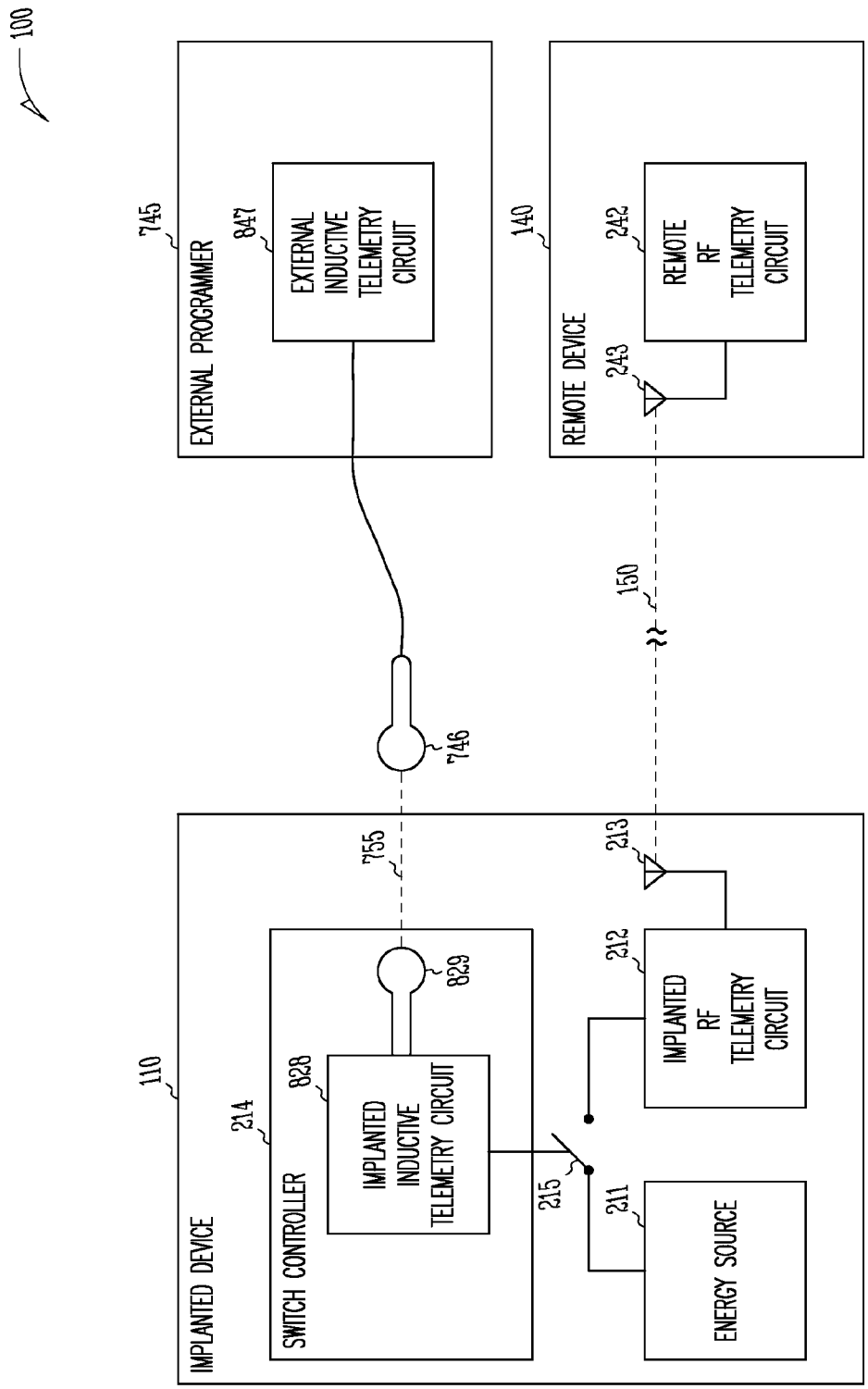
FIG. 8 is a schematic/block diagram illustrating one example of portions of a telemetry power management system corresponding to the example of FIG. 7.

FIG. 8 is a schematic/block diagram illustrating one example of portions of a telemetry power management system corresponding to the example of FIG. 7. In this example, system 100 includes implanted device 110, remote device 140, and external programmer 745. In one example, remote device 140 and programmer 745 are physically integrated into one single device. Implanted device 110 communicates with remote device 140 via RF telemetry link 150, or with external programmer 745 via inductive telemetry link 755. External programmer 745 includes an external inductive telemetry circuit 847. Switch controller 214 in implanted device 110 includes an implantable inductive telemetry circuit 828 including an output that controls power switch 215. Inductive telemetry link 755 uses mutual inductance between coil 829 and another coil in wand 746. The coil in wand 746 is electrically connected to external inductive telemetry circuit 847. Switch 215 is closed to connect power from energy source 211 to RF telemetry circuit 212 after implanted inductive telemetry circuit 828 becomes active, i.e., after inductive telemetry link 755 is ready for bi-directional data communication. The inductive telemetry need not remain active after the RF telemetry is established.

Figure 9:
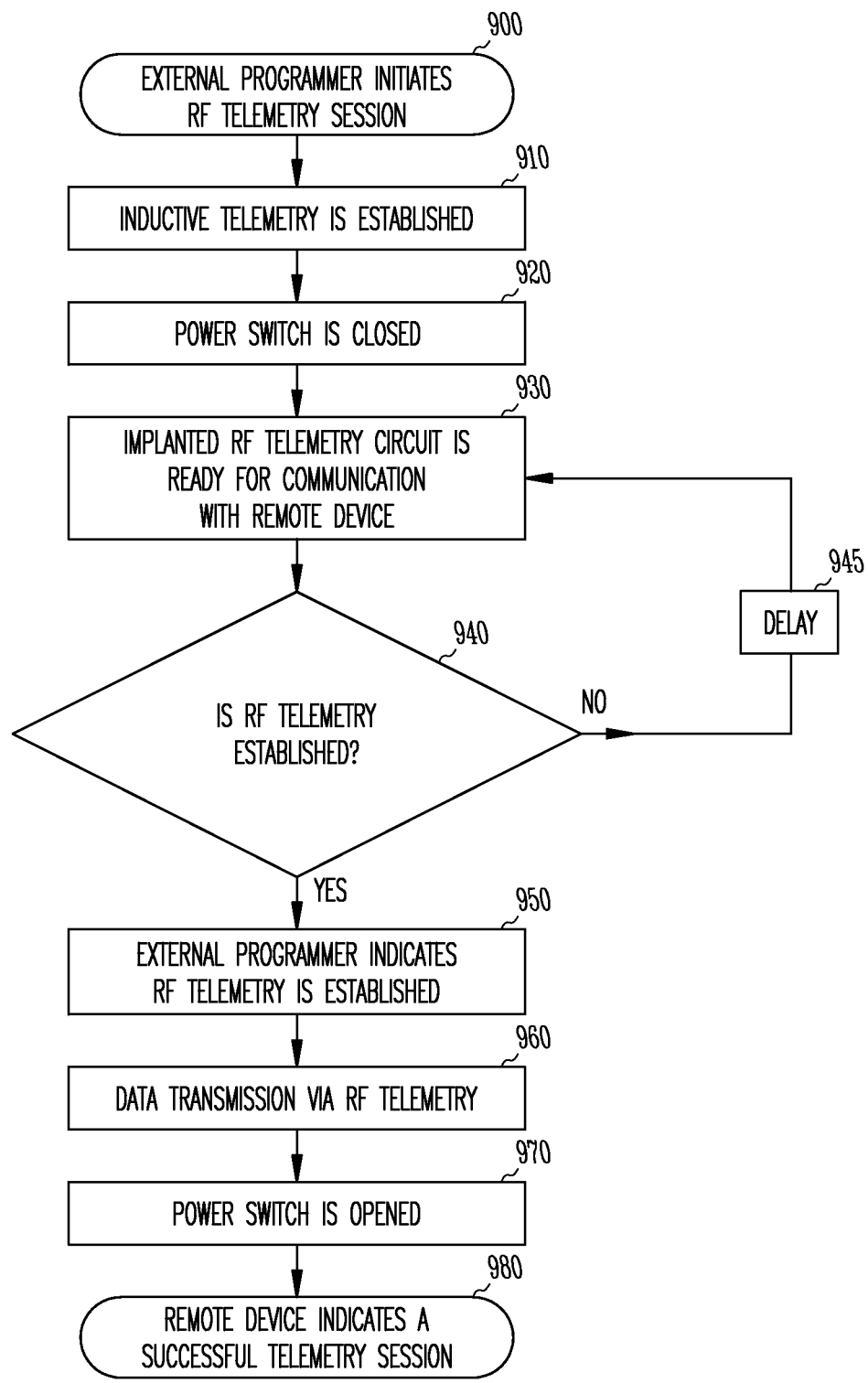
FIG. 9 is a flow chart illustrating one example of a method corresponding to the example of FIG. 8.

FIG. 9 is a flow chart illustrating one example of a method corresponding to the example of FIG. 8. At 900, a physician or other caregiver initiates an RF telemetry session by placing or waving wand 746 near implanted device 110. In one example, the RF telemetry session is initiated for evaluating a patient's condition, and RF telemetry provides patient mobility after wand 746 is removed. In another example, the RF telemetry session is initiated just before implanted device 110 is implanted in a patient. The RF telemetry avoids bringing wand 746 into the sterile field of the operation. At 910, inductive telemetry link 755 is established. External programmer 745 indicates whether inductive telemetry link 755 was successfully established. If establishment of inductive telemetry link 755 was unsuccessful, the physician or other caregiver adjusts the position of wand 746 until such success is obtained. In one example, external programmer 745 sends a synchronization signal to implanted device 110. Upon receiving the synchronization signal, implanted inductive telemetry circuit 828 sends a return signal back to external programmer 745, and inductive link 755 is established at 910 when external inductive telemetry circuit 847 receives the return signal. At 920, power switch 215 is closed to connect power from energy source 211 to implanted RF telemetry circuit 212. At 930, RF telemetry circuit 212 is activated and ready for bi-directional communication with remote device 140 via RF telemetry link 150. In one example, implanted RF telemetry circuit 212 sends a signal to remote device 140. If the signal is received by remote device 140, and remote device 140 is not busy with ongoing telemetry with other implantable device(s), remote device 140 sends a responsive signal back to implanted device 110, and the RF telemetry is established at 940. If the RF telemetry cannot be established at 940, because, for example, there is no available remote device 140 within the RF telemetry range, RF telemetry circuit 212 will repeat 930 after a delay 945. In one example, delay 945 is a programmed constant. In another example, delay 945 is a function of the number of unsuccessful attempts to establish the RF telemetry. This function represents a particular sequence of successive attempts to establish the RF telemetry. In another example, remote device 140 periodically sends a signal including a digital key identifying a particular implantable device 110. Only upon receiving this signal, RF telemetry circuit 212 sends out a signal to remote device 140 to establish RF telemetry at 940. At 950, external programmer 745 indicates whether RF telemetry link 150 has been established. In one example, the physician or caregiver may then remove wand 746 from near implanted device 110 at 950, leaving the patient free of cable attachment. In another example, the physician or caregiver must remove wand 746 from near implanted device 110 at 950 before the RF telemetry can be established because the inductive telemetry is given priority over the RF telemetry. At 960, data is transmitted from remote device 140 to implanted device 110 and/or from implanted device 110 to remote device 140. After the RF telemetry enters an idle state, power switch 215 is opened at 970 to disconnect power from energy source 211 to at least a portion of RF telemetry circuit 212. Examples of methods and apparatuses controlling the opening of power switch 215 are described later in this document. At 980, remote device 140 indicates whether the telemetry session was successful, such as by logging or displaying a message.

Example of Power-on by Magnetic Field

Figure 10:
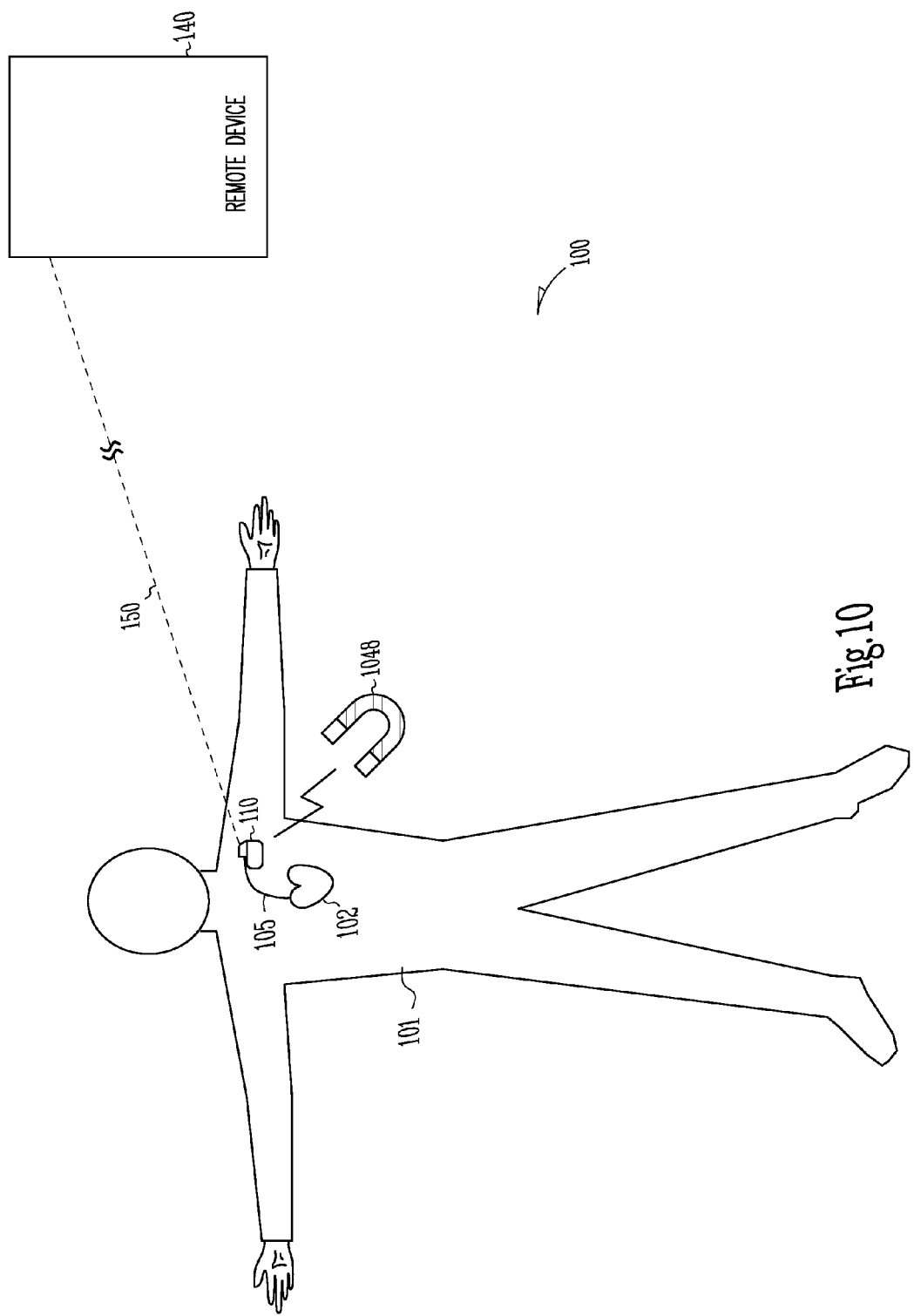
FIG. 10 is a schematic illustration of one example of portions of a telemetry power management system controlling power-on by creating a magnetic field near the implantable medical device.

FIG. 10 is a schematic illustration of another example of portions of a telemetry power management system controlling power-on of at least a portion of the telemetry. In this example, system 100 includes a magnetic field provider 1048. The RF telemetry session is initiated when implanted device 110 detects a magnet field. In one example, magnetic field provider 1048 includes a permanent magnet. In another example, magnetic field provider 1048 includes a hand-held, battery-powered magnetic field provider, such as a wireless, battery operated inductive wand. In another example, magnetic field provider 1048 is an external programmer including an inductive telemetry circuit or other circuit or other device generating a magnetic field.

Figure 11:
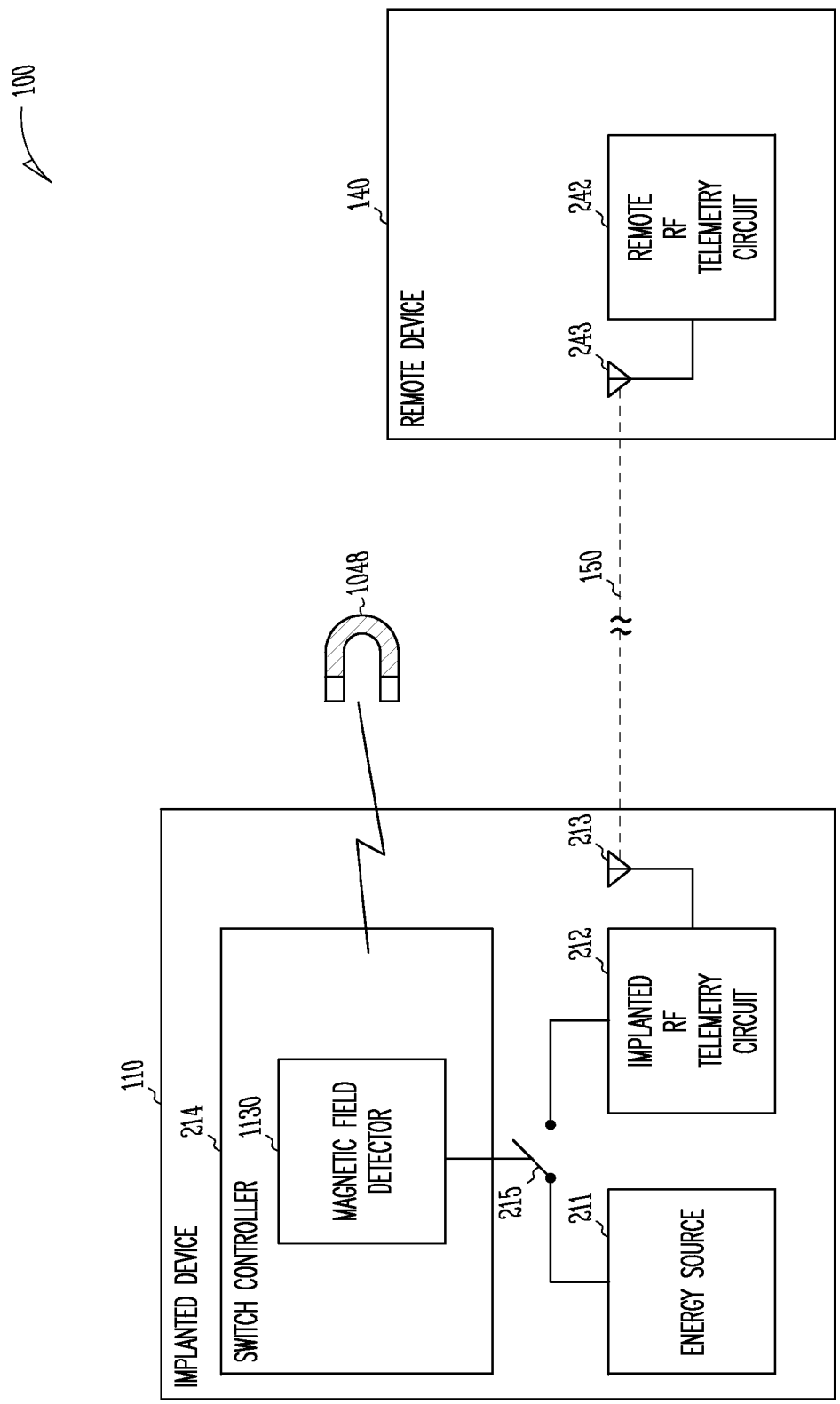
FIG. 11 is a schematic/block diagram illustrating one example of portions of a telemetry power management system corresponding to the example of FIG. 10.

FIG. 11 is a schematic/block diagram illustrating one example of portions of a telemetry power management system corresponding to the example of FIG. 10. In this example, system 100 includes implanted device 110, remote device 140, and magnetic field provider 1048. Switch controller 214 in implanted device 110 includes a reed switch or other magnetic field detector 1130 that controls power switch 215. Power switch 215 is closed to connect power from energy source 211 to RF telemetry circuit 212 when a magnetic field is detected by magnetic field detector 1130 exceeds a threshold.

Figure 12:
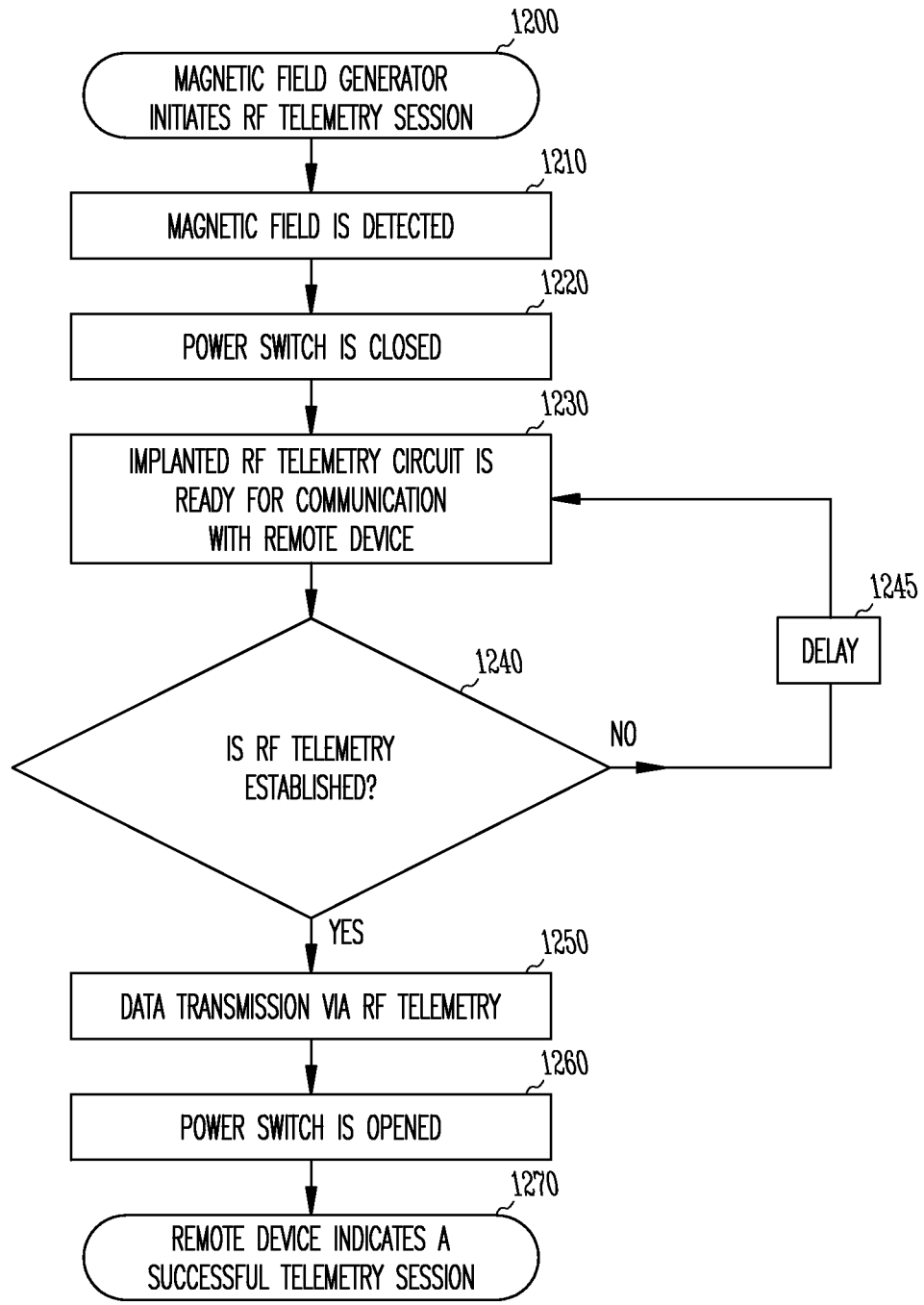
FIG. 12 is a flow chart illustrating one example of a method corresponding to the example of FIG. 11.

FIG. 12 is a flow chart illustrating one example of a method corresponding to the example of FIG. 11. At 1200, a physician or other caregiver initiates an RF telemetry session by momentarily waving magnetic field provider 1048 near implanted device 110. In one example, the RF telemetry session allows evaluation of a patient's condition while providing patient mobility. At 1210, the magnetic field from magnetic field provider 1048 is detected by magnetic field detector 1130 when the field strength exceeds a threshold level. In response, at 1220, power switch 215 is closed to connect power from energy source 211 to implanted RF telemetry circuit 212. At 1230, RF telemetry circuit 212 is activated and ready for bi-directional communication with remote device 140 via RF telemetry link 150. In one example, implanted RF telemetry circuit 212 sends a signal to remote device 140. If the signal is received by remote device 140, and remote device 140 is not busy communicating with other implantable device(s), remote device 140 sends a responsive signal back to implanted device 110, establishing RF telemetry at 1240. If the RF telemetry cannot be established at 1240, because, for example, there is no available remote device 140 within the RF telemetry range, RF telemetry circuit 212 will repeat 1230 after a delay 1245. In one example, delay 1245 is a programmed constant. In another example, delay 1245 is a function of the number of unsuccessful attempts to establish the RF telemetry. This function represents a particular sequence of successive attempts to establish the RF telemetry. In another example, remote device 140 periodically sends a signal including a digital key identifying a particular implantable device 110. Only upon receiving this signal, RF telemetry circuit 212 sends out a signal to remote device 140 to establish RF telemetry at 1240. At 1250, data is transmitted from remote device 140 to implanted device 110 and/or from implanted device 110 to remote device 140. After the RF telemetry enters an idle state, power switch 215 is opened at 1260 to disconnect power from energy source 211 to at least a portion of RF telemetry circuit 212. Examples of methods and apparatus controlling the opening of power switch 215 are described later in this document. At 1270, remote device 140 indicates whether the telemetry session was successful, such as by logging or displaying a message.

Example of Power-on by Using Signal Introduced Via Surface ECG Electrodes

Figure 13:
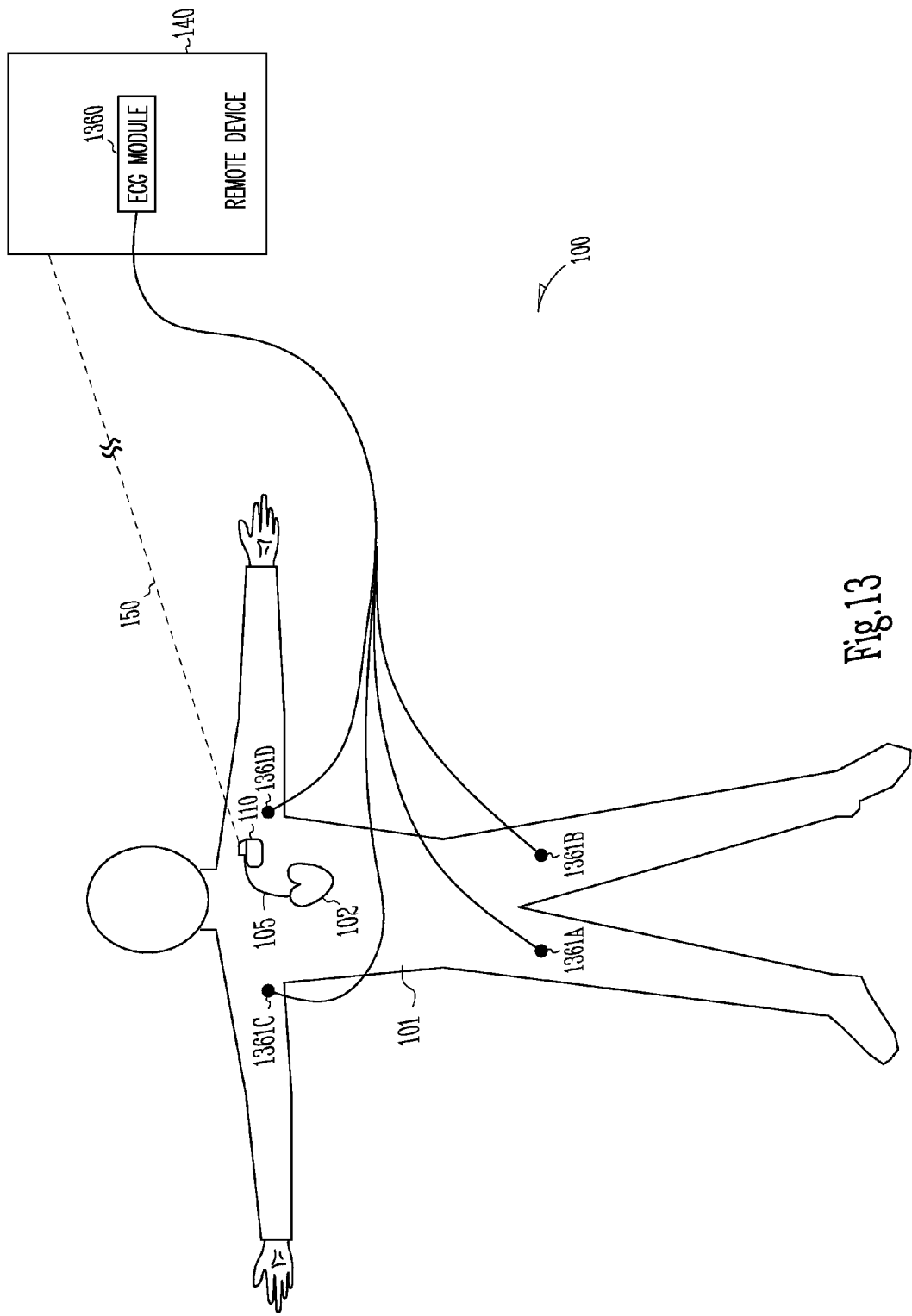
FIG. 13 is a schematic illustration of one example of portions of a telemetry power management system controlling power-on by introducing a signal through an electrocardiograph (ECG) system.

FIG. 13 is a schematic illustration of another example of portions of a telemetry power management system controlling power-on of at least a portion of the telemetry by using an electrocardiograph (ECG) monitoring or recording system. In this example, remote device 140 includes an ECG monitoring or recording module 1360. In one example, ECG module 1360 is used for assessing the behavior of implanted device 110 by observing the cardiac signals, such as through surface electrodes 1361A-D attached to a patient's skin. Once electrodes 1361A-D are electrically coupled to ECG module 1360, a low-amplitude electrical current signal is sent to the body from remote device 140, through two or more of electrodes 1361. This current signal is sensed by implanted device 110 as a telemetry power-on signal. In one example, the low-amplitude electrical current signal includes an encoded command that can be easily distinguished from noise that may be present on electrodes 1361. Once RF telemetry link 150 has been established, electrodes 1361 need not remain attached during the subsequent telemetry session.

Figure 14:
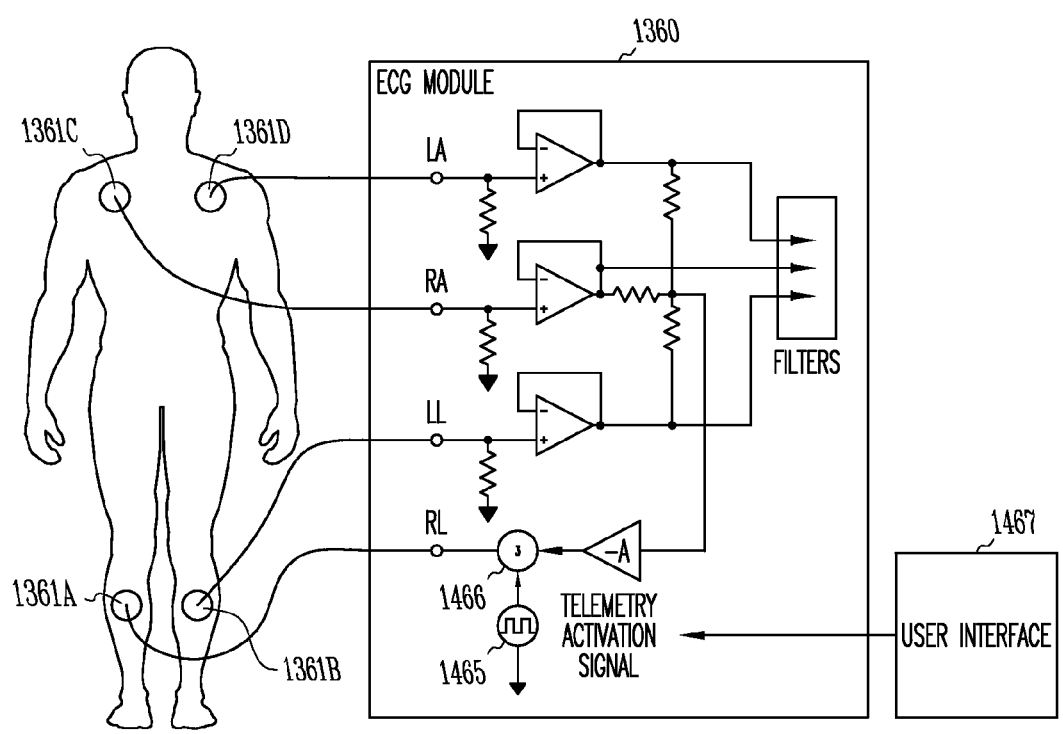
FIG. 14 is a circuit diagram illustrating one example of portions of the telemetry power management system of FIG. 13.

FIG. 14 is a circuit diagram illustrating one example of portions of the telemetry power management system of FIG. 13. In this example, ECG module 1360 is coupled to electrodes 1361, including three input electrodes 1361B-D and one right-leg negative feedback electrode 1351A. Right-leg negative feedback is a technique known in the art of ECG monitoring or recording for reducing noise pickup due to a common-mode voltage on electrodes 1361B-D while increasing patient safety. ECG module 1360 includes a telemetry activation signal generator 1465 and a signal summing circuit 1466. In one example, a physician or other caregiver initiates an RF telemetry session by providing an input at a user interface 1467. This input causes signal generator 1465 to issue a telemetry activation signal. In another example, signal generator 1465 automatically issues a telemetry activation signal upon a predetermined event. This signal is summed into the negative feedback circuit and introduced into the patient's body via electrode 1361A. In one example, the telemetry activation signal has a frequency much greater than 150 Hz. This allows the telemetry activation signal to be filtered out from the monitored ECG signal sensed by electrodes 1361B-D.

Figure 15:
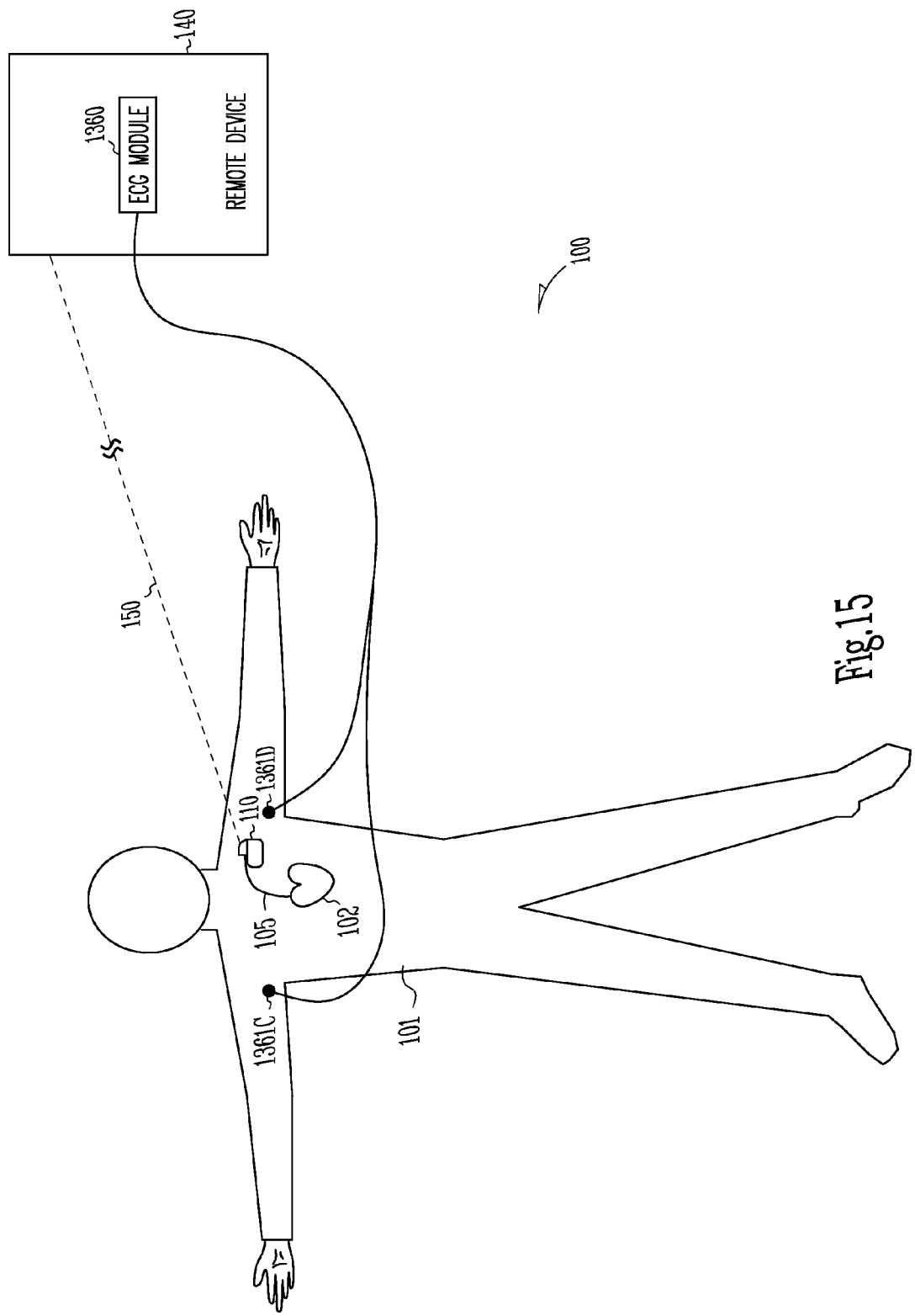
FIG. 15 is a schematic illustration of another example of portions of a telemetry power management system controlling power-on by introducing a signal through an electrocardiograph (ECG) system.

FIG. 15 is a schematic illustration of another example of portions of a telemetry power management system controlling power-on of at least a portion of the telemetry by using an electrocardiograph (ECG) system. In this example, ECG module 1360 is used for assessing the behavior of implanted device 110 by observing the cardiac signals through two input electrodes 1361C-D attached to the body surface. At least a portion of the telemetry circuit in implanted device 110 is powered on in response to a telemetry activation current signal injected into the body via electrodes 1361C-D.

Figure 16:
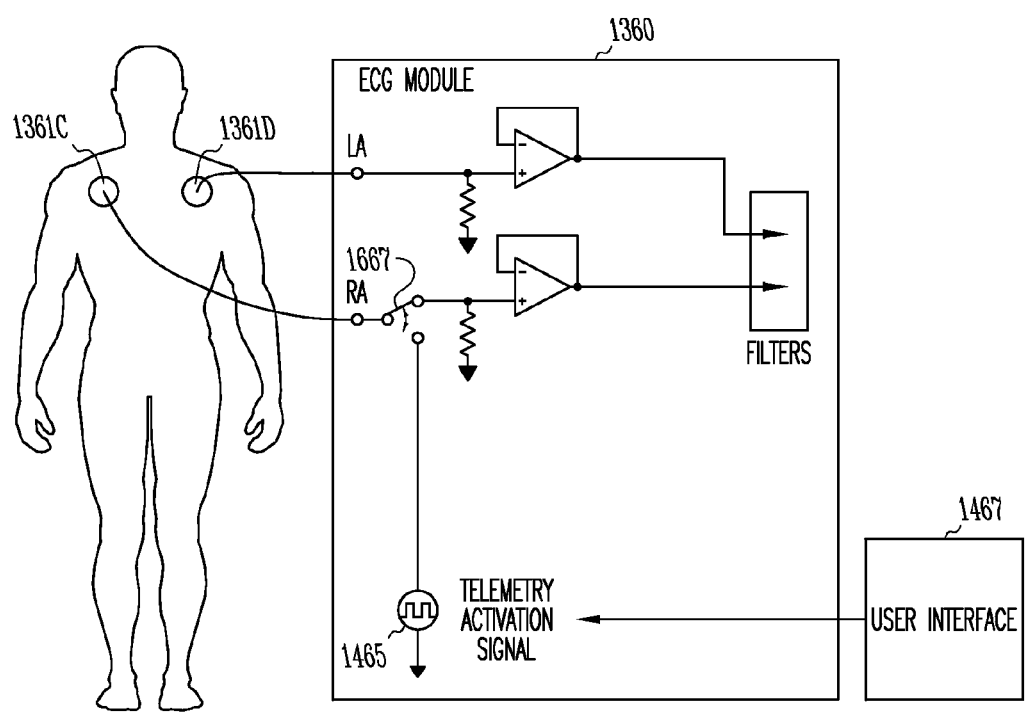
FIG. 16 is a circuit diagram illustrating one example of portions of the telemetry power management system of FIG. 15.

FIG. 16 is a circuit diagram illustrating one example of portions of the telemetry power management system of FIG. 15. In this example, ECG module 1360 is configured to operate using input electrodes 1361B-D, without right-leg negative feedback electrode 1351A. One of input electrodes 1361C and 1361D is used as an output for telemetry activation signal generator 1465, such as by using a switch 1667. In the example shown in FIG. 16, a physician or other caregiver initiates an RF telemetry session by providing an input to user interface 1467. This input causes remote device 140 to inject telemetry activation signal via input electrode 1361C.

Figure 17:
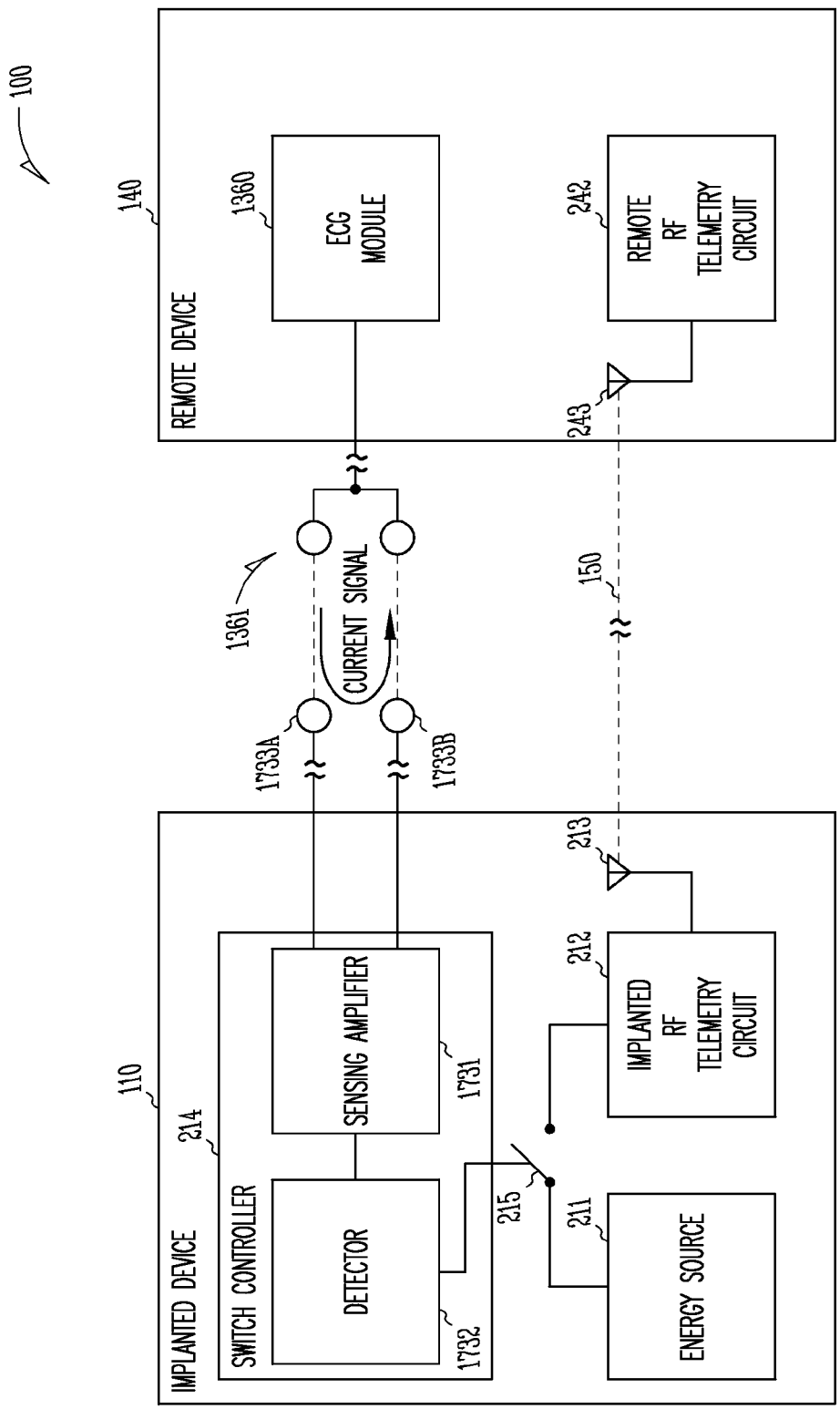
FIG. 17 is a schematic/block diagram illustrating one example of portions of a telemetry power management system corresponding to the examples of FIGS. 14 and 16.

FIG. 17 is a schematic/block diagram illustrating one example of portions of system 100 corresponding in the examples of FIGS. 14 and 16. In this example, remote device 140 includes ECG module 1360, which is coupled to electrodes 1361 attached to the patient. Electrodes 1361 include four electrodes, 1361A-D, or alternatively, two electrodes, 1361C-D, as respectively discussed above for FIGS. 14 and 16. Switch controller 214 includes a sensing amplifier 1731 and detector 1732. In one example, in addition to sensing the telemetry activation signal, sensing amplifier 1731 is also used to sense a physiological signal. Examples of the sensed physiological signal include a cardiac signal, a respiration signal, and an acceleration signal. In one example, sensing amplifier 1731 is used to sense cardiac signals via electrodes 1733A and 1733B. Electrodes 1733A-B are both electrically coupled to sensing amplifier 1731, such as through lead wires. In one example, electrodes 1733A-B are disposed in close proximity to each other in or about a heart chamber. This is referred to as bipolar sensing. In an alternative example, electrode 1733A is disposed in or about a heart chamber, and electrode 1733B is located at or near a metal housing of implanted device 110 that houses switch controller 214, energy source 211, and implanted RF telemetry circuit 212. This is referred to as unipolar sensing. Sensing amplifier 1731 typically includes an amplifier and a filter. Detector 1732 includes a comparator having one input coupled to the output of the sensing amplifier 1731, another input representative of a predetermined comparison threshold, and an output indicating whether the signal sensed via electrodes 1733A-B exceeds the threshold. The output of detector 1732 is coupled to power switch 215 to close power switch 215 when the telemetry activation signal sensed through electrodes 1733A-B exceeds the threshold. This, in turn, connects power from energy source 211 to implanted RF telemetry circuit 212. In one example, detector 1732 further includes a binary code detector that detects a digital key, also sensed via electrodes 1733A-B. In one example, use of the digital key provides added noise immunity. In another example, the digital key also identifies a particular implantable device 110 with which RF telemetry link 150 is to be established. Power switch 215 is closed when the telemetry activation signal sensed through electrodes 1733A-B exceeds the threshold and a matching digital key is detected.

Figure 18:
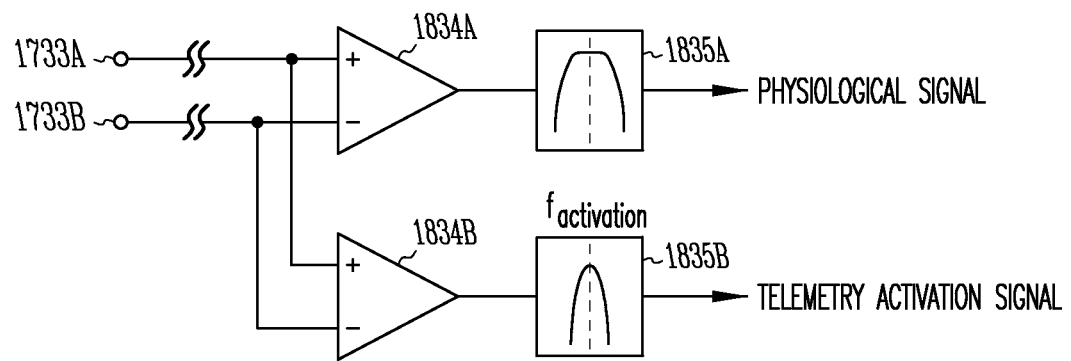
FIG. 18 is a schematic/block diagram illustrating one example of portions of a sensing amplifier.

FIG. 18 is a schematic/block diagram illustrating one example of portions of sensing amplifier 1731. In this example, amplifier 1834A is a low-frequency amplifier used to amplify the physiological signal. Amplifier 1834B is a high-frequency amplifier used to amplify the telemetry activation signal. A filter 1835A attenuates signals that are not at the physiological signal frequency. This configuration is suitable when a telemetry activation signal has a frequency that is significantly different from the physiological signal frequency, avoiding the use of a wideband amplifier that may expose implanted device 110 to a wide range of noises. In one example, the physiological signal is a cardiac signal, and filter 1835A includes a bandpass filter having a bandwidth of 150 Hz. Filter 1835B passes the telemetry activation signal to detector 1732, and attenuates signals at other frequencies. This example uses a telemetry activation signal frequency that is different, and therefore distinguishable, from that of the cardiac or other physiological signal.

Figure 19:
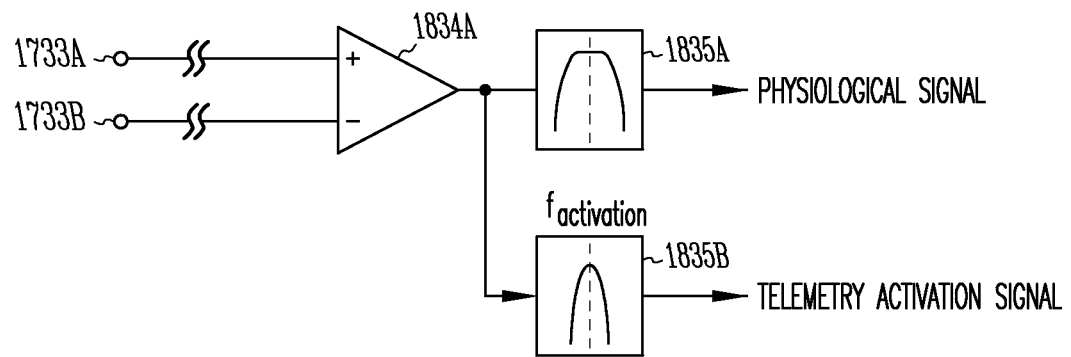
FIG. 19 is a schematic/block diagram illustrating another example of portions of a sensing amplifier.

FIG. 19 is a schematic/block diagram illustrating another example of portions of sensing amplifier 1731. In this example, sensing amplifier 1731 includes a shared amplifier 1834A and two filters 1835A-B, both coupled to the output of amplifier 1834A. This configuration is alternative implementation to that of FIG. 18, eliminating components, however, the implementation of FIG. 18 allows more design flexibility in the signal processing. In one example, the physiological signal sensed during particular time periods and the telemetry activation signal is sensed during other times. For example, a respiration signal is monitored by periodically sensing body impedance. A telemetry activation signal is injected into the body when the body impedance is not being sensed.

Figure 20:
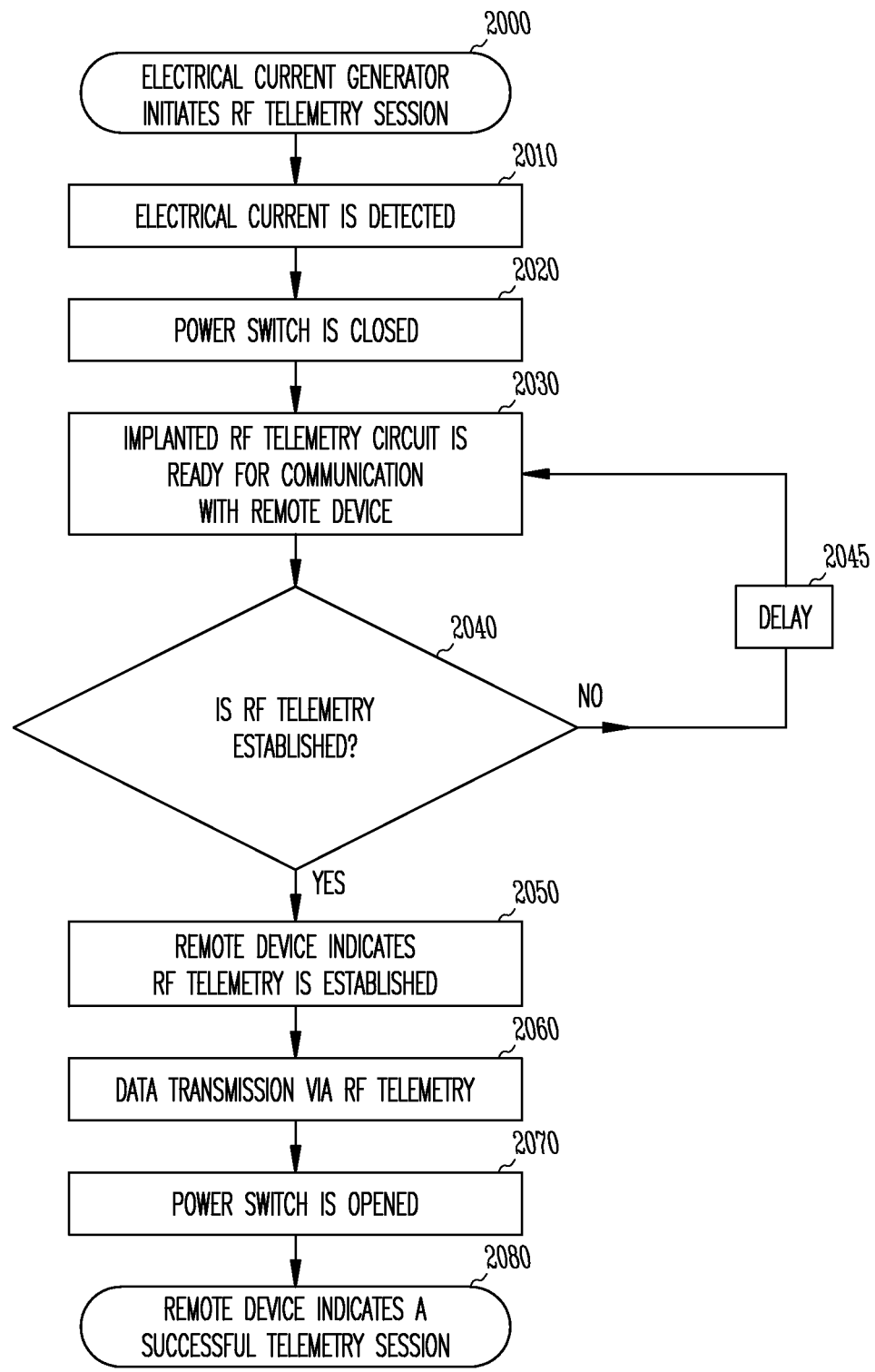
FIG. 20 is a flow chart illustrating one example of a method corresponding to the example of FIG. 17.

FIG. 20 is a flow chart illustrating one example of a method corresponding to the example of FIG. 17. At 2000, a physician or other caregiver initiates an RF telemetry session by providing input at a user interface. In response, a telemetry activation signal is introduced into a patient's body through ECG electrodes 1361. The telemetry activation signal is a short-duration electrical current signal flowing into the body when a switch in remote device 140 is momentarily closed. In one example, the telemetry activation signal includes a digital key identifying a particular implantable device 110 with which RF telemetry link 150 is to be established. In one example, the RF telemetry session is initiated for an evaluation of a patient's conditions. At 2010, the telemetry activation signal is detected by implanted device 110. In response, at 2020, power switch 215 is closed to connect power from energy source 211 to implanted RF telemetry circuit 212. At 2030, RF telemetry circuit 212 is activated and ready for bi-directional communication with remote device 140 via RF telemetry link 150. In one example, implanted RF telemetry circuit 212 sends a signal to remote device 140. If the signal is received by remote device 140, and remote device 140 is not busy communicating with other implantable device(s), remote device 140 sends a responsive signal back to implanted device 110, and the RF telemetry is established. If, at 2040, the RF telemetry is not established, because of excessive environmental noises or other reasons, RF telemetry circuit 212 will repeat 2030 after a delay 2045. In one example, delay 2045 is a programmed constant. In another example, delay 2045 is a function of the number of failed attempts to establish the RF telemetry. This function represents a particular sequence of successive attempts to establish the RF telemetry. In another example, remote device 140 periodically sends a signal including a digital key identifying a particular implantable device 110. Only upon receiving this signal, RF telemetry circuit 212 sends out a signal to remote device 140 to establish RF telemetry at 2040. At 2050, remote device 140 indicates that RF telemetry link 150 has been established. The physician or caregiver may remove ECG electrodes 1361 so that the patient's mobility is no longer limited by their connecting cable. At 2060, data is transmitted from remote device 140 to implanted device 110 and/or from implanted device 110 to remote device 140. In an idle state, after the data transmission is complete, power switch 215 is opened at 2070. This disconnects power from energy source 211 to at least a portion of RF telemetry circuit 212. Examples of methods and apparatus controlling the opening of power switch 215 are described later in this document. At 2080, remote device 140 indicates whether the telemetry session was successful, such as by logging or displaying a message.

Example of Power-on by Momentary Contacting an External Device

Figure 21:
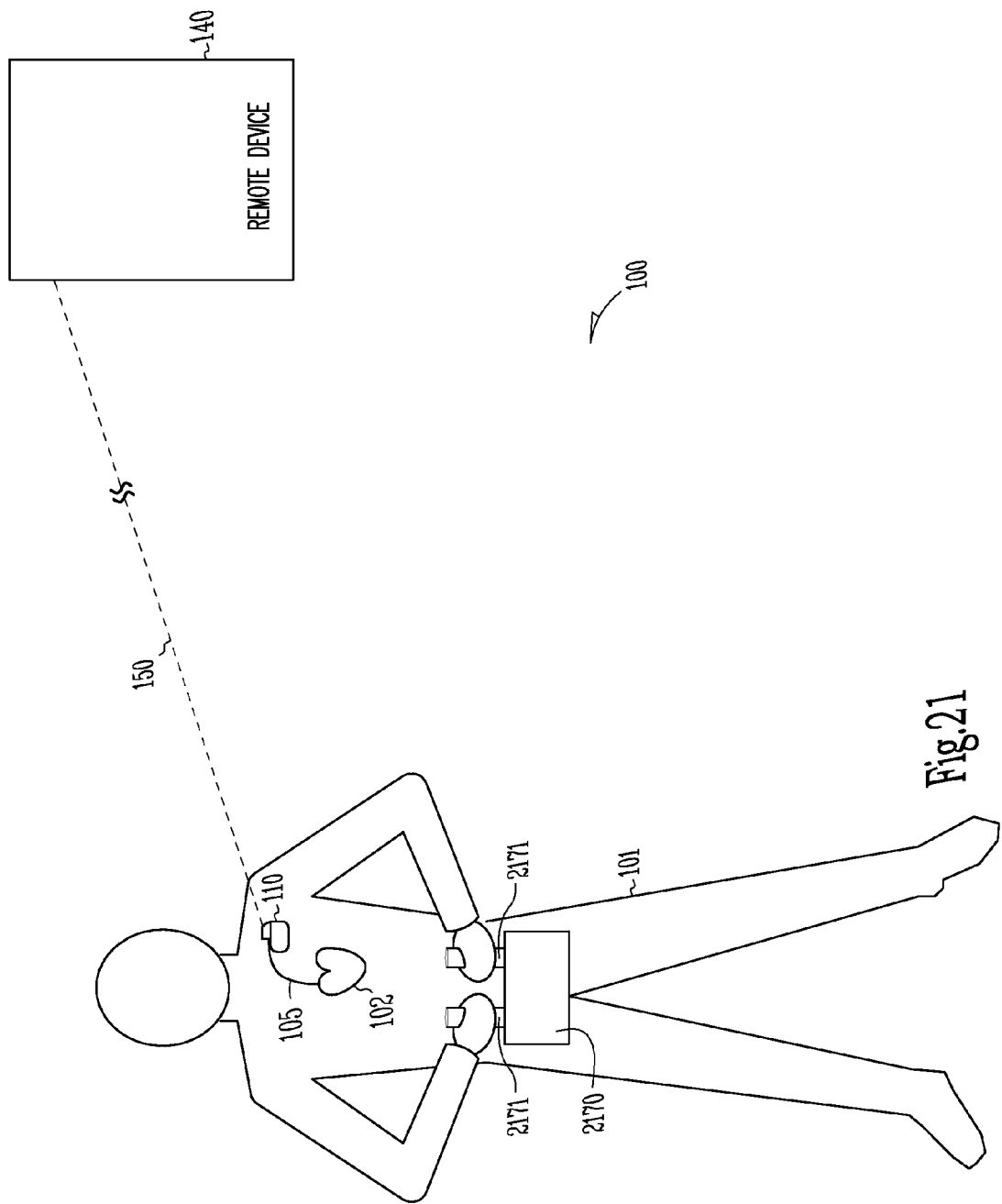
FIG. 21 is a schematic illustration of one example of portions of a telemetry power management system controlling power-on by using an external telemetry activation device.

FIG. 21 is a schematic illustration of another example of portions of a telemetry power management system controlling power-on of at least a portion of the telemetry by using an external telemetry activation device. In this example, system 100 includes a telemetry activation device 2170 that introduces a telemetry activation signal into a patient's body to be received by implanted device 110 for activating telemetry. In one example, the telemetry activation signal includes an encoded command that is distinguishable from noise that may be present on electrodes 2171. In one example, device 2170 is dedicated to telemetry activation. In another example, device 2170 is a monitoring device, or a therapy device, or any medical device or non-medical device incorporating a telemetry activation system. In one example, device 2170 includes a user input and/or output interface such as to accept commands and display telemetry activity or other status information regarding implanted device 110. Telemetry activation device 2170 includes a pair of conductive structures 2171 for contact with the patient. A small electrical current flows into the patient's body when the patient contacts both conductive structures. In the example of FIG. 21, the conductive structures include a pair of conductive joysticks. The patient holds one joystick in each hand to initiate an RF telemetry session for data transmission between implanted device 110 and remote device 140. In an alternative example, conductive structure 2171 includes two conductive patches incorporated onto a bar, a handle, or any portion of the housing of telemetry activation device 2170. In one example, the patient initiates telemetry sessions periodically to transfer acquired physiological data and/or therapy history to a physician or other caregiver. In another example, the patient initiates a telemetry session when attention of the physician or other caregiver is needed.

Figure 22:
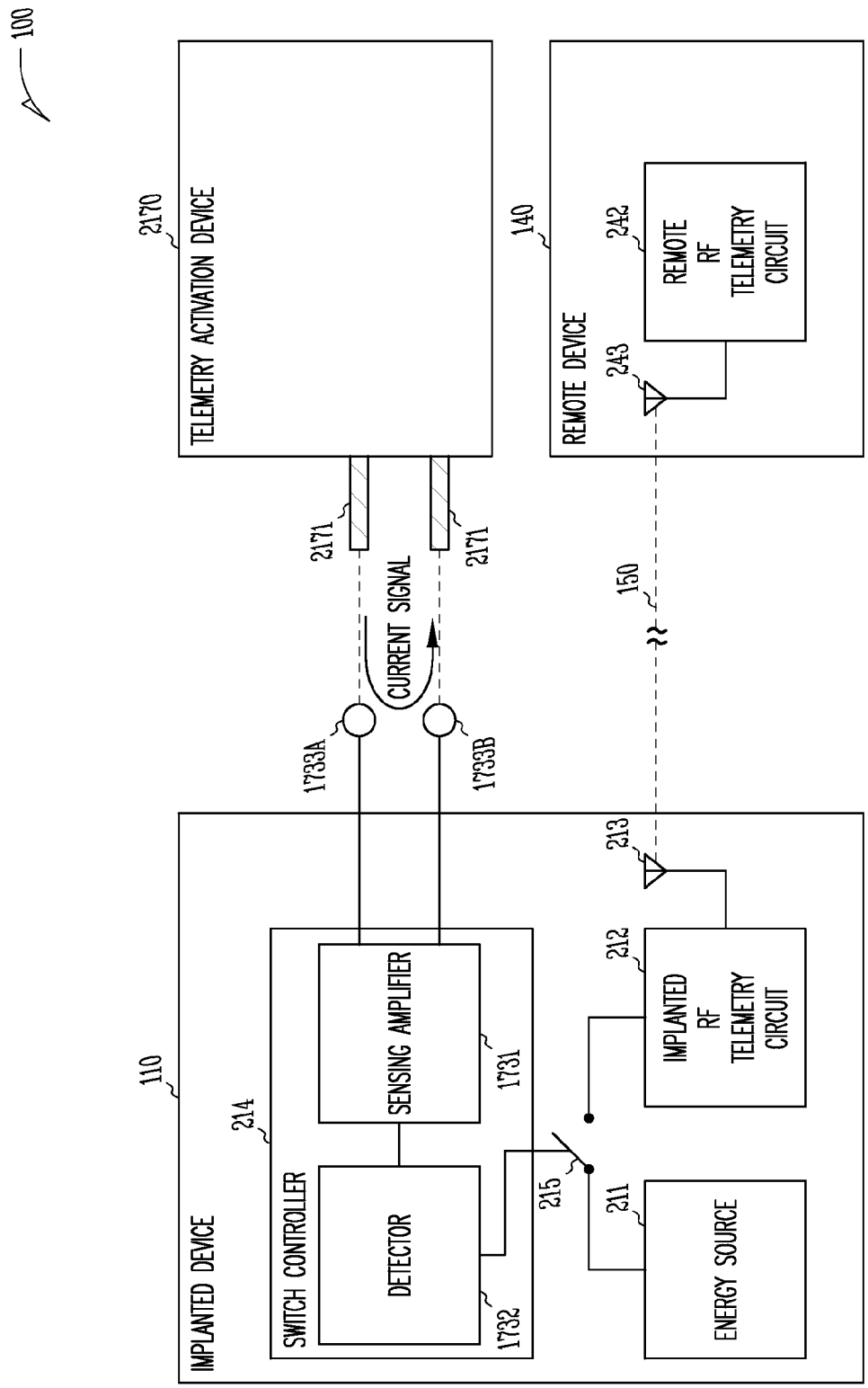
FIG. 22 is a schematic/block diagram illustrating one example of portions of telemetry power management system corresponding to the example of FIG. 21.

FIG. 22 is a schematic/block diagram illustrating one example of portions of telemetry power management system corresponding to the example of FIG. 21. In this example, system 100 includes a telemetry activation device 2170 having conductive structures 2171. Switch controller 214 includes sensing amplifier 1731 and detector 1732. In one example, sensing amplifier 1731 is also used to sense a physiological signal via electrodes 1733A-B that are electrically coupled to sensing amplifier 1731. In one example, the sensed physiological signal is a cardiac signal. Electrodes 1733A-B are configured for either bipolar sensing or unipolar sensing. Power switch 215 is closed to connect power from energy source 211 to implanted RF telemetry circuit 212 in response to the telemetry activation signal being sensed by sensing amplifier 1731 and detected by detector 1732.

Figure 23:
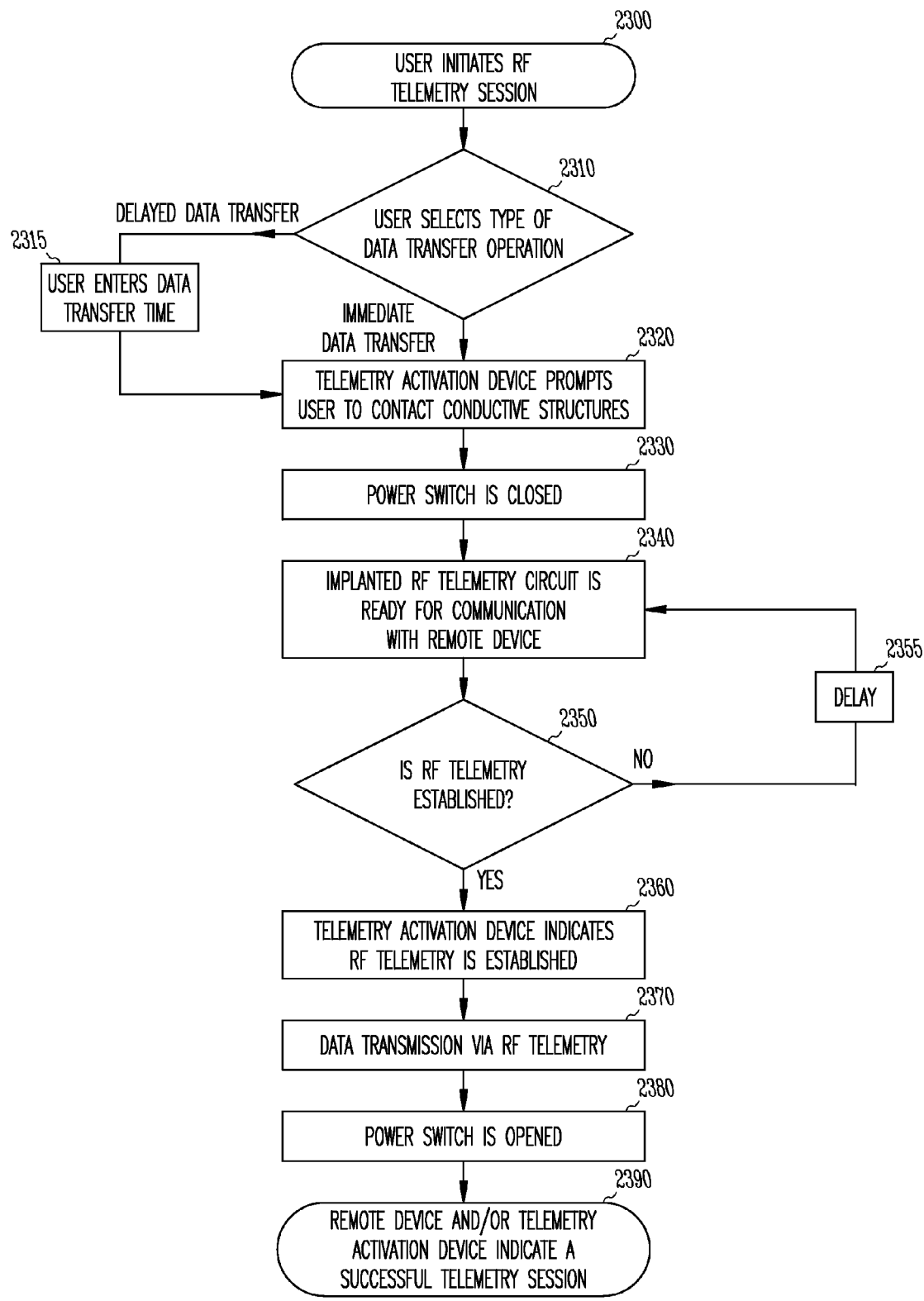
FIG. 23 is a flow chart illustrating one example of a method corresponding to the example of FIG. 22.

FIG. 23 is a flow chart illustrating one example of a method corresponding to the example of FIG. 22. At 2300, a user initiates an RF telemetry session as scheduled or needed. In one example, the user is a patient. In another example, the user is a physician or other caregiver who is supervising or examining the patient. At 2310, the user selects an operation. In the example of FIG. 23, the user may elect to transfer data from implanted device 110 to remote device 140 immediately or after a delay. If the user elects to transfer data after a delay, then at 2315, telemetry activation device 2170 prompts the user to enter a time for the data transfer. At 2320, telemetry activation device 2170 prompts the user to contact conductive structures 2171. In the example of FIG. 23, telemetry activation device 2170 prompts the user to grab the conductive joysticks on the device. In response, at 2330, power switch 215 is closed to connect power from energy source 211 to implanted RF telemetry circuit 212. At 2340, RF telemetry circuit 212 is activated and ready for bi-directional communication with remote device 140 via RF telemetry link 150. In one example, implanted RF telemetry circuit 212 sends a signal to remote device 140. If the signal is received by remote device 140, and remote device 140 is available to communicate with an implantable device, remote device 140 sends a responsive signal back to implanted device 110, and the RF telemetry is established at 2350. If the RF telemetry cannot be established at 2350, because of excessive environmental noise or other reasons, RF telemetry circuit 212 will repeat 2340 after a delay 2355. In one example, delay 2355 is a programmed constant. In another example, delay 2355 is a function of the number of failed attempts to establish the RF telemetry. This function represents a particular sequence of successive attempts to establish the RF telemetry. In another example, remote device 140 periodically sends a signal including a digital key identifying a particular implantable device 110. Only upon receiving this signal, RF telemetry circuit 212 sends out a signal to remote device 140 to establish RF telemetry at 2350. At 2360, remote device 140 indicates whether RF telemetry link 150 has been established. If so, the user may then remove hands from conductive structures 1371. At 2370, data is transmitted from remote device 140 to implanted device 110 and/or from implanted device 110 to remote device 140. After data communication is complete, the RF telemetry enters an idle state. Power switch 215 is then opened at 2380 to disconnect power from energy source 211 to at least a portion of RF telemetry circuit 212. Examples of methods and apparatuses controlling the opening of power switch 215 are described later in this document. At 2390, remote device 140 indicates whether the telemetry session was successful, such as by logging or displaying a message.

Example of Power-Off by Sending Command Via RF Telemetry

Figure 24:
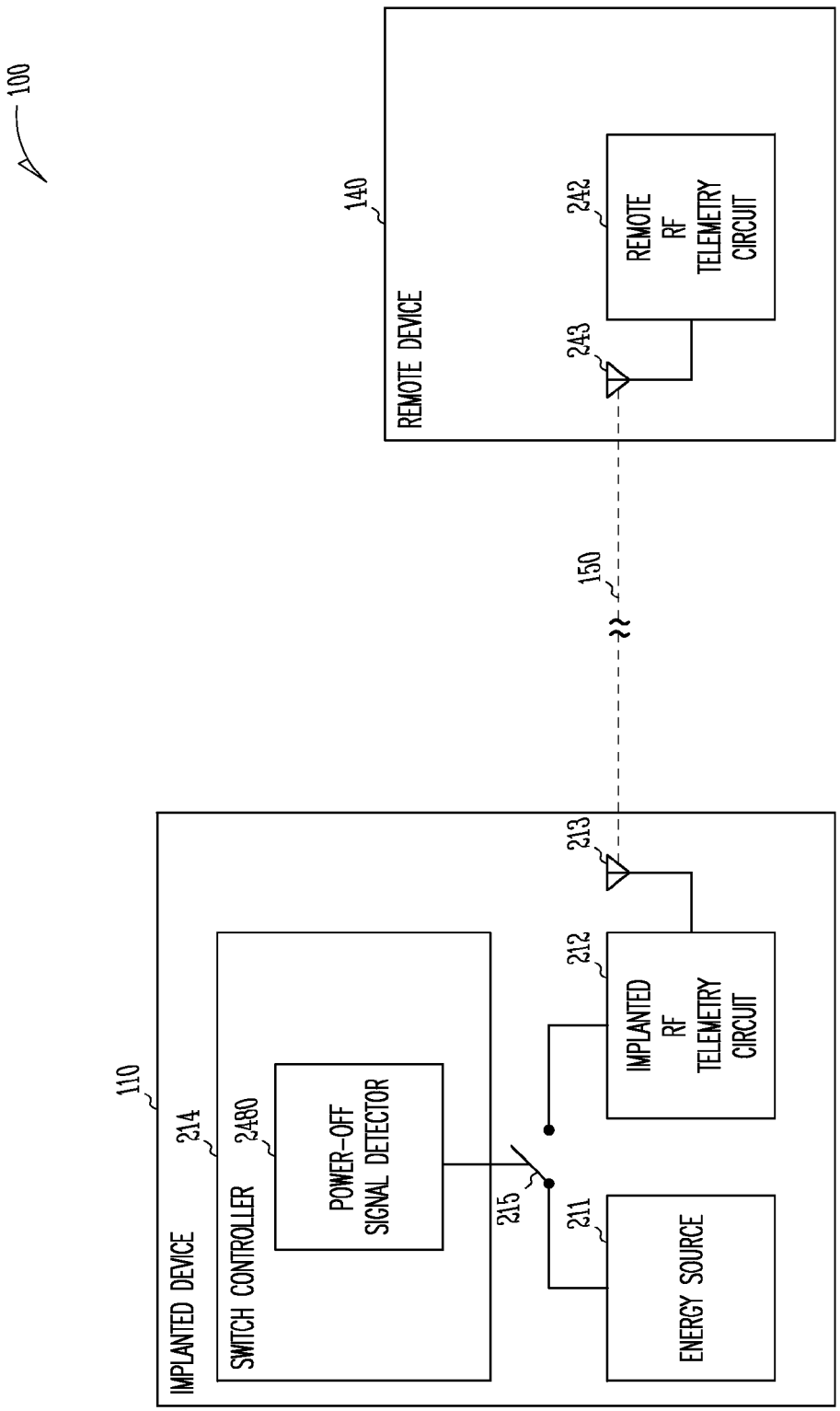
FIG. 24 is a schematic/block diagram illustrating one example of portions of a telemetry power management system controlling power-off by sending a command via RF telemetry.

FIG. 24 is a schematic/block diagram illustrating one example of portions of a telemetry power management system controlling power-off of at least a portion of the telemetry. In this example, once RF telemetry link 150 has been established by using one or more of the approaches discussed above, a telemetry power-off signal is sent to implanted device 110 via RF telemetry link 150. The telemetry power-off signal is an encoded command, such as a unique digital code. In this example, switch controller 214 includes a power-off signal detector 2480 coupled to antenna 213. Upon detection of the power-off signal, detector 2480 opens power switch 215 to disconnect the power to at least a portion of implanted RF telemetry circuit 212 from energy source 211. In a further example, detector 2480 opens power switch 215 upon detection of the power-off signal and determination that RF telemetry has entered an idle state.

Figure 25:
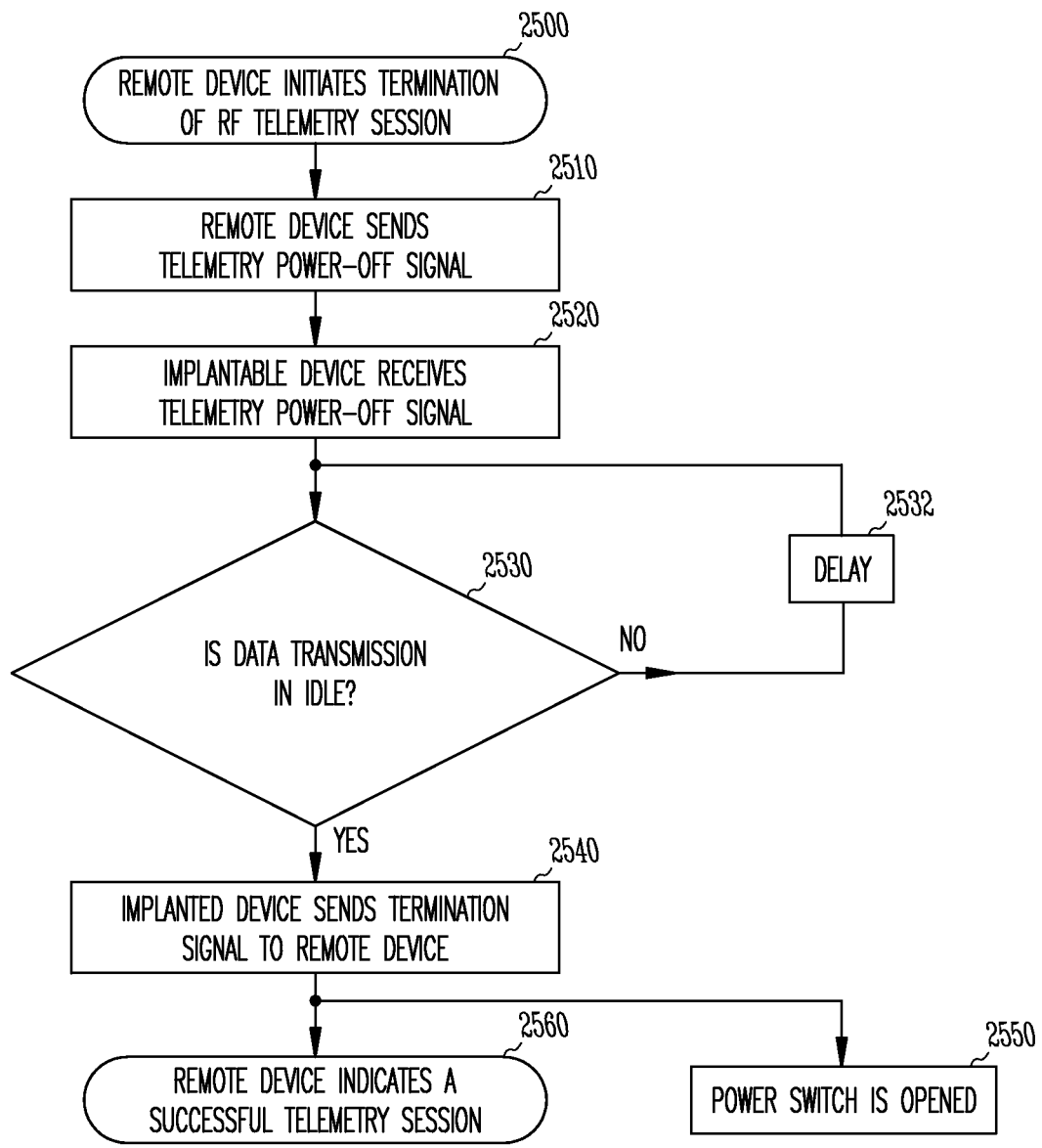
FIG. 25 is a flow chart illustrating one example of a method corresponding to the example of FIG. 24.

FIG. 25 is a flow chart illustrating one example of a method corresponding to the example of FIG. 24. At 2500, remote device 140 sends a power-off signal to implanted device 110 to terminate a previously-established RF telemetry session. In one example, a physician or other caregiver provides a user input at a user-interface that triggers the power-off signal. In another example, remote device 140 sends the power-off signal automatically when it determines that an RF telemetry session should end. For example, remote device 140 determines that an RF telemetry session should end when no data is transmitted via RF telemetry link 150 for a predetermined duration, such as ten minutes. At 2520, implanted device 110 receives the telemetry power-off signal. At 2530, power-off signal detector 2480 determines whether the RF telemetry is in an idle state, in which no data is being transferred between implanted device 110 and remote device 140. In one example, if data is being transferred, or is about to be transferred, power-off signal detector 2480 repeats a step 2530 of determining whether the RF telemetry is in an idle state after a predetermined delay 2532. At 2540, after the RF telemetry is determined to be in an idle state, implanted device 110 sends a termination signal to remote device 140 to inform remote device 140 of the completion of the RF telemetry session. Then, at 2550, power switch 215 is opened to disconnect the power to at least a portion of implanted RF telemetry circuit 212 from energy source 211. Upon receiving the termination signal from implanted device 110, remote device 140 indicates a successful completion of the RF telemetry session at 2560, such as by logging or displaying a message.

Example of Power-Off by Timing

Figure 26:
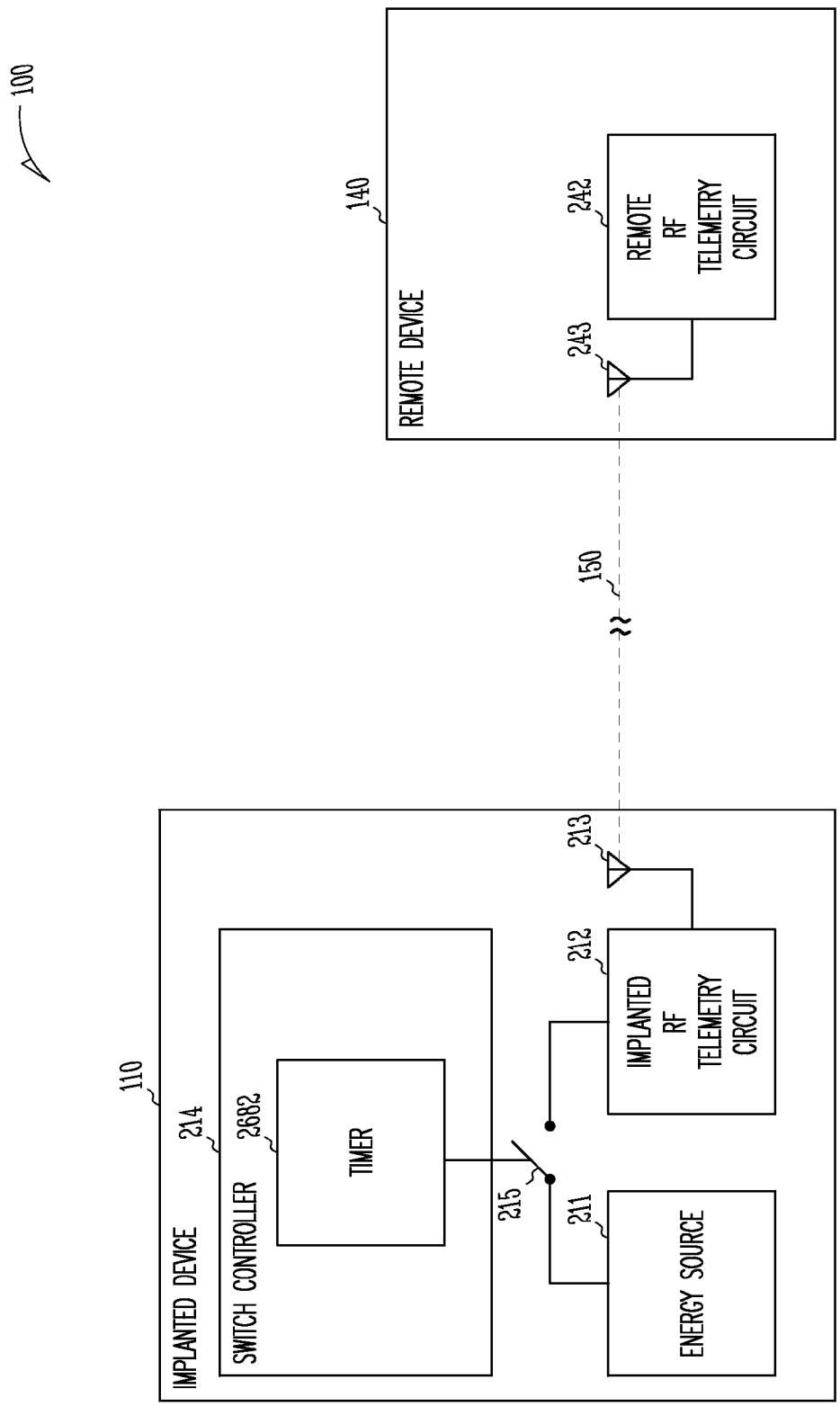
FIG. 26 is a schematic/block diagram illustrating one example of portions of a telemetry power management system controlling power-off by using a timer.

FIG. 26 is a schematic/block diagram illustrating another example of portions of a telemetry power management system controlling power-off of at least a portion of the telemetry. In this example, switch controller 214 includes a timer 2682 coupled to implantable RF telemetry circuit 212. Timer 2682 starts timing an interval when the RF telemetry enters an idle state. If data transmission via the RF telemetry resumes during the predetermined delay, timer 2682 is reset and does not restart until the RF telemetry enters another idle state. If the delay expires during the idle state, timer 2682 opens power switch 215 to disconnect the power to at least a portion of implanted RF telemetry circuit 212 from energy source 211.

Figure 27:
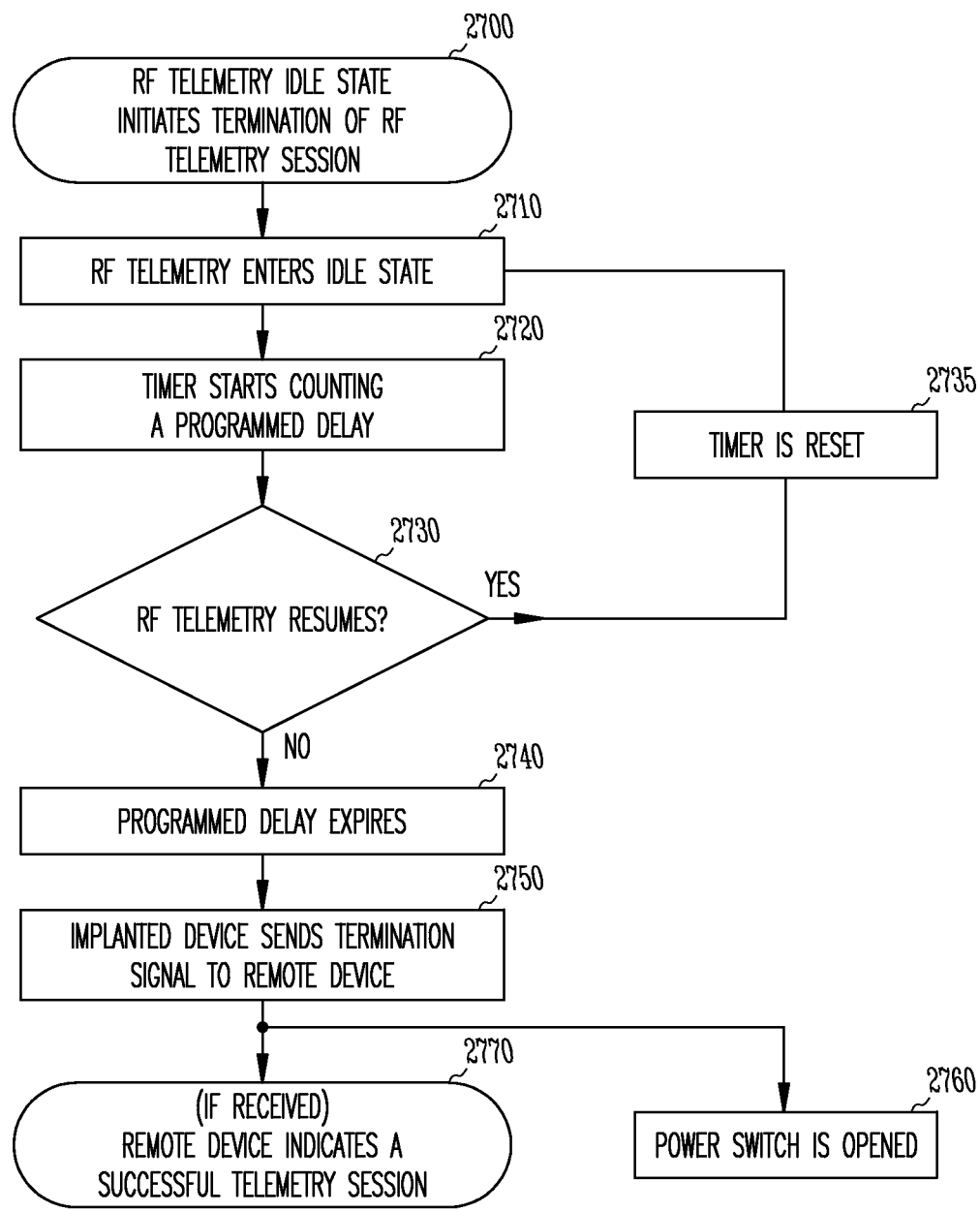
FIG. 27 is a flow chart illustrating one example of a method corresponding to the example of FIG. 26.

FIG. 27 is a flow chart illustrating one example of a method corresponding to the example of FIG. 26. In this example, an idle state of the RF telemetry, during which no data is transmitted between implanted device 110 and remote device 140, terminates RF telemetry session at 2700. At 2710, when the RF telemetry enters an idle state, timer 2682 is then started at 2720 to measure a time spent in the idle state. If data transmission via RF telemetry link 150 resumes at 2730, before the time value exceeds a predetermined delay, timer 2682 is reset (re-zeroed) and is to be restarted upon reentering the idle state. If data transmission via RF telemetry link 150 does not resume before the time value exceeds the predetermined delay at 2740, implanted device 110 then sends a termination signal to remote device 140 to inform remote device 140 of the completion of the RF telemetry session. At 2760, power switch 215 is opened to disconnect the power to at least a portion of implanted RF telemetry circuit 212 from energy source 211. At 2770, if the termination signal from implanted device 110 is received, remote device 140 indicates a successful completion of the RF telemetry session, such as by logging or displaying a message.

Example of Power-Off by Using Inductive Telemetry

Figure 28:
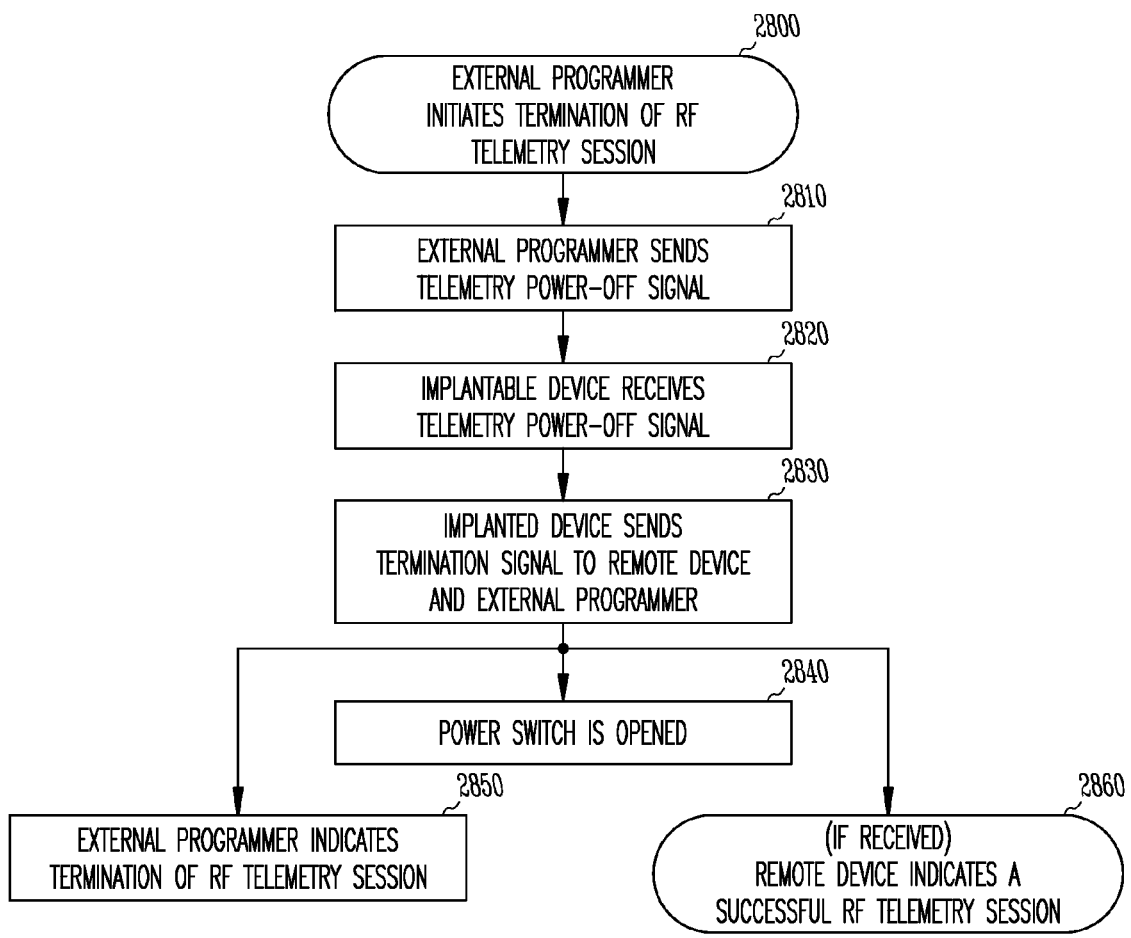
FIG. 28 is a flow chart illustrating one example of a method corresponding to one example of a telemetry power management system controlling power-off by using an inductive telemetry.

In one example, once RF telemetry link 150 has been established, a physician or other caregiver uses the inductive telemetry link 755 of FIG. 7 or 8, to end the RF telemetry session. This allows immediate shutoff of RF telemetry link 150 regardless of whether the RF telemetry is in the idle state. An encoded RF telemetry power-off signal is sent from external programmer 745 to implanted device 110 through inductive telemetry link 755. Upon detection of the RF telemetry power-off signal, implanted inductive telemetry circuit opens power switch 215 to disconnect the power to at least a portion of implanted RF telemetry circuit 212 from energy source 211. FIG. 28 is a flow chart illustrating one example of a method corresponding to this example.

In the example of FIG. 28, at 2800, a physician or other caregiver provides input to a user interface that causes external programmer 745 to terminate a previously-established RF telemetry session. In one example, the physician or other caregiver wants to terminate RF telemetry because a checkup, diagnosis, or treatment session has been completed, and the RF telemetry is no longer needed. In another example, physician or other caregiver want to establish RF telemetry with a different implanted device. Upon receiving the RF telemetry termination command, external programmer 745 sends the encoded RF telemetry power-off signal to implanted device 110 at 2810. At 2820, implanted device 110 receives the RF telemetry power-off signal. At 2830, implanted device 110 sends a responsive termination signal to remote device 140 to inform remote device 140 and external programmer 745 of the completion of the RF telemetry session. At 2840, power switch 215 is opened to disconnect the power to at least a portion of implanted RF telemetry circuit 212 from energy source 211. At 2850, upon receiving the termination signal, external programmer 745 indicates termination of the RF telemetry session. At 2860, if the termination signal from implanted device 110 is received, remote device 140 indicates the termination RF telemetry session, such as by logging or displaying a message.

Example Choice of Power on/Off Methods

Each power-on or power-off method discussed above offers advantages, which are discussed herein by way as example, and not by way of limitation. Power-on by RF burst signal allows an RF telemetry session to be initiated at remote device 140. This allows a physician or other caregiver to provide care to a patient from a remote location. An examination of the patient may be performed with or without the patient's knowledge. In one example, the patient's routine check-up is performed through the RF telemetry and telephone, so that the patient saves a trip to a physician's office. In another example, the patient who needs close monitoring is frequently checked by the physician or other caregiver through the RF telemetry, so that the patient need not be hospitalized to receive similar care. Power-on by physical activity allows an RF telemetry session to be initiated by a patient or a person with the patient. No additional external device is required. In one example, implanted device 110 already includes an accelerometer as an activity or metabolic need sensor employed in a therapy algorithm. The same accelerometer may be used for telemetry power management by modifying only software. Power-on of RF telemetry using inductive telemetry is convenient when implanted device 110 includes an inductive telemetry system. Having external programmer 745 available during an RF telemetry session also provides an alternative communications modality if RF telemetry is lost because of RF interference or other reasons. Power-on by magnetic field allows RF telemetry power management using a magnet or a hand-held device. This is likely more convenient to handle than external programmer 745. In one example, implanted device 110 already includes a function activated or suppressed by an external magnet. For example, holding a magnet near implanted device 110 may cause it to pace at a fixed pacing rate, overriding any therapy algorithm that would be otherwise effective. Using a magnetic field for RF telemetry power management in this example may be implemented by modifying only software. Power-on by introducing a signal via surface ECG electrodes is convenient when remote device 140 includes an ECG module. During a patient's follow-up visit to a physician, the physician typically attaches ECG electrodes to the patient to diagnose the patient's condition. By automatically detecting when the cables from such ECG electrodes are connected to the programmer, telemetry is seamlessly automatically activated without requiring physician intervention. In another example, using RF telemetry provides for a higher rate of data transmission as compared with inductive telemetry, reducing the duration of a telemetry session. Power-on by momentarily contacting an external device allows a patient to initiate and/or schedule an RF telemetry session and is convenient for patients who regularly use a medical device such as a monitor.

Power-off by sending a command via RF telemetry deactivates implanted RF telemetry circuit 212 without wasting power by keeping the RF telemetry power on longer than necessary. However, under some circumstances RF telemetry link 150 may be interrupted before the power-off signal is sent to implanted device 110. Examples of such circumstances include a strong RF noise or a patient moving beyond a range of the RF telemetry. Under such circumstances, power-off using a timer ensures that implanted RF telemetry circuit is shut off after the RF telemetry has been idle for a predetermined period of time. Power-off using inductive telemetry permits the physician or other caregiver to immediately terminate the RF telemetry at any time. In one example, the physician or other caregiver terminates an RF telemetry that is accidentally established with an unintended implantable device. An inductive telemetry is less likely to be accidentally established because it often requires the wand to be closely (within a few inches) coupled to the implantable device. In another example, the physician or other caregiver may terminate the RF telemetry by using the inductive telemetry, such as when one or more other power-off methods fail. In a further example, the one or more other power-off methods fail because of the presence of a noise, such as a cellular phone signal.

Depending on the patient's needs for care and type of implantable device, one or more of the power-on methods and one or more of the power-off methods discussed above may be included in one implantable device. Using more than one method to connect/disconnect power from energy source 211 to implanted RF telemetry circuit 212, or at least portions thereof, increases the reliability of initiating and terminating the RF telemetry session in a timely manner. This ensures patient safety, conserves energy, and hence increases device longevity. If one method fails, another available method may be automatically or manually applied. In one example, implanted device 110 employs one power-on method but several power-off methods, such as all three discussed above. This decreases energy waste and patient risks by ensuring that implanted RF telemetry circuit 212 is deactivated as soon as the RF telemetry session ends.

It is to be understood that the above description is intended to be illustrative, and not restrictive. For example, the implantable device can be any implantable medical device having an active electronic circuit. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system including:
    an implantable medical device, the implantable medical device including:
        a far-field radio-frequency (RF) first telemetry circuit;
        a power connection module, coupled to the first telemetry circuit, the power connection module including a first conductivity state to connect power to at least a portion of the first telemetry circuit and a second conductivity state to disconnect the power;
        a wireless signal detector, configured to change the connectivity state of the power connection module to connect power to at least a portion of the first telemetry circuit according to information detected in a wireless signal; and a timer, coupled to the power connection module, to change a conductivity state of the power connection module to disconnect power to at least a portion of the first telemetry circuit after waiting a predetermined period of time after the first telemetry circuit enters a predetermined state that includes at least one of a data transmission idle state and a telemetry establishment failure state.

2. The system of claim 1, in which the implantable medical device includes an implantable cardiac rhythm management device, and the first telemetry circuit provides at least a six-foot telemetry range.

3. The system of claim 1, wherein the wireless signal detector includes a low power radio-receiver coupled to the power connection module, and wherein the wireless signal detector is configured to connect power to at least a portion of the first telemetry circuit according to information received using the low power radio-receiver.

4. The system of claim 3, wherein the wireless signal detector is configured to connect power to at least a portion of the first telemetry circuit when receiving a high-power RF burst signal using the low power radio-receiver.

5. The system of claim 3, wherein the low power radio-receiver is configured to generate an out indicating detection of the information when detecting an envelope of an RF signal that exceeds a predetermined detection threshold.

6. The system of claim 3, wherein the wireless signal detector is configured to connect power to at least a portion of the first telemetry circuit according to information that includes a digital key identifying a particular implantable device.

7. The system of claim 3, further including a remote programming device including a telemetry activation signal generator configured to be electromagnetically coupled to the low power radio-receiver.

8. The system of claim 7, wherein the first telemetry circuit enters the telemetry establishment failure state when the digital key does not match the implantable device receiving the information.

9. The system of claim 7, wherein the first telemetry circuit enters the telemetry establishment failure state when a predetermined number of attempts to establish telemetry are unsuccessful.

10. The system of claim 1, wherein the timer is started when the first telemetry circuit enters an idle state, is reset when a data transmission is received via the first telemetry circuit, and is restarted when the first telemetry circuit reenters the idle state.

11. The system of claim 1, wherein the first telemetry circuit is configured to send a termination signal to a separate device after waiting the predetermined period of time.

12. The system of claim 1, wherein the wireless signal detector is configured to change the connectivity state of the power connection module to disconnect power to at least a portion of the first telemetry circuit according to information detected in the wireless signal, and wherein the first telemetry circuit is configured to the idle state after a predetermined amount of time when a wireless signal is not detected.

13. The system of claim 1, wherein the wireless signal detector includes a near-field inductive second telemetry circuit coupled to the power connection module, and configured to change the conductivity state of the power connection module to connect power to at least a portion of the first telemetry circuit according to information detected in a wireless near-field inductive signal.

14. The system of claim 13, in which the second telemetry circuit includes a receiver adapted to receive the predetermined wireless signal, and in which the predetermined wireless signal includes a command for changing the conductivity state of the power connection module.

15. The system of claim 13, in which the second telemetry circuit includes a receiver adapted to detect a near-field inductive signal having a predetermined frequency and to change the conductivity state of the power connection module when the near-field inductive signal is detected.

16. The system of claim 13, in which the second telemetry circuit includes a receiver adapted to detect a near-field inductive telemetry communication and to change the conductivity state of the power connection module when the near-field inductive telemetry communication is detected.

17. The system of claim 13, further including:
a first remote device, electromagnetically coupled to the first telemetry circuit, the first remote device including a far-field RF third telemetry circuit to provide communication with the implantable medical device for at least a six-foot range; and
a second remote device, inductively coupled to the second telemetry circuit, the second remote device including a near-field inductive fourth telemetry circuit to provide near-field communication with the implantable medical device.

18. The system of claim 17, in which the first and second remote devices are physically integrated.

19. The system of claim 1 wherein the implantable medical device includes a cardiac rhythm management device that provides cardiac resynchronization therapy.

20. The system of claim 1, further including a remote device far-field RF second telemetry circuit, electromagnetically coupled to the first telemetry circuit, to provide long-range communications with the implantable medical device.

* * * * *